US010105224B2

(12) United States Patent
Buchbinder et al.

(10) Patent No.: US 10,105,224 B2
(45) Date of Patent: Oct. 23, 2018

(54) CARDIAC VALVE SUPPORT STRUCTURE

(71) Applicant: MVALVE TECHNOLOGIES LTD., Herzliya (IL)

(72) Inventors: Maurice Buchbinder, La Jolla, CA (US); Julie Logan, La Jolla, CA (US); Shay Dubi, Tel Aviv (IL); Amit Tubishevitz, Tel Aviv (IL); Avi Eftel, Tel Aviv (IL)

(73) Assignee: MVALVE TECHNOLOGIES LTD., Herzliya (IL)

( * ) Notice: Subject to any disclaimer, the term of this patent is extended or adjusted under 35 U.S.C. 154(b) by 700 days.

(21) Appl. No.: 13/790,174

(22) Filed: Mar. 8, 2013

(65) Prior Publication Data

US 2014/0005778 A1 Jan. 2, 2014

Related U.S. Application Data

(63) Continuation-in-part of application No. 13/224,124, filed on Sep. 1, 2011, now Pat. No. 9,301,836.

(60) Provisional application No. 61/620,679, filed on Apr. 5, 2012, provisional application No. 61/639,924, filed on Apr. 29, 2012, provisional application No. 61/646,332, filed on May 13, 2012, provisional application No. 61/650,559, filed on May 23, 2012, (Continued)

(51) Int. Cl.
*A61F 2/24* (2006.01)
*A61F 2/82* (2013.01)
*A61F 2/852* (2013.01)

(52) U.S. Cl.
CPC .......... *A61F 2/2445* (2013.01); *A61F 2/2409* (2013.01); *A61F 2/2412* (2013.01); *A61F 2/2418* (2013.01); *A61F 2/2427* (2013.01); *A61F 2/2436* (2013.01); *A61F 2/2442* (2013.01); *A61F 2/2454* (2013.01); *A61F 2/2466* (2013.01); *A61F 2/852* (2013.01); *A61F 2002/826* (2013.01); *A61F 2210/0014* (2013.01); *A61F 2220/0008* (2013.01); *A61F 2220/0025* (2013.01); *A61F 2230/001* (2013.01); *A61F 2250/006* (2013.01); *A61F 2250/0036* (2013.01); *A61F 2250/0063* (2013.01)

(58) Field of Classification Search
CPC ................. A61F 2/2445; A61F 2/2409; A61F 2/2442–2/2448; A61F 2/2454
See application file for complete search history.

(56) References Cited

U.S. PATENT DOCUMENTS 7,585,321 B2   9/2009   Cribier
7,753,923 B2   7/2010   St. Goar et al.
(Continued)

FOREIGN PATENT DOCUMENTS

CN       1610529 A    4/2005
CN       101374478    2/2009
(Continued)

OTHER PUBLICATIONS

Extended European Search Report issued in Application No. 11822677.8 dated Aug. 17, 2015.
(Continued)

*Primary Examiner* — Yashita Sharma
*Assistant Examiner* — Rebecca Preston
(74) *Attorney, Agent, or Firm* — Nixon & Vanderhye P.C.

(57) ABSTRACT

Cardiac valve supports and their methods of use.

14 Claims, 60 Drawing Sheets

Related U.S. Application Data provisional application No. 61/720,666, filed on Oct. 31, 2012, provisional application No. 61/752,994, filed on Jan. 16, 2013, provisional application No. 61/379,235, filed on Sep. 1, 2010.

(56) References Cited

U.S. PATENT DOCUMENTS

| | | | |
|---|---|---|---|
| 2002/0151970 A1 | 10/2002 | Garrison et al. | |
| 2004/0210306 A1* | 10/2004 | Quijano | A61F 2/2418 623/2.17 |
| 2005/0075713 A1 | 4/2005 | Biancucci et al. | |
| 2005/0075728 A1 | 4/2005 | Nguyen et al. | |
| 2005/0137689 A1 | 6/2005 | Salahieh et al. | |
| 2006/0235509 A1 | 10/2006 | Lafontaine | |
| 2007/0162103 A1 | 7/2007 | Case et al. | |
| 2008/0065204 A1 | 3/2008 | Macoviak et al. | |
| 2008/0140189 A1 | 6/2008 | Nguyen et al. | |
| 2009/0005863 A1* | 1/2009 | Goetz | A61F 2/2418 623/2.18 |
| 2009/0171432 A1 | 7/2009 | Von Segesser et al. | |
| 2009/0177277 A1 | 7/2009 | Milo | |
| 2010/0145440 A1 | 6/2010 | Keranen | |
| 2010/0161036 A1 | 6/2010 | Pintor et al. | |
| 2010/0185277 A1* | 7/2010 | Braido | A61F 2/2412 623/2.18 |
| 2011/0004237 A1* | 1/2011 | Schneider | A61F 2/86 606/194 |
| 2011/0029072 A1* | 2/2011 | Gabbay | A61F 2/2409 623/2.23 |
| 2011/0137397 A1 | 6/2011 | Chau et al. | |
| 2011/0137410 A1 | 6/2011 | Hacohen | |
| 2011/0319990 A1 | 12/2011 | Macoviak et al. | |
| 2012/0016464 A1 | 1/2012 | Seguin | |
| 2012/0022629 A1 | 1/2012 | Perera et al. | |
| 2013/0035759 A1 | 2/2013 | Gross et al. | |

FOREIGN PATENT DOCUMENTS

| | | |
|---|---|---|
| CN | 101588771 A | 11/2009 |
| EP | 2 422 750 | 2/2012 |
| JP | 2009-195712 | 9/2009 |
| WO | WO 2007/089625 | 8/2007 |
| WO | 2008/070797 | 6/2008 |
| WO | WO 2012/031141 | 3/2012 |
| WO | WO 2012/174383 | 12/2012 |

OTHER PUBLICATIONS

Office Action dated Dec. 23, 2014 in Chinese App. No. 201180052374.2 (w/ partial English translation).

Office Action issued in U.S. Appl. No. 13/224,124 dated Oct. 8, 2013.

Office Action issued in U.S. Appl. No. 13/224,124 dated Jul. 8, 2014.

International Search Report issued in International Application No. PCT/US2011/050232 dated Apr. 12, 2012.

Written Opinion of the International Searching Authority issued in International Application No. PCT/US2011/050232 dated Apr. 12, 2012.

International Preliminary Report on Patentability issued in International Application No. PCT/US2011/050232 dated Mar. 5, 2013.

International Search Report for PCT/IL2013/000025 dated Jun. 18, 2013.

Written Opinion of the International Searching Authority for PCT/IL2013/000025 dated Jun. 18, 2013.

Co-pending U.S. Appl. No. 14/471,575, filed Aug. 28, 2014 in the name of Buchbinder et al.

U.S. Office Action issued in U.S. Appl. No. 14/471,575 dated Jul. 1, 2016.

* cited by examiner

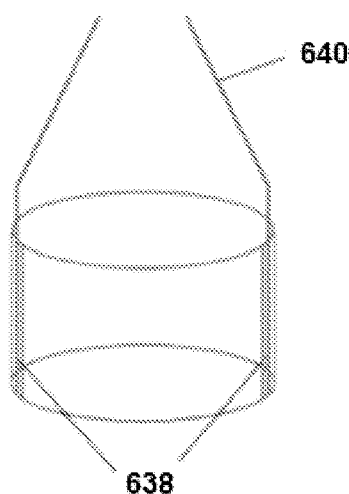
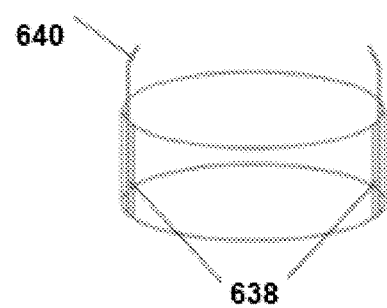
FIG 29A
FIG 29B
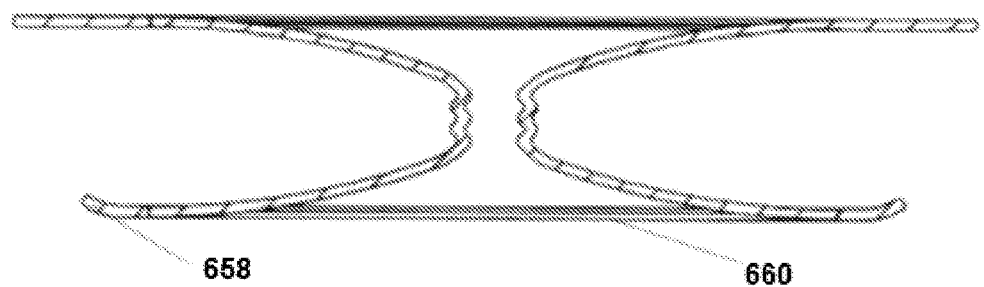
FIG 30

CARDIAC VALVE SUPPORT STRUCTURE

CROSS REFERENCE TO RELATED APPLICATIONS

This application is a continuation-in-part of U.S. patent application Ser. No. 13/224,124, filed Sep. 1, 2011, which claims the benefit of U.S. Provisional Application No. 61/379,235, filed Sep. 1, 2010, and this application also claims the benefit of U.S. Provisional Application Nos. 61/620,679 filed on Apr. 5, 2012, 61/639,924 filed on Apr. 29, 2012, 61/646,332 filed on May 13, 2012, 61/650,559 filed on May 23, 2012, 61/720,666 filed on Oct. 31, 2012, and 61/752,994 filed on Jan. 16, 2013, the contents of each of which are incorporated herein by reference.

BACKGROUND OF THE DISCLOSURE

Heart valve regurgitation occurs when the heart leaflets do not completely close when the heart contracts. When the heart contracts, blood flows back through the improperly closed leaflets. For example, mitral valve regurgitation occurs when blood flows back through the mitral valve and into the left atrium when the ventricle contracts.

In some instances regurgitation occurs due to disease of the valve leaflets (e.g., primary, or "organic" regurgitation). Regurgitation can also be cause by dilatation of the left ventricle, which can lead to secondary dilatation of the mitral valve annulus. Dilation of the annulus spreads the mitral valve leaflets apart and creates poor tip cooptation and secondary leakage, or so-called "functional regurgitation."

Currently, primary regurgitation is corrected by attempting to remodel the native leaflets, such as with clips, sutures, hooks, etc., to allow them to close completely when the heart contracts. When the disease is too far advanced, the entire valve needs to be replaced with a prosthesis, either mechanical or biologic. Examples include suture annuloplasty rings all the way to actual valve replacement with leaflets, wherein the suture rings are sutured to the mitral valve annulus. Annuloplasty rings, which are also sutured to the annulus, have also been used to attempt to remodel the annulus, bringing the native leaflets closer together to allow them to properly close.

Based on the success of catheter-based aortic valve replacement there is growing interest in evaluating similar technologies to replace the mitral valve non-invasively using similar types of replacement valves.

Unlike the aortic valve, however, the mitral valve annulus does not provide a good landmark for positioning a replacement valve. In patients needing a replacement aortic valve, the height and width of the aortic annulus are generally increased in the presence of degenerative disease associated with calcium formation. These changes in tissue make it easier to properly secure a replacement aortic valve in place due to the reduced cross-sectional area of the aortic annulus. The degenerative changes typically found in aortic valves are not, however, present in mitral valves experiencing regurgitation, and a mitral valve annulus is therefore generally thinner than the annulus of a diseased aortic valve. The thinner mitral valve annulus makes it relatively more difficult to properly seat a replacement cardiac valve in the native mitral valve annulus. The general anatomy of the mitral valve annulus also makes it more difficult to properly anchor a replacement heart valve in place. The mitral valve annulus provides for a smoother transition from the left atrium to the left ventricle than the transition that the aortic valve annulus provides from the aorta to the left ventricle. The aortic annulus is anatomically more pronounced, providing a larger "bump" to which a replacement aortic valve can more easily be secured in place.

In general, the aortic valve annulus is smaller than the mitral valve annulus. It has been estimated that the mitral valve annulus is about 2.4 cm to about 3.2 cm in diameter, while the aortic valve annulus has been estimated to be about 1.6 cm to about 2.5 cm in diameter.

The larger mitral valve annulus makes it difficult to securely implant current percutaneously delivered valves in the native mitral position. Current replacement aortic valves are limited in the amount of radial expansion they can undergo during deployment and implantation. To provide a replacement aortic valve that has an expanded configuration such that it can be securely anchored in a mitral valve annulus would require that the collapsed delivery profile of the replacement aortic valve be increased. Increasing the collapsed delivery profile, however, would make endovascular delivery more dangerous for the patient and more difficult to navigate the vasculature with a larger diameter delivery system.

Some attempts have been made to deliver and implant a one-piece replacement mitral valve, but it is difficult to provide a device that can be collapsed down to have a sufficiently small delivery profile and still be able to be expanded and secured in place within the mitral valve via a vascular access site.

A valve support structure or anchoring device is needed that can be positioned near or within the native mitral valve and that is adapted to secure a replacement cardiac valve in place.

SUMMARY OF THE INVENTION

One aspect of the disclosure is a cardiac valve support adapted for endovascular delivery to a cardiac valve, comprising: a first support element with a collapsed delivery configuration and a deployed configuration; a second support element with a collapsed delivery configuration and a deployed configuration; at least two bridging members extending from the first support element to the second support element, wherein each bridging member has a delivery configuration and a deployed configuration; wherein said bridging members extend radially inward from the first and second support elements in the deployed configuration.

In another preferred embodiment of the cardiac valve support of the present invention, said support comprises first and second support elements each having a collapsed delivery configuration and a deployed configuration;

and wherein at least two bridging members extend from the first support element to the second support element, said bridging members having a delivery configuration and a deployed configuration, wherein said bridging members extend longitudinally, and without any appreciable radial curvature, between first and second support elements in the deployed configuration.

The phrase "without any appreciable radial curvature" should be understood, in the context of the present disclosure to indicate that the bridges appear to be entirely straight and non-curved when observed with the unaided eye.

Although the cardiac valve support of the present invention may comprise two or more bridging members, in one preferred embodiment thereof, said valve support is fitted with exactly two bridging members.

In some embodiments the first and second bridging members extend from first and second discrete locations around the first and second support elements, and can symmetrically extend from the first and second support elements. The first and second bridging members can extend from the first and second support elements about 180 degrees from one another In certain other embodiments, the valve support device may optionally further comprise secondary bridging members (occasionally referred to hereinafter as "bridges") that mutually interconnect two or more main bridging members. In other embodiments, secondary bridging members are used to connect one or more of the main bridging members with the support elements. The term "secondary bridging members" is used in this context to distinguish said optional, additional bridges from the main bridging members that connect the first and second support elements, as disclosed hereinabove.

In preferred embodiments at least one of the first and second support elements has an annular shape.

The annular support element may have an outline shape that is circular, elliptical or any other form that permits it to be adapted to make close contact with the inner cardiac wall upon implantation in the region of a cardiac valve annulus.

In one preferred embodiment of the valve support device of the present invention the outer perimeter of at least one of the two support elements is entirely rigid, such that in its deployed configuration, it is not possible to cause further expansion of the outer diameter of said device.

In the radial plane (i.e. the plane in which the native cardiac valve leaflets are disposed when in their closed position), the size of at least one of the support elements (the upper of the two elements, after deployment) may be defined in terms of its outer radius (Ro), its inner radius (Ri) and the difference between these two radii (Rd). It should be appreciated that Ro is determined by the diameter of the mitral valve annulus into which the valve support device will be implanted. Ri, however, is determined by the outer diameter of the replacement heart valve that will be inserted into the central space of the support device. Generally, the prosthetic aortic valves used in conjunction with the valve support device of the present invention have an external diameter considerably less than that of the mitral valve annulus. Thus, typically, the outer diameter of the support element will be in the range of 30-50 mm, while the inner diameter will have a value in the range of 23-29 mm. It may therefore be appreciated that Rd approximately corresponds to the annular gap between the small outside-diameter replacement valve and the relatively large diameter mitral valve annulus. Thus, in one preferred embodiment, at least one of the support elements in its deployed configuration is provided in the form of a flat annular ring, wherein the difference between the outer radius and the inner radius of said annular ring is in the range of 1-20 mm. With regard to the thickness of the support element (t) (as measured along the longitudinal axis of the element when in situ), t represents a compromise between the need for minimizing this parameter in order to facilitate crimping and insertion into a delivery catheter, and the need for the support device to be sufficiently rigid such that it is able to withstand the forces exerted by the beating heart without buckling. In one typical, non-limiting example, t is 0.4 mm, while Rd has a value of 5.5 mm. Indeed, as a general rule, in most embodiments of the annular support element of the present invention, Rd is significantly larger than t. For example, in many cases Rd may be between 2.5 and 35 times larger than t, more preferably between 10 and 20 times larger than t. It may be appreciated from the foregoing explanation that the ratio between Rd and t has functional significance for the valve support device of the present invention.

As indicated hereinabove, in a preferred embodiment of the invention, the valve support device is used to assist in the implantation of a prosthetic aortic valve into the mitral valve annulus of a human subject in need of such implantation. The thickness of the at least one of the two support elements is generally in the range of 0.25-0.6 mm, more preferably 0.4 mm.

In some embodiments the bridging members and/or support elements are fitted with replacement valve engagement means adapted to securely engage a replacement heart valve. It is to be noted that the term "valve engagement means" is used herein interchangeably with the term "valve attachment means". In some embodiments, the engagement means can have anchoring and/or locking elements adapted to securely lock with a portion of a replacement heart valve. In other embodiments, the replacement valve engagement means are formed from a soft biocompatible material (such as a biocompatible fabric, silicon, PET etc.) which is fitted to the external surface of portions of the support elements and/or bridging members. In these embodiments, the soft, compressible nature of the biocompatible material permits certain portions thereof to be compressed by the struts or other structural elements of the replacement valve, upon expansion within the lumen of the valve support. Other portions of the soft biocompatible material which are not compressed by the expanded replacement valve protrude into the internal space of said valve between the struts and/or other structural elements. The protrusions formed in this way engage and grip the replacement valve thereby preventing its movement in relation to the valve support. In other embodiments, the replacement valve engagement means comprise rigid anchors of a size and shape such that they are capable of entering the internal space of the replacement valve between its struts and/or other structural elements, upon expansion of said valve within the internal space of the valve support.

Unlike in the case of the aortic valve, the pathologically-involved mitral valve is generally not associated with increased calcification. One consequence of this lack of calcification is that it is not possible to increase stabilization of the valve support device of the present invention within the mitral valve annulus by means of elements that exert their stabilizing forces in a radial direction. The reason for this is that the soft tissue of the uncalcified annulus in this situation would simply react to the applied radial forces by expanding in a radially-outward direction, thereby tending to reduce the contact between the support device and the tissue. Thus, in the case of the mitral valve, additional stabilization, if required, can only be achieved by means of stabilizing elements that apply forces on the heart tissues along the longitudinal axis. In this regard, it is to be noted that for the purposes of the present disclosure, the term 'radial' refers to the plane of the anatomical valve when the native leaflets are closed. The term 'longitudinal' refers to a direction that is at 90 degrees to the radial direction, namely approximately parallel to an imaginary line drawn from the cardiac apex to the cardiac base.

Thus, in preferred embodiments of the invention, the mechanical stability of the valve support device is enhanced by the use of stabilizing elements, wherein said stabilizing elements are adapted to apply stabilizing forces to the heart tissue in the longitudinal direction, and/or heart tissue anchoring means.

Thus, in some embodiments, the support elements and/or bridging members are fitted with heart tissue anchoring means adapted to securely anchor said support elements to the heart wall. Non-limiting examples of such anchoring means include hooks and spirals.

In some embodiments, the cardiac valve support further comprises one or more stabilizing elements, the function of which is to provide additional axial stabilization of said support within the ventricle and/or atrium. Said stabilizing elements may be attached to one or both of the support elements. Although in some cases, the stabilizing means include one or more elements that become physically attached to the cardiac tissue (e.g. in the atrial or ventricular walls), in many other embodiments, said stabilizing means provide additional mechanical stability by means of applying pressure on the inner surface cardiac wall without being physically connected to the subsurface cardiac tissues. In some embodiments, the cardiac valve support comprises one or more intra-ventricular stabilizing elements, one or more intra-atrial stabilizing elements. In other embodiments, the cardiac valve support will be fitted with at least one intra-ventricular stabilizing element and at least one intra-atrial stabilizing element.

The aforementioned stabilizing elements may be constructed in a number of different ways. Thus, for the purpose of the present invention, said stabilizing elements may be provided in the form of complete ring structures, partial rings, curved arms or wings or elongate arms or wings. Examples of all of these various types of stabilizing element will be described in more detail hereinbelow.

With regard to the aforementioned stabilizing elements that are constructed in the form of elongate arms or wings, said elongate wings may be optionally cut out of the same disc that is used to form the annular support element itself. Said wings are used to anchor and stabilize the support device in its working location, by means of applying pressure to the inner ventricular wall. In most of the preferred embodiments described herein, the valve support devices comprise only two such anchoring wings. However, certain versions of the device may possess more than two wings.

In general, the anchoring wings of this embodiment are longer than the other intra-ventricular and intra-atrial stabilizing structures disclosed hereinabove, and described in more detail hereinbelow. In many cases, this increased length of the anchoring wings is advantageous, since it allows said wings to make contact with a larger area of the ventricular wall surface, thereby resulting in improved stabilization of the support device.

In some preferred embodiments of this aspect of the invention, one or both of the annular support elements each contain only two wings, spaced apart by 180 degrees+/–a few degrees. The reason for this is that generally, the wings must be aligned along the mitral valve commissure in order to prevent hindrance of the native valve function during implantation of the replacement valve.

However, despite the need for the wings to be disposed opposite each other, most of the wing designs are asymmetric—that is, the two wings are not formed exactly opposite each other (i.e. exactly 180 degree separation), in order to avoid problems during crimping of the device prior to loading it into the delivery catheter. Rather they are arranged side-by-side when the disc is in a flat conformation (i.e. before the wings are bent downwards).

In one preferred embodiment, the above-described elongate wings are attached to one support element only, said support element being the one that in use will be the upper of the two support elements.

In some embodiments the first and second support elements are adapted to preferentially bend at at least one location.

In some embodiments the first and second support elements each have a curved portion in their deployed configurations, wherein the curved portions are adapted to assume a tighter curved configuration in the collapsed delivery configurations.

In some embodiments the first and second bridging members are generally C-shaped in their deployed configurations.

In some preferred embodiments of the present invention, the inner perimeter of one or both of the support elements is able to elastically deform in a radial direction. In this regard, it is to be appreciated that the annular shaped elastically-deformable support elements of the present invention possess an external diameter and an internal diameter. In use, a valve support element of the present invention is selected such that the replacement cardiac valve, in its fully expanded, deployed configuration, has an external diameter which is slightly larger than the inner diameter of the support elements when the latter are expanded. Then, upon deployment of the replacement valve within the internal space of the valve support elements, the internal diameter of one or both of the support elements, by virtue of their elastically-deformable nature, are increased. The replacement valve is thus held firmly in place within the valve support by means of the radially-inward forces that are exerted by the elastically-deformable portions of one or both support elements on said valve as a result of the tendency of the elastic inner surface of said support element(s) to return to its rest position.

It is to be noted that the elastically-deformable support element may be constructed such that either its entire inner surface is elastically deformable or, alternatively, it may be constructed such that only certain discrete regions thereof are elastically deformable.

In one highly preferred embodiment, the valve support of the present invention is used to enable the replacement of dysfunctional mitral valves with commercially-available aortic valves. Currently available Aortic valves which may be implanted via a trans-femoral approach or a trans-apical approach are generally made either of balloon expandable material (for example Stainless steel—such as Sapien stented valve, Edwards Inc.) or self-expanding material (for example Nitinol—such as the CoreValve stented valve, Medtronic Inc.).

In balloon expandable valves, after deployment and expansion of the valve in its position the stent of the valve has a recoil phenomenon. This means that immediately after maximal balloon expansion, when the balloon is deflated, there is some recoil, some "closing back" of the stent. This effect is a physical mechanical property of the metallic balloon expandable stent. When implanted in the Aorta, the Aortic wall is elastic, and after its expansion it applies an inward force on the stent, maintaining it in position. However, if one inflates such a stented valve in a completely rigid tube/element than immediately after expansion the stent will have some recoil, but the rigid element will not have any recoil due to its rigidity—hence there will always be some space between the stent and the rigid element, and the stent will not be held in its place by strong forces.

Self-expanding stents do not display recoil phenomena; however they present a different challenge for deployment within a valve-support. The externally directed forces applied by self-expanding stents is lower than that of balloon expandable stents, hence it is a significant challenge to ensure that a self-expanding stented valve will be deployed and secured into a valve-support, without being dislocated during the cardiac cycle. Hence there is a significant advantage if the valve support has one or more support elements which are capable of applying internally directed radial forces, which increase the forces attaching the valve to the valve support and ensure the valve will not be dislocated.

In some further preferred embodiments of the invention, at least one segment of one or both of the support elements has an external diameter that is larger than the diameter of the cardiac annulus into which said support element will be implanted (hereinafter referred to as "enlarged diameter segments" or similar), and wherein at least one other portion of said annular element has an external diameter that is smaller than the diameter of said annulus (hereinafter referred to as "reduced diameter segments" or similar). It may thus be appreciated that said reduced diameter segments interrupt the otherwise-ring shaped outer circumference of the support element of the present invention.

In one preferred embodiment of the present invention, one or both of the support elements have two enlarged diameter segments and two reduced diameter segments. In another preferred embodiment the support element comprises four enlarged diameter segments and four reduced diameter segments.

It will be appreciated that, upon implantation of the valve support of the present invention into the region of the cardiac annulus, each of the support element enlarged diameter segments will form a fluid-tight seal against the tissue of the anatomic annulus. Conversely, a small aperture will be created between each of the reduced diameter segments and the adjacent portion of the annulus, thereby permitting the limited peri-valvular flow of blood between the ventricle and atrium on the side of the heart in which said support element is implanted. In this way, the fluid pressure (and hence force) exerted by the contracting heart on the cardiac valve support (and on a replacement valve situated within said support) will be reduced. Additionally, this design reduces the afterload against which the ventricle contracts, since it allows controlled limited regurgitation, and thus may have beneficial clinical effects on ventricular function, reducing ventricular wall stress and oxygen consumption.

In one preferred embodiment of the valve support device of the present invention, the internal diameter of the upper and lower support elements is larger than the height of the device (i.e. the distance between said upper and lower support elements, and hence the length of the bridging members). Such a design is needed in order for the device to be adaptable to work with current available Transcatheter Aortic Replacement Valves. An example of such a valve is the Sapien Transcatheter Aortic Replacement Valve (Edwards Lifesciences inc. Irvine, Calif.). An exemplary expanded diameter of the Sapien valve is 26 mm, and its length is 17 mm. Hence a valve support which is appropriate for this type of Sapien valve should have an upper and lower support element inner diameter of approximately 26 mm, and its length should preferably be approximately 16-17 mm (slightly shorter than the valve, so as not to protrude from the valve and to allow the stented valve to expand and attach to both the upper and lower rings).

In the pre-expanded conformation of the valve support device having the length-to-diameter relationship described immediately hereinabove, the bridges are remote from each other—that is, they do not meet in the center of the support device—since, as described hereinabove, the length of each of said bridges is shorter than their inner diameter. Consequently, in the pre-expansion conformation, the bridges are unable to provide any guidance in order to maintain the valve support in a centered position with relation to the guidewire. This problem may be solved, however, by means of incorporating extensions, or arms, attached to the bridging members and/or support elements which allow guide wire centering throughout the deployment of the device, that is, even when the valve support is in its collapsed, delivery (pre-expansion) conformation. Said extensions have a lateral edge or end that is attached to a bridging member or support element, and a medial free end or edge, such that said free ends of two or more such extensions together form a guidance element that is capable of centering a wire that is passed through the center of the valve support device. These extensions, while being disposed sufficiently close to each other within the center of the support device, are still able to permit expansion of the valved-stent within the central space of the said support device, and, following expansion, do not bulge either inwards into the valved-stent or outwards, beyond the margins of the generally cylindrical shape of the valve support.

In one preferred embodiment of the presently-disclosed valve support device, the valve support extensions have a higher flexibility (i.e. they are less rigid) than the other elements present in either the valve support (e.g. the upper and lower support elements) or in the replacement valve. This lower rigidity allows easier insertion of a stented valve over the guide-wire and into the valve support of the invention. Since the valve diameter is larger than the wire diameter, and in some embodiments is also larger than the gap between the extensions, the insertion of the stented valve expands the extensions, moves them apart. It is therefore highly advantageous if the bridge extensions have a higher degree of elasticity.

In some embodiments the first support element has at least one coupling element adapted to reversibly couple to a delivery system. The at least one coupling element can be a threaded bore.

In a further preferred embodiment of the present invention, one or both of the first and second annular support elements are fitted with at least one wing-like drape element made of a biocompatible fabric. The drape functions as a sealing element, positioned between the support element and the mitral annulus, thereby preventing paravalvular leakage after implantation of the valve support in the mitral annulus.

In one preferred embodiment of this aspect of the invention, a single drape element is attached to the entire circumference of the support element. In another preferred embodiment, a plurality of drapes is attached to the support element. In this embodiment, the drapes may be positioned such that there is a small overlap between adjacent drapes, thereby preventing leakage therebetween. This drape sealing feature uniquely solves the problem of paravalvular leakage following implantation of the replacement valve, since the fabric drape element is capable of moving in response to force applied by the blood flowing during ventricular systole such that it seals most or all of the residual space between the support element and the mitral (or other) valve annulus.

In some embodiments the second support element has a dimension in the deployed configuration that is larger than a dimension of the first support element in the deployed configuration with or without one or more fixation elements attached and radially engaging in cardiac tissue when needed.

In some embodiments, the first and second support elements are connected by only two bridging members.

One aspect of the disclosure is a system adapted for endovascular or transapical delivery to replace a mitral valve, comprising: a cardiac valve support comprising a first support element with a collapsed delivery configuration and a deployed configuration; a second support element with a collapsed delivery configuration and a deployed configuration; at least two bridging members extending from the first support element to the second support element, said bridging members having a delivery configuration and a deployed configuration; wherein the first and second bridging members either extend radially inward from the first and second support elements in the deployed configurations, or extend longitudinally therebetween, without any appreciable radial curvature, as disclosed hereinabove; and a replacement heart valve comprising an expandable anchor and a plurality of leaflets adapted to be secured to the cardiac valve support. For the sake of clarity of description, the above disclosure relates to a system comprising a cardiac valve support in which the two support elements are connected by two bridging members. However, it is to be recognized that said system may also comprise cardiac valve supports in which more than two bridging members mutually connect the two support elements. Furthermore, the cardiac valve of the presently-disclosed system may include any of the technical features disclosed hereinabove and described in more detail hereinbelow.

In some embodiments the bridging members are adapted to securingly engage the replacement heart valve. In one such embodiment, the bridging members are formed such that at least one portion thereof comprises a series of folds or pleats (e.g. z-shaped pleats), the purpose of which is to increase the surface area of the bridging members that are available for interacting with the replacement valve. An additional benefit of this embodiment is that the pleated region also assists in the transition between the delivery (closed) conformation of the valve support device and the deployed (open) conformation thereof. In other embodiments, the replacement valve securing means comprise attachment means, such as hooks or other mechanical anchors that are connected, at one of their ends, to the support elements and/or bridging members, and have a free end for attachment to the replacement valve.

In some embodiments of the invention, the system disclosed hereinabove further comprises pressure measuring elements. These elements may be situated anywhere in the system—including on the surface of the valve support device, attached to the replacement valve, as well as within the guide catheter. In another embodiment, the system of the invention further comprises connection terminals that permit the connection of pacemaker leads to various parts of said system.

While the above-disclosed system may comprise any suitable replacement heart valve, in a particularly preferred embodiment, said valve is a prosthetic aortic valve. Examples of suitable prosthetic aortic valves include (but are not limited to) the following commercially-available replacement valves: Sapien Valve (Edwards Lifesciences Inc., US), Lotus Valve (Boston Scientific Inc., US), CoreValve (Medtronic Inc.) and DFM valve (Direct Flow Medical Inc., US).

One aspect of the disclosure is a method of replacing a patient's mitral valve, comprising the steps of: delivering a valve support to a location near a subject's mitral valve, the valve support comprising a first support element a second support element, and at least two bridging members extending from the first and second support elements; allowing the first support element to unfold from a collapsed configuration to a deployed configuration secured against cardiac tissue close to, or at, the mitral valve annulus; allowing the bridge members to unfold from their delivery configuration to deployed configuration, in a way that they become positioned in general alignment with the coaptation points of the native mitral valve leaflets; and allowing the second support element to unfold from a collapsed configuration to a deployed configuration secured against cardiac tissue in the region of the mitral valve annulus.

In the context of the present invention, the term "allowing" a support element or bridging member to unfold, generally refers to the situation wherein said support element or bridging member is retained in its compact, folded conformation by virtue of being enclosed within a delivery catheter. Then, when said catheter is withdrawn, these structures unfold and thereby adopt their deployed configuration, by virtue of their shape memory properties.

One of the key advantages of the presently-disclosed method of cardiac valve replacement is the fact that the valve support device may be implanted in the region of the anatomical valve annulus while maintaining native valve leaflet function.

In one embodiment, the above-defined method may be employed to deliver the valve support by an endovascular (e.g. transfemoral) route. In another embodiment, the method may be used to deliver the valve support by the transapical route.

In some embodiments expanding the first support element comprises allowing the first support element to self-expand against cardiac tissue.

In certain embodiments, the method further comprises the step of causing cardiac attachment means—including both cardiac anchoring elements and stabilizing elements—fitted to the support elements and/or bridging members to become into contact with cardiac tissue. In certain cases, the insertion of said attachment means is effected by means of control wires inserted through the delivery catheter which are used to cause rotation of the valve support device. In other cases, said attachment means may be covered by a sleeve during insertion of the valve support device, said sleeve being removed in order to allow said attachment means to become inserted into the ventricular wall. In still further embodiments, the attachment means may be constructed in the form of an anchor with two or more backwardly-pointing self-opening distal arms, wherein said distal arms are retained in a closed conformation by means of a resorbable suture. Then, after a certain period of time following insertion of said attachment means into the ventricular tissue (e.g. between a few hours and few weeks), said suture dissolves, thereby permitting the distal arms to adopt their open conformation.

In other embodiments, the above-defined method further comprises the step of causing intra-ventricular stabilizing elements and/or intra-atrial stabilizing elements to engage, respectively, the inner ventricular wall and/or inner atrial wall.

In some embodiments expanding each of the bridge members comprises allowing the bridge members to assume a deployed configuration in which they extend radially inward from the first and second support elements.

In some embodiments expanding the second support element against left atrial tissue comprises allowing the second support element to self-expand.

In some embodiments expanding the first support element comprises expanding the first support element towards a generally annularly shaped deployed configuration.

In some embodiments expanding the first support element comprises expanding the first support element secured against papillary muscles and chords attached to the native mitral valve, and can be done without displacing them.

In some highly preferred embodiments native leaflets continue to function after expanding the second support element.

In some embodiments expanding the first support element occurs before expanding the second support element. In certain other embodiments, expansion of the second support element occurs before expansion of the first support element.

In some embodiments expanding the bridge members comprises allowing the bridge members to symmetrically extend from the first support element to the second support element.

In some embodiments expanding the bridge members comprises allowing the bridge members to extend from the first and second support elements about 180 degrees from one another.

In some embodiments expanding the second support element comprises expanding the second support element to the deployed configuration in which the second support element has a dimension larger than a dimension of the first support element in the deployed configuration. The second support element may have one or more fixation elements adapted to pierce the cardiac tissue.

In some embodiments the method further comprises securing a replacement cardiac valve to the valve support. Securing the replacement valve to the valve support can include comprise expanding the replacement mitral valve from a collapsed delivery configuration to an expanded configuration. Expanding the replacement valve can include expanding the replacement valve with a balloon and/or allowing the replacement valve to self-expand. Securing a replacement valve to the valve support can comprise securing the replacement valve radially within the valve support. Securing a replacement valve to the valve support can comprise locking a replacement valve element with a valve support element to lock the replacement valve to the valve support. The bridge members can each comprise a bridge lock element and the replacement valve can comprise a plurality of lock elements such that the locking step comprises locking one of the plurality of lock elements with one of the bridge lock elements and locking a second of the plurality of lock elements with the other of the bridge lock elements. In other embodiments, the step of securing a replacement valve to the valve support device comprises causing valve attachment means fitted to the valve support elements and/or bridging members to engage said replacement valve.

In a further embodiment, the above-disclosed method to deliver a valve support and a prosthetic valve may combine two separate delivery approaches—one approach for the support device and a different one for the valve. The advantage of this strategy is that it significantly shortens the time delay between deployment of the valve anchor and the deployment of the prosthetic valve itself. This is important, since after deployment of the valve support there may be interference with the native mitral valve function (due to interference with the valve leaflets). One example of such an approach is the delivery of a valve support via an endovascular, trans-septal route (as described herein), while in parallel delivering the prosthetic mitral valve via a transapical or transfemoral route (as known in the art). Conversely, the valve support may be delivered by a transfemoral or transapical approach, while the replacement valve itself is delivered trans-septally. Thus, in one embodiment of the method disclosed above, the replacement valve is delivered by the same route as the valve support. In another embodiment of the method, the replacement cardiac valve and the valve support are delivered by different routes, such as the trans-septal, and transapical routes. The use of these various approaches to delivery replacement valves and other devices is well known to the skilled artisan and has been described in several publications including U.S. Pat. No. 7,753,923 and WO 2008/070797.

In a highly preferred embodiment of the method of the present invention, the replacement cardiac valve that is secured to valve support device is a prosthetic aortic valve.

For the sake of clarity of description, the above disclosure of a method for replacing a patient's mitral valve relates to a method that uses a cardiac valve support in which the two support elements are mutually connected by two bridging members. However, it is to be recognized that the endovascular delivery system of the present invention may be used to deliver cardiac valve supports containing more than two support elements and more than two bridging members.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 29A and 29B schematically depict an embodiment of the valve support in which the bridging members are fitted with a mechanism that permits the height of said support to be altered.

FIG. 30 illustrates an embodiment of the present invention in which the lower support element has an upwardly curved outer margin.

FIGS. 33A and 33B 10A-10B depict embodiments of the valve support each having a stabilizing element formed from a stent-like mesh.

DETAILED DESCRIPTION OF THE DISCLOSURE

The disclosure is generally related to cardiac valve support structures that are adapted to be implanted near or within a native cardiac valve or native valve annulus and are adapted to provide support for a replacement heart valve. The support structures are adapted to interact with a replacement heart valve to secure it in an implanted position near or within the native valve or native valve annulus. In some embodiments the support structure is adapted to be positioned near or within the mitral valve annulus, and is adapted to interact with a subsequently delivered replacement heart valve to secure said replacement valve in place to replace the function of the native mitral valve. In a particular preferred embodiment, the replacement heart valve is a prosthetic aortic valve.

The disclosure also provides for two-step endovascular implantation procedures for replacing a patient's native mitral valve. In general, a support structure is first positioned near or within a mitral valve annulus and secured in place. A replacement cardiac valve is subsequently secured to the support structure, securing the replacement valve in place near or within the annulus. By implanting the support structure and replacement valve in two steps, said replacement valve can have a lower delivery profile because it does not have to expand as much to contact native tissue due to the presence of the support structure. This eliminates the need to have a large delivery profile replacement valve as would be required if attempting to position a one-piece mitral valve implant (i.e., an implant not assembled in-vivo) within the native mitral valve.

Figure 1A:
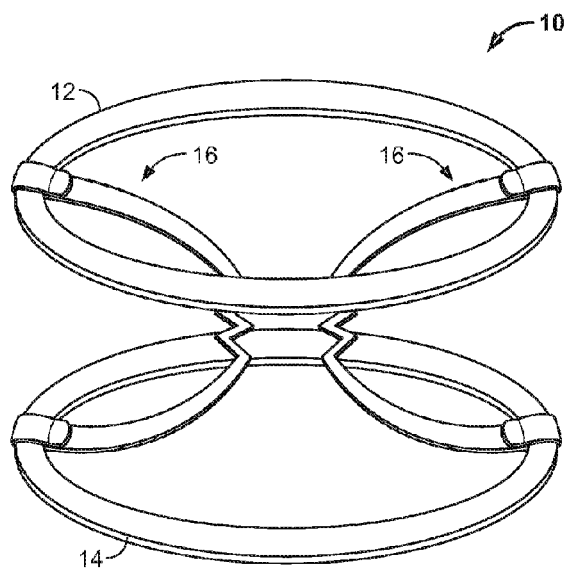
FIGS. 1A-1C illustrate an exemplary replacement cardiac valve support structure in an expanded configuration.
Figure 1B:
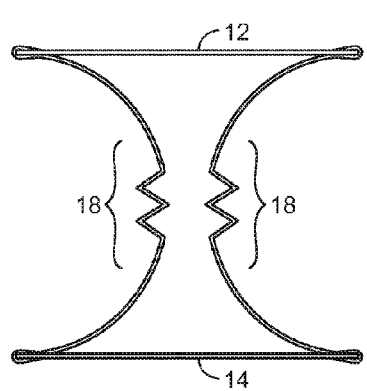
Figure 1C:
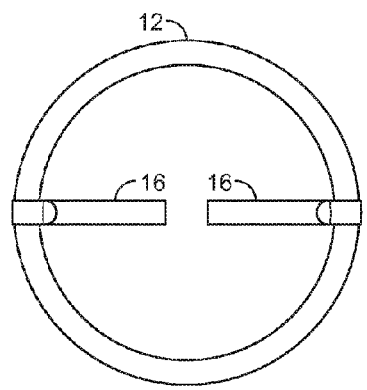

FIGS. 1A-1C illustrate an exemplary embodiment of a valve support in an expanded configuration. Valve support 10 includes a first support element 12, a second support element 14, and first and second bridge members 16 extending from first support 12 to second support 14. FIG. 1A illustrates a perspective view of valve support 10, while FIGS. 1B and 1C illustrate a side view and top-view, respectively, of valve support 10. As shown in FIG. 1B, each of bridge members 16 includes a valve engaging portion 18.

In some embodiments the first support element and the second support element are generally annular in shape in their expanded configurations (see, for example, FIG. 1A). Patient-to-patient variability in the cardiac anatomy can, however, require that the support elements have a variety of sizes and configurations. The support elements can therefore have any configuration as needed to be secured to any anatomical configuration. For example, the support elements can have generally elliptical configurations. Additionally, the support elements need not have the same general configuration. For example, the superior support element can have a generally annular shape and the inferior support element can have a generally elliptical shape. The bridge members operably connect the first and second support elements, and extend generally radially inward and axially away from a first of the support elements before extending radially outward towards the second of the support elements. For example, in the embodiment in FIGS. 1A-1C, bridge member 16 extends from support 12 in a radially inward direction and axially away from support element 12 and towards support element 14, before extending radially outward towards support 14. The valve engaging portions of the bridge members are disposed radially inward relative to the support elements. The bridge members are biased to the configurations shown in FIGS. 1A-1C, with the valve engaging portions disposed radially inward relative to the support elements. Because they are biased towards this configuration, they are adapted to apply a radially inward force to a subsequently positioned replacement cardiac valve that is expanded to an expanded configuration within the bridge members (described below). The bridge members are therefore adapted to engage the replacement heart valve to secure the replacement cardiac valve to the valve support.

In the embodiment in FIGS. 1A-1C, the bridge members extend from the support elements at discrete locations around the support elements. That is, in this embodiment, the bridge members do not extend from the support elements all the way around the support elements. If they did, the valve support would have a general hourglass shape. The bridge members, therefore, are not complete extensions of the support elements. While the embodiment in FIG. 1A-1C shows two bridge members extending from the support elements at discrete locations, the valve support may include more than two bridge members extending from the support elements at discrete locations along the support elements.

In the embodiment in FIGS. 1A-1C, the bridge members also symmetrically extend from the first and second support elements. That is, there is at least one line or plane extending through the valve that, in at least one view of the valve support, creates portions of the valve support that are symmetrical. For example, in reference to FIG. 1C, a line extending through and connecting the bridge members creates symmetrical portions of the valve support. Or, for example, in reference to FIG. 1B, a vertical line extending through the center of the valve support creates symmetrical portions of the valve support.

In some embodiments the first and second support elements and the bridge members are made from a resilient material that can be deformed into a delivery configuration yet are adapted to self-expand to an expanded configuration, with optional additional expansion of one or more components by balloon dilation. For example, the support can be made from Nitinol, relying on its superelastic properties. In some embodiments the valve support is made from a material with shape memory properties, such as nitinol, and is adapted to return to an expanded memory configuration after being heated above its transition temperature. In some embodiments in which the valve support is made from a material such as nitinol, the shape memory properties and the superelastic properties are utilized. In the embodiment in FIGS. 1A-1C, valve support 10 is adapted to return to the expanded configuration shown, either by self-expansion (relying on the superelasticity of the material), or by being heated above its transition temperature (such as by exposure to the body's temperature).

Once the support structure is expanded and secured in place within the native mitral valve, a replacement cardiac valve in a collapsed delivery configuration is advanced through the first support structure and positioned within the bridge members. Expansion of the replacement cardiac valve (e.g., balloon expansion, self-expansion, etc.) not only expands the replacement cardiac valve, but applies an expanding force on the bridge members, expanding them further radially outward towards the native annulus. Expansion of the replacement heart valve causes the replacement valve to engage the bridge members and secure the replacement cardiac valve to the valve support. Because the bridge members are biased towards a configuration in which they extend generally radially inward, the bridge members apply a radially inward force on the replacement cardiac valve, helping to secure the replacement valve in place.

Figure 9A:
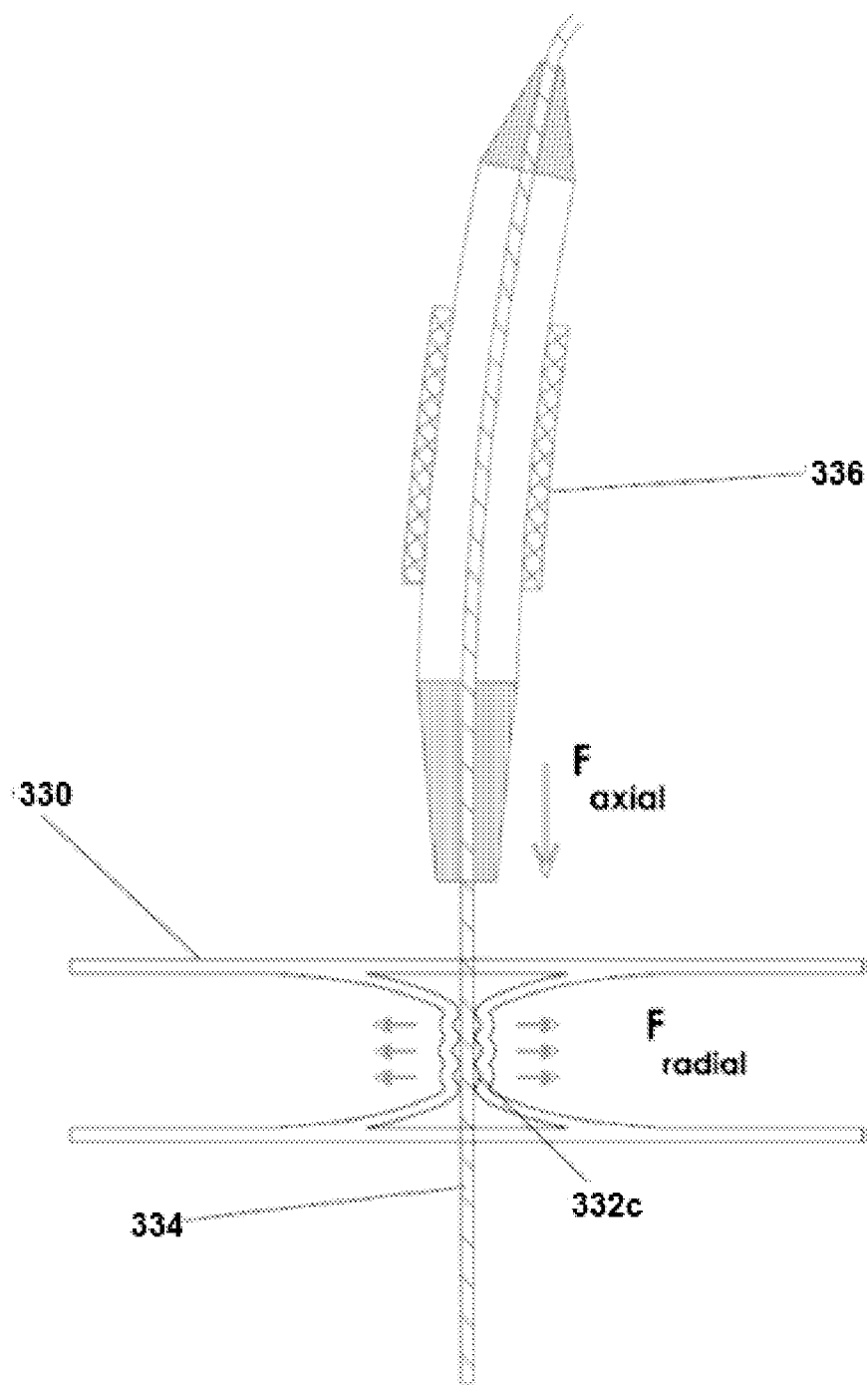
FIGS. 9A and 9B depict an embodiment of the valve support device of the present invention in which the bridging elements, in their closed conformation are disposed very close to each other in the center of said device.
Figure 9B:
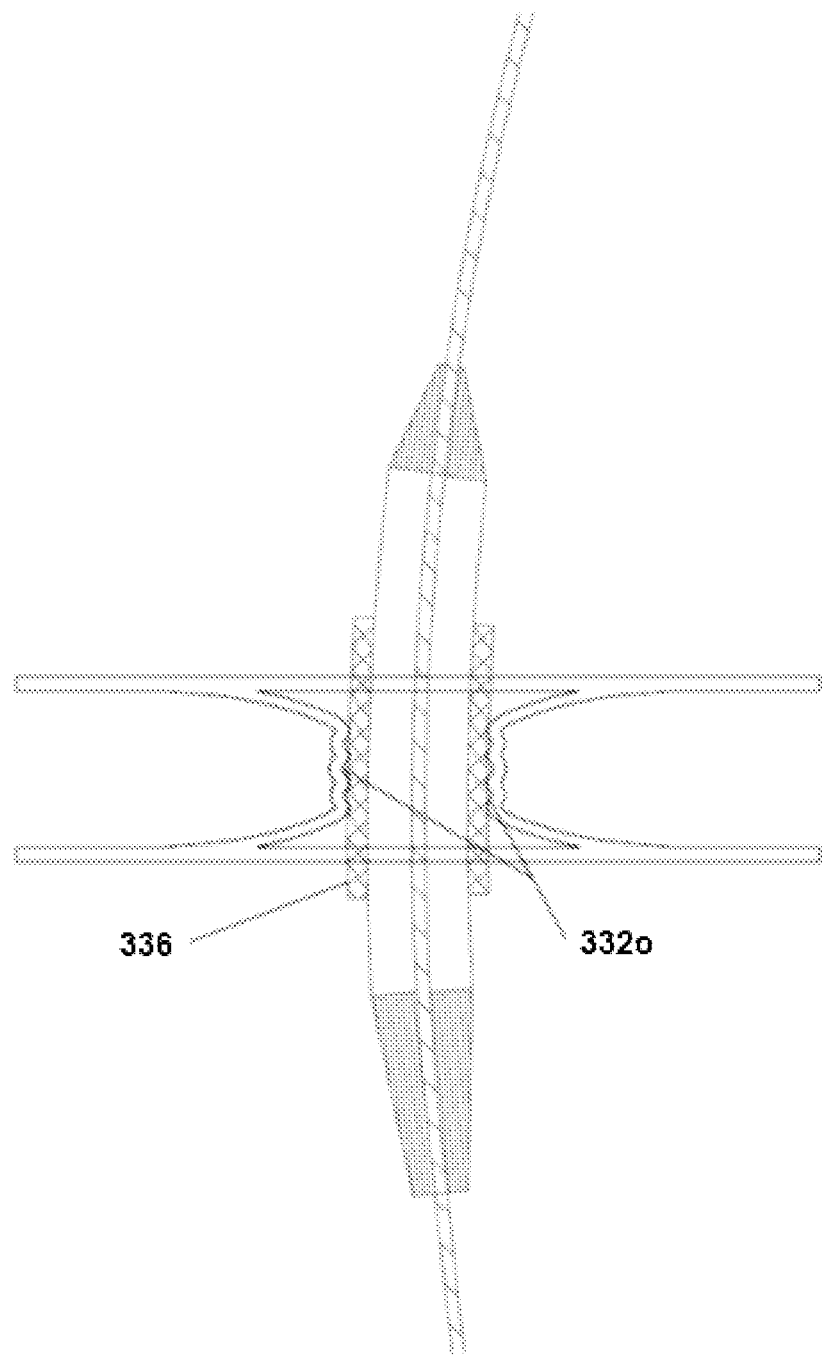

Generally, before expansion of a prosthetic valve within the support device, said device has a "closed" configuration, with the bridging members being juxtaposed to each other, thereby having a minimal distance between them (for example a distance of approximately 1-2 mm). In this closed configuration, the guide wire used to deliver the valve support (and subsequently used to deliver the replacement valve) is compressed between the two mutually apposed bridging members. In order to optimize the ability of the bridging members to compress or grasp the guide wire, the surfaces of the bridges may be non-flat, for example they may have a wavy or saw-tooth profile when viewed from the side. In one particularly preferred design, the wave or saw-tooth form will include three waves, or three teeth. However, in many cases, the bridging members may comprise fewer or more such waves or teeth. Advantageously, in this embodiment, the design of the bridging members is such that they offer minimal friction resistance to the passage of the replacement valve as it is guided axially between said bridging members towards the desired location. In this way, insertion of a replacement valve from above should cause lateral displacement of the bridging members, rather than downward displacement of the valve-support device. In order to achieve this effect, the bridging members of the valve-support are constructed from an appropriate material, such as Nitinol, Cobalt based alloys or stainless steel, and are designed in an appropriate shape to allow the transfer of force from a downward directional movement, into radial expansion of bridges. The insertion of a replacement valve over a wire in the internal space of a valve support of the present invention is illustrated in FIGS. 9A and 9B. Thus, following deployment of a valve support 330 of this type within the region of the mitral annulus, the bridging members 332c are located very close together, thereby engulfing the guide wire 334, as illustrated in FIG. 9A. Then, the replacement valve 336 is inserted over the wire, preferably via trans-septal insertion, so that the valve reaches the mitral annulus from the Left Atrium—above the location of the valve support in the annulus. Upon advancing the valve downward over the wire, it comes into contact with the juxtaposed bridging members. The design of these members is such that when the valve is further pushed downward the downward force vector applied by the valve on the bridges is diverted to a radial direction, in such a way that the bridges 332o are moved apart, "open up" and thereby permit insertion of the valve through them over the wire (as shown in FIG. 9B), until the valve reaches the required position, which is preferably at the level of the annulus, within the support device and disposed with its long axis parallel to the long axis of said support device. An advantage of this embodiment is that it ensures that the bridging members remain in contact with the replacement valve, following its implantation, without interfering with its ability to function, thereby preventing functional problems such as regurgitation.

Further details of exemplary deployment procedures are described below.

Figure 10:
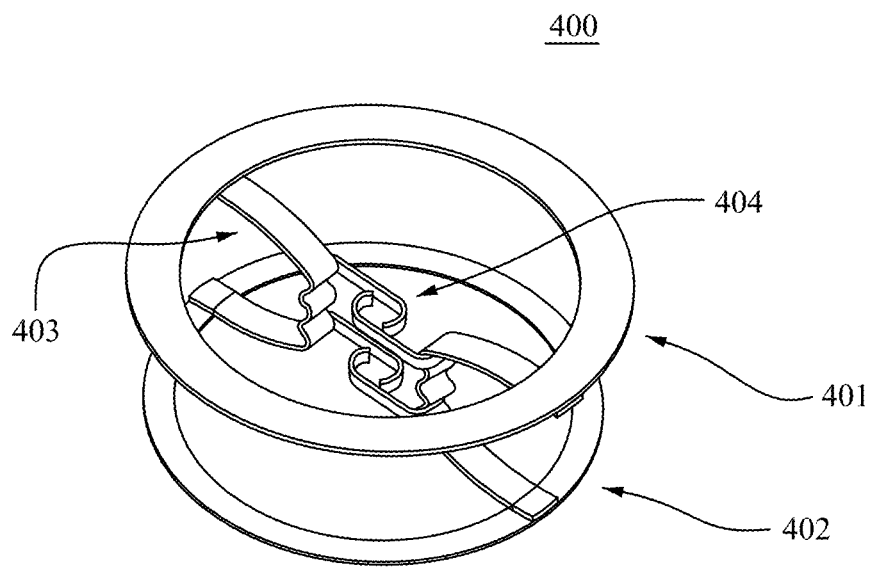
FIG. 10 illustrates an exemplary embodiment of a valve support fitted with centering means, in its expanded (unfolded) configuration.
Figure 11:
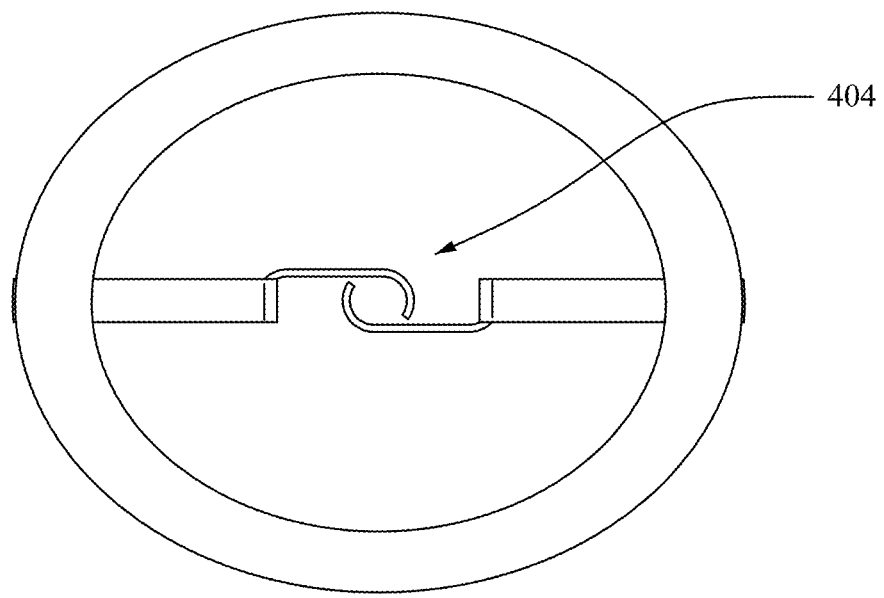
FIG. 11 illustrates another exemplary embodiment of a valve support fitted with centering means, in its expanded (unfolded) configuration.

As disclosed hereinabove, in certain preferred embodiments of the present invention, the valve support device is fitted with means for maintaining the guidewire in the center of said device throughout the deployment procedure. Details of some preferred embodiments of these centering means will now be described. Thus, FIGS. 10 and 11 illustrate an exemplary embodiment of a valve support in an expanded configuration. Valve support 400 includes a first support element (upper ring) 401, a second support element (lower ring) 402, and first and second inwardly-curved bridge members 403 extending from first support 401 to second support 402.

In the figures the bridges are illustrated as having an inwardly curved direction. However, the invention also includes bridges with a minimal inward curve (for example: 0.1 mm-2 mm inwardly direction) or with no inward curve.

FIG. 10 provides a perspective view of valve support 400, while FIG. 11 illustrates a top-view of the same device. As shown in FIG. 10, each of the bridge members 403 includes an internally oriented extension 404, constructed in such a way that each pair of extensions forms a guidance loop that is capable of surrounding a centrally-placed guide-wire. While the guidance loops so formed are incomplete loops with small gaps being located between the bridge extensions on each side, these small gaps are smaller than the diameter of the guide-wire, thus preventing it "escaping" from the confines of the guidance loops. In other preferred embodiments of this device (not shown in the figures), the bridge extensions are overlapping (such that one is larger than the other, with a slightly larger diameter), so that there is no gap between them at all. The advantage of such a design is that it reduces the chances of the guidewire "escaping" from the confines of the loops.

The extensions 404 are built so that upon expansion of the stented replacement valve within the valve support the extensions are expanded with the movement of the expanded valve, and at the end of said expansion each extension is exactly at the imaginary cylindrical border of the valve support, and does not bulge into the stented valve or out from the cylindrical border of the valve support. The illustration includes four extensions 404, two from each bridge. The scope of this invention, however, is not limited to this number alone, and includes support devices having any number of extensions that are necessary to achieve the desired goal (i.e. centering the device around the guidewire), and coming from either direction of the bridges. The advantage of having more than one extension from each bridge is that it improved the stabilization of the guidewire within the gap between the extensions, as shown from a top view in FIG. 11.

In a preferred embodiment of the device the extensions 404 (also referred to as "centering elements") have a different elasticity (different rigidity) than the support elements (rings) 401 and 402, and may also have a different elasticity/rigidity than the bridge elements 403. Preferably the extensions 404 have a higher flexibility (i.e., they are less rigid) than the other device elements. This lower rigidity allows easier insertion of a stented valve over the guide-wire and into the valve support of the invention. Since the valve diameter is larger than the wire diameter, and in some embodiments is also larger than the gap between the extensions, the insertion of the stented valve expands the extensions, moves them apart, and it is thus advantageous for them to have a higher elasticity than the other elements from which the presently-disclosed device is constructed.

Figure 12:
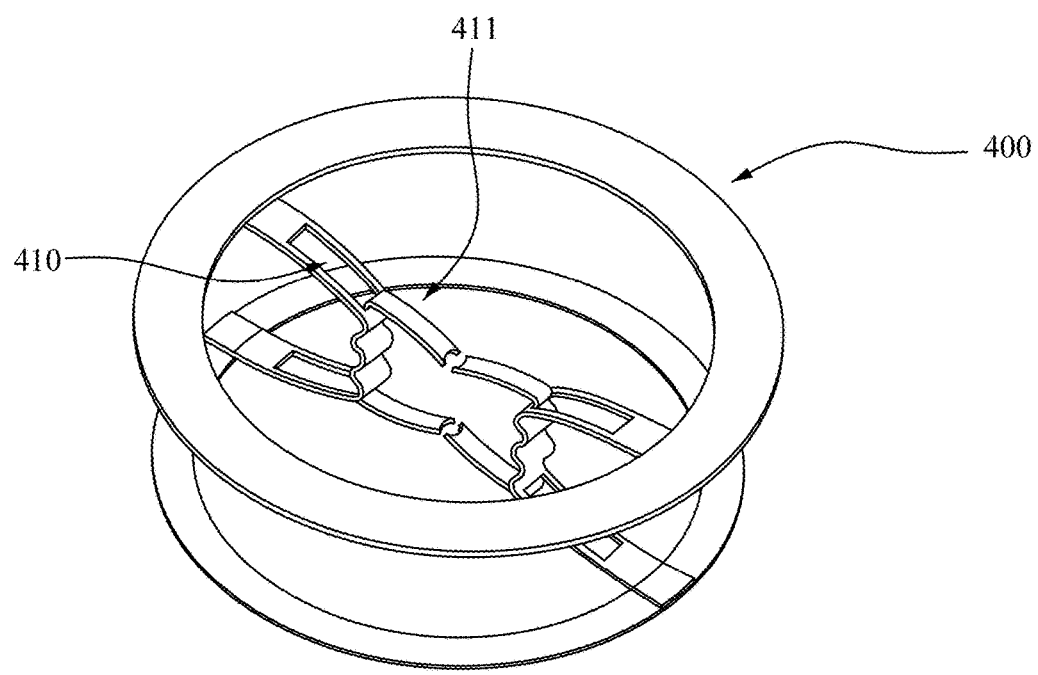
FIG. 12 depicts another embodiment of a valve support device of the invention that is fitted with guide-wire enclosing extensions.
Figure 13:
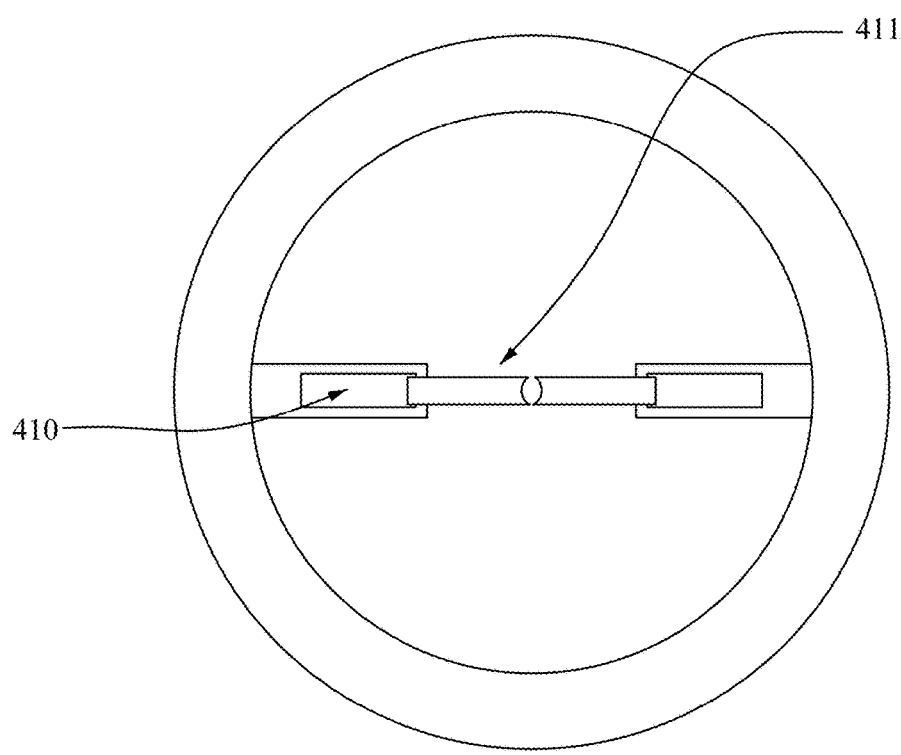
FIG. 13 presents a plan view of the embodiment of the device shown in FIG. 12.

FIG. 12 presents another embodiment of the valve support device of the present invention, 400, in which the guide-wire enclosing extensions 411 are formed from strips which have been incompletely cut-out from the bridges and then bent medially, as shown in the figure. In this way, a "window" 410, corresponding to the material bent medially to create the extensions 411, is formed within each bridge. This embodiment may be manufactured, for example, by laser cutting. One advantage of this cutout design is that it allows a simple and cost-effective manufacturing process. A further advantage is that during valve expansion within the valve support, the extension is pushed laterally—that is, expanded back into its original position within the bridge, thus ensuring that the after valve expansion the extension is exactly within the cylindrical border of the valve support and does not bulge into the valve or out of the border of the support. The complementary size and shape of the extensions 411 and the windows 410 are clearly illustrated in the top view of this embodiment that is presented in FIG. 13

Figure 14:
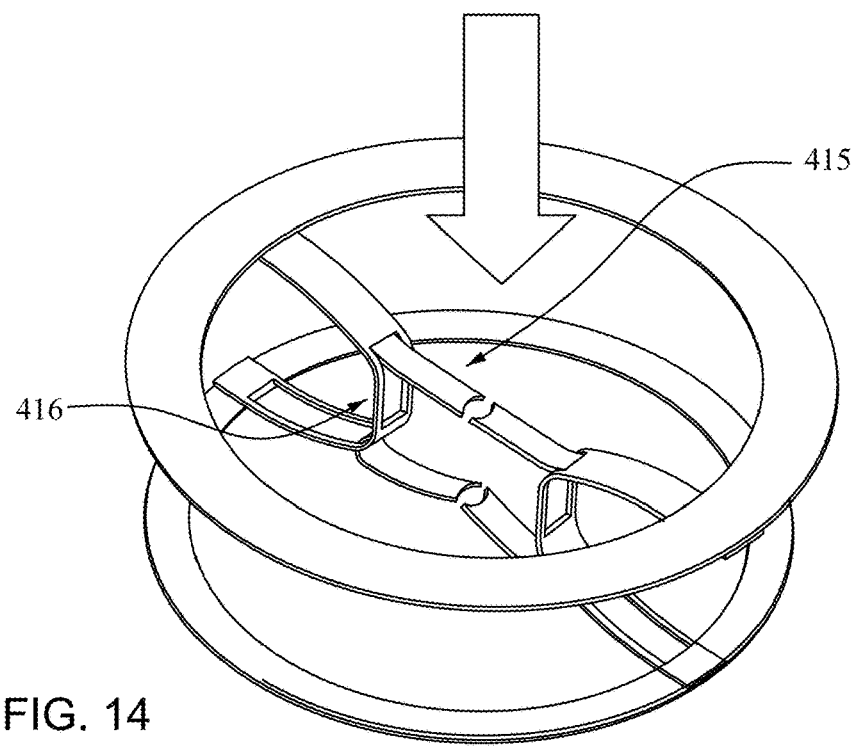
FIG. 14 illustrates, in perspective view, a further embodiment of the centering means of the present invention.
Figure 15:
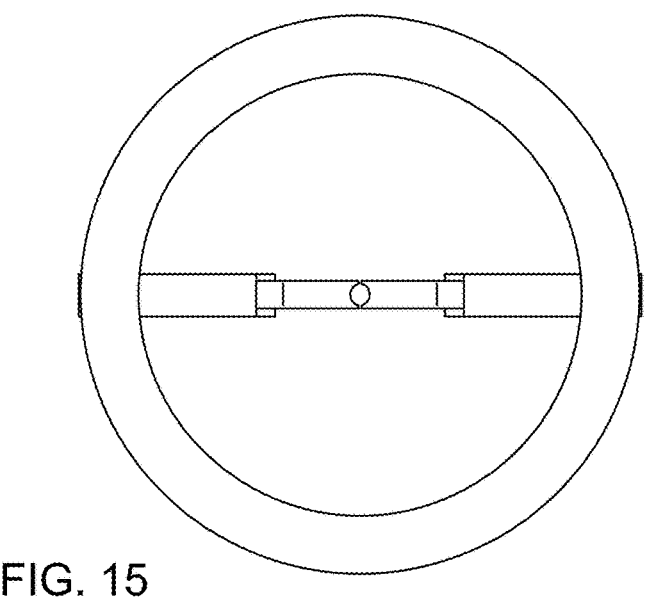
FIG. 15 presents a plan view of the embodiment of the device shown in FIG. 14.

FIGS. 14 and 15 present another embodiment of the invention, in which the guide-wire enclosing extensions 415 are made from a cut-out design out of the bridges. The free lateral edge of the partially cut-out bridge (which becomes the medial edge of extension 415) is further cut such that it is arcuate or semi-circular in shape. In this way, the arcuate free edge of each pair of bridge extensions 415 forms an incomplete guidance loop in the center of the expanded support device, as shown in FIGS. 14 and 15. As in the embodiment shown in FIGS. 12 and 13, the cut-out bridge extension leaves a "window" 416 within the bridge. The advantage of this design is the relative direction between the extension and the "window": Thus, during insertion of the stented replacement valve into the central space of the support device, the bridge extensions 415 are able to bend in the required direction (in response to the forces exerted by the inserted stented valve), depending on whether the valve is inserted from the superior (basal) side or the inferior (apical) side of the annulus. For example, for the support device illustrated in FIG. 14, if said device is deployed in a mitral annulus, and the replacement valve is delivered via a trans-septal approach, then the direction of insertion of the valve into the valve-support is from above, as shown in the arrow in FIG. 14. When the valve is inserted in this direction it causes the cut-out extensions 415 to move downwards towards the "window", and when the valve is expanded this movement is continued until the cut-out returns exactly to its original location within the bridge, and thus after deployment the extension does not bulge into the valved stent or out of the frame of the valve support. This direction is an example only, and the same concept may be used for trans-apical approach, where the direction would be exactly opposite (upward insertion of valve into valve support), and the cut-out and "window" can be designed in exactly the opposite direction from the one illustrated in FIG. 14. A top view of this embodiment is shown in FIG. 15.

Figure 16:
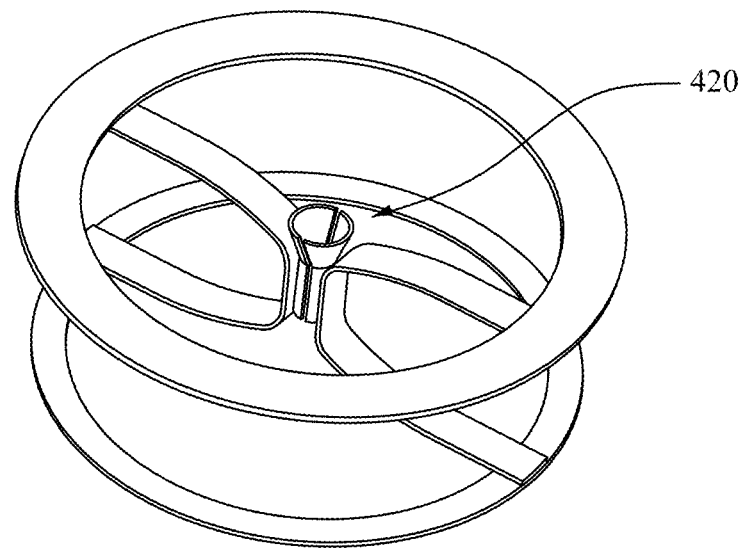
FIG. 16 illustrates yet another embodiment of the centering means of the present invention, wherein said means are provided in the form of a funnel shaped element.

FIG. 16 presents another embodiment of the invention, in which the guide-wire enclosing extensions 420 form a generally funnel shaped guidance element within the center of the support device. The advantage of the funnel shape is that it surrounds and encloses a relatively long portion of the guide wire and thus ensures its centralization, thereby reducing the chances of the wire slipping out of the central area. The funnel shape 421 shown in FIG. 17 is larger than that shown in the embodiment illustrated in FIG. 16, thereby enabling easier introduction of the stented valve into the central area (i.e. into the funnel), since the diameter of the replacement valve is larger than the diameter of the wire.

Figure 17:
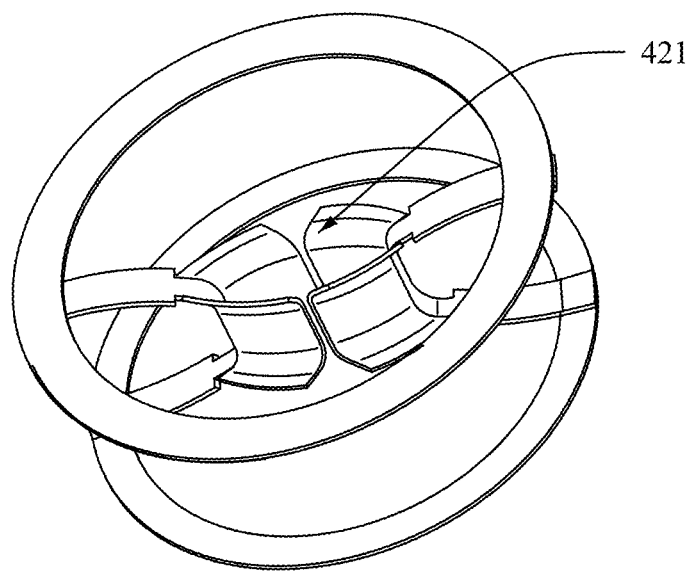
FIG. 17 shows an embodiment of the centering means that is similar to that of FIG. 16, but wherein the funnel element is significantly larger.

In both FIGS. 16 and 17 the funnel shaped extensions are approximated to each other, with a gap between them that should be smaller than the diameter of the guidewire, in order to prevent it from "escaping" from the funnel. As previously explained, in a preferred embodiment the funnel shaped expansions are designed such that one extension overlaps the other (since it is slightly longer, with slightly larger diameter), so there is no gap between them, thus minimizing the chances of guidewire "escaping" from the funnel.

Figure 18:
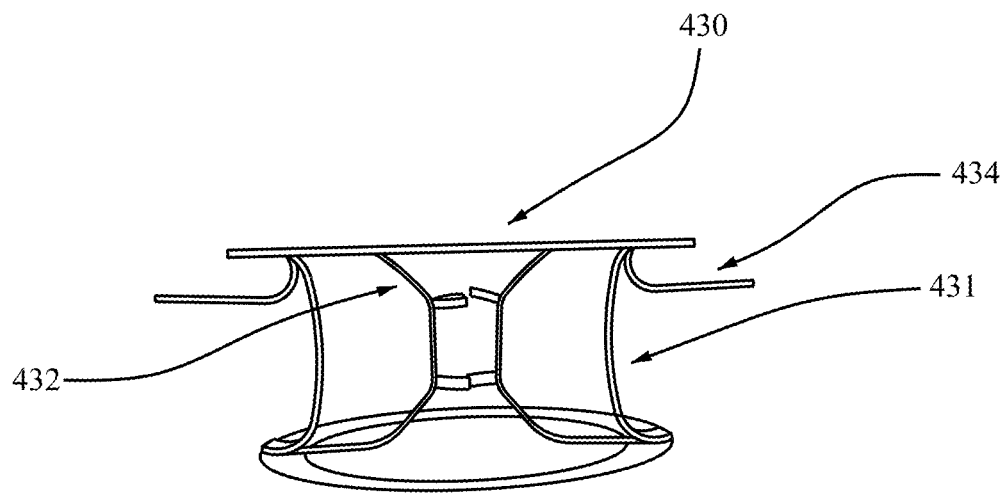
FIG. 18 is a photograph showing the side view of an embodiment of the invention in which the centering elements are separate from the bridging members.
Figure 19:
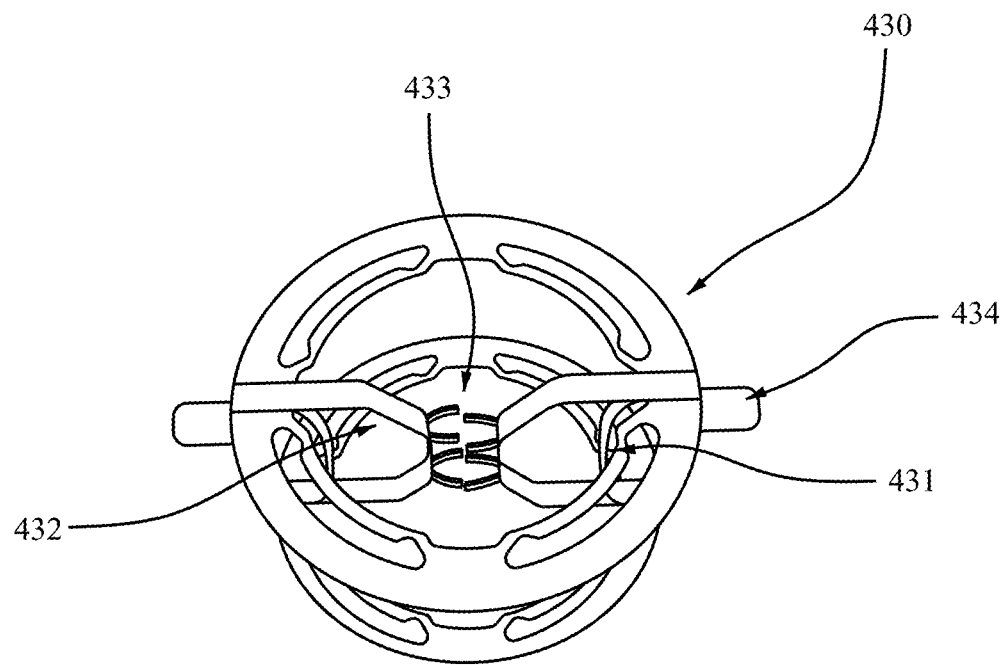
FIG. 19 presents a photographic top view of the embodiment shown in FIG. 18.

FIG. 18 (side view) and FIG. 19 (top view) are photographs of a device of the invention in which the centering extensions are separate from the bridging members. The upper ring is shown as 430. The right bridging member is shown as 431. The centering means extensions 432 do not extend from the bridges, but are separate extensions from the upper ring. The centering extensions may be extended from the upper or lower ring only, or from both upper and lower rings, as shown in this case. At the medial side of the centering extensions there are semi-circular extensions 433 which center the guidewire and prevent it from "escaping". Additionally shown in the photos are stabilizing/anchoring means 434.

Figure 20:
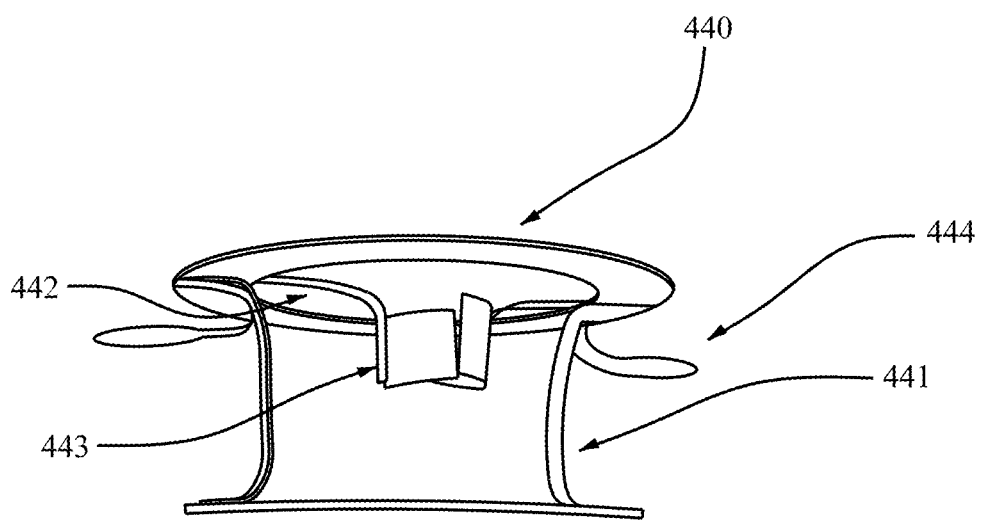
FIG. 20 is a side view of a further embodiment, in which the centering means are attached to the upper support element only.
Figure 21:
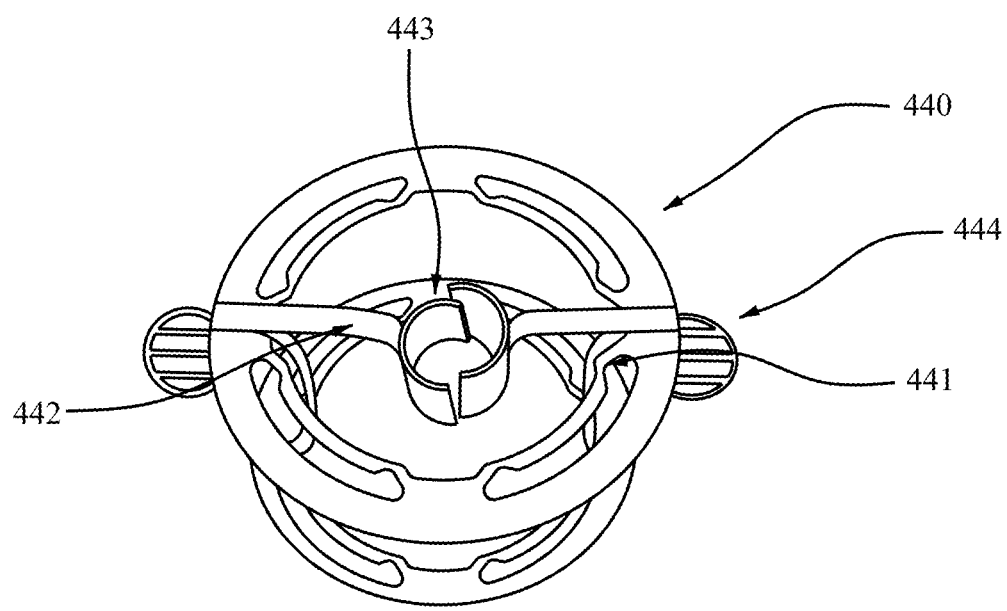
FIG. 21 presents a top view of the embodiment of FIG. 20.

FIG. 20 (side view) and FIG. 21 (top view) are photographs of another embodiment of the invention, in which the centering extensions are separate from the bridging members and in which a funnel shape centering means extends from two separate arm-like extensions stemming from the upper ring. Upper ring is shown as 440. The right bridging member is shown as 441. In this preferred embodiment the centering means extensions 442 do not extend from the bridges, but are separate extensions from the upper ring. In other designs included in the scope of the invention, the centering extensions may be extended from the lower ring only, or from both upper and lower rings. At the medial side of the centering extensions there are semi-circular extensions 443 which form a funnel shape and center the guidewire and prevent it from "escaping". Additionally shown in the photos are stabilizing/anchoring means 444.

Figure 22:
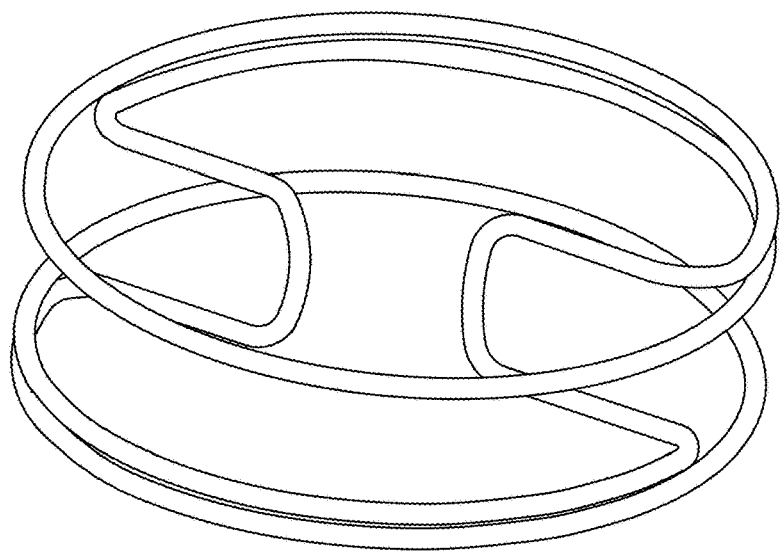
FIG. 22 illustrates a valve support device constructed form a single wire.

In the embodiment shown in FIGS. 1A-1C, the bridge members and support elements are separate and distinct elements secured to one another by any suitable technique (e.g., soldering). In some alternative embodiments, the support elements and the bridge members are manufactured as a single unit without components that need to be secured to one another (see, for example, the exemplary embodiments in FIGS. 3A-7 below). For example, in some embodiments the manufacturing of the valve support is simplified because it is manufactured from a single tubular shape memory material (such as Nitinol) that is pre-formed with predetermined expansion ratios and forces needed to retain the replacement cardiac valve in place. In some preferred embodiments of this type, the valve-support device is constructed of a single wire that has been shaped in a way to construct an upper support element, a lower support element, and two or more bridging elements between them. An example of an embodiment of this type is illustrated in FIG. 22. Suitable wire materials that may be used to manufacture valve supports of this type include (but are not limited to) biocompatible metals and metal alloys, Nitinol, cobalt and stainless steel. One advantage of this design is the fact that its simplicity of construction results in low manufacturing costs. A further significant advantage of the use of a single wire (rather than a broader strip—as depicted in FIG. 1A) is that it may be collapsed to a very small size such that it may be inserted into a small diameter delivery catheter, thereby presenting a reduced crossing profile.

Figure 23:
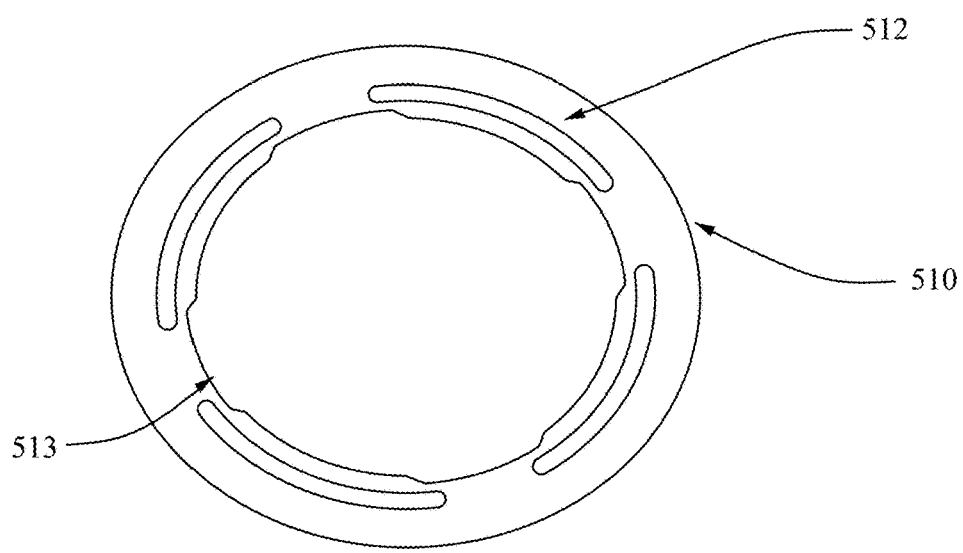
FIG. 23 depicts one embodiment of a support element of the present invention having an elastically deformable inner perimeter.

As indicated hereinabove, in some preferred embodiments of the valve support device of the present invention, one or both of the support elements may be constructed such that the inner surface or perimeter thereof is elastically deformable in a radial direction. A support element constructed in this manner is thereby able to exert radially-directed forces onto a replacement valve inserted into the central space of the valve support device. Thus, FIG. 23 illustrates an exemplary embodiment of a support element of a valve support of the invention. Support element 510 is ring shaped, and may represent the lower ring or upper ring or both rings of a two-ring valve support of the invention. The shape of the ring illustrated in FIG. 23 is circular; however any shape that is appropriate to be implanted in the annulus of the heart (for example elliptic or rectangular) is included within the scope of the present invention. In the preferred embodiment illustrated in FIG. 23 the support element 510 includes cut-out areas 512, which are cut out from the central area of the element (from the "body" of the ring), and cut-out areas 513 which are cut out from the inner part of the element (from the internal perimeter of the ring). In this example, there are four such 512 cut-out areas and 4 such 513 cut-out areas. The number and shape of these cut-out areas is exemplary only, and any number and shapes may be used. An exemplary material for manufacturing the support element is biocompatible metal or alloy (for example Nitinol or stainless steel). The goal of both cut out areas 512 and 513 is to make the support element elastically deformable at the inner perimeter of the ring, to enable radially inward forces to be applied when a stented valve is expanded within the support element.

Exemplary sizes for the device of the invention: for example, the internal diameter of the support element 510 in a "resting" state (the baseline stent, after the ring is deployed in the Mitral annulus, but before a stented valve is deployed and expanded within the ring) may be 25 mm. An exemplary valve is now expanded within the support element, the Sapien 26 mm, it is Balloon expandable, and the balloon inflates it to 27 mm, and immediately after expansion it has some recoil to a diameter of 26 mm. Since the valve was expanded within the support element, the internal ring diameter is now (after expansion) directly approximated to the valve, so the inner diameter of the support element ring is now 26 mm. Since, as said in the example, the resting diameter of the support element is 25 mm, than due to the elastic ability of the support element in the design of this invention, the support element now applies a radially inward force on the valve, and thus is strongly secured to the valve and prevents the valve from dislocating. Of course, sizing may change according to the desired valve, and this is an example only.

Figure 24:
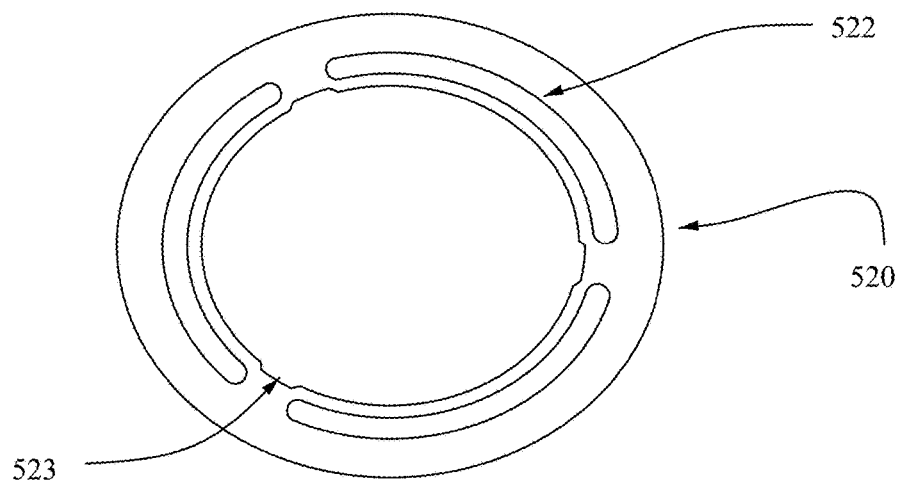
FIG. 24 illustrates a further embodiment of a support element of the present invention having an elastically deformable inner perimeter.

FIG. 24 illustrates another exemplary embodiment of a valve support of the invention. Support element 520 is ring shaped, and may represent the lower ring or upper ring or both rings of a valve support of the invention. In the preferred embodiment illustrated in FIG. 24 the support element 520 includes three cut-out areas 522, which are cut out from the central area of the element (from the "body" of the ring), and three cut-out areas 523 which are cut out from the inner part of the element (from the internal perimeter of the ring). The number and shape of these cut-out areas is exemplary only, and any number and shapes may be used.

Figure 25:
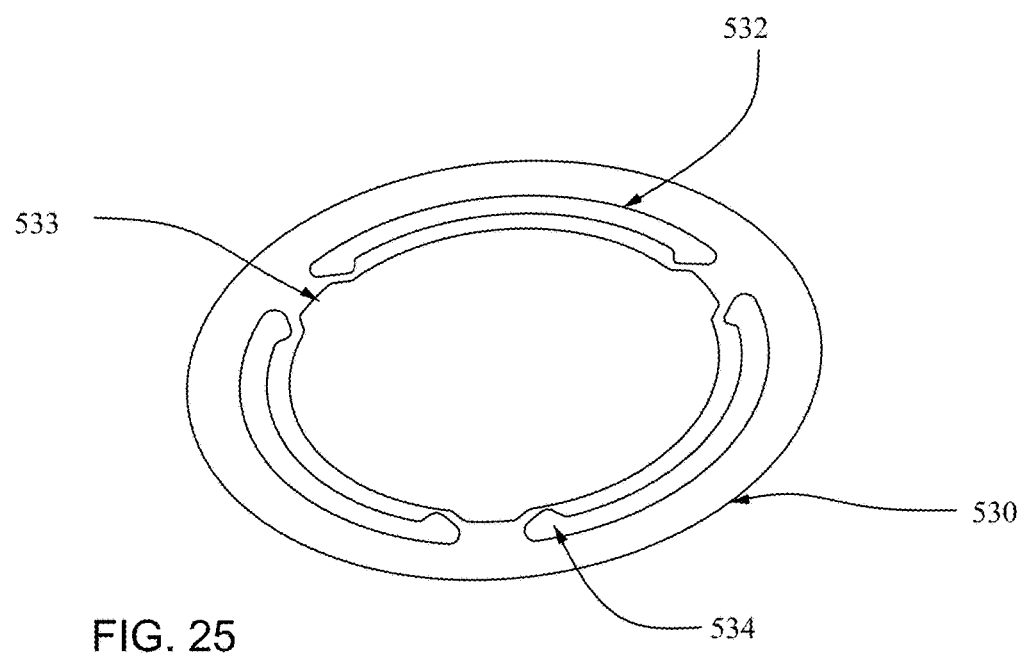
FIG. 25 shows yet another exemplary embodiment of a support element having an elastically deformable inner surface.

FIG. 25 illustrates another exemplary embodiment of a support element of a valve support of the invention. Support element 530 is ring shaped, and may represent the lower ring or upper ring or both rings of the valve support of the invention. In the preferred embodiment illustrated in FIG. 25 the support element 530 includes three cut-out areas 532, which are cut out from the central area of the element (from the "body" of the ring), and three cut-out areas 533 which are cut out from the inner part of the element (from the internal perimeter of the ring). The number and shape of these cut-out areas is exemplary only, and any number and shapes may be used. In this embodiment, each cut-out area 532 includes additional cut out areas 534 which modify and increase the elasticity of the support element. Any number or shapes of such additional cut-out areas are within the scope of this invention.

In some preferred embodiments of the invention, one or both of the support elements contain 'cut-out' areas in their outer perimeter, thereby permitting limited paravalvular blood flow (i.e. between the ventricle and the atrium) as a means of reducing the forces exerted by the contracting heart on the support device, and additionally reducing the afterload against which the ventricle contracts. In these embodiments, the shape of the upper support element (upper ring) does not completely cover the rim of the annulus and does not have a smooth shape, but rather has an outline shape that permits two things in parallel:

1—A part of the support element has a larger diameter than the annulus diameter (i.e. an expanded diameter segment), thus when the support structure is expanded above the annulus—the larger diameter of the shape prevents it from "falling down" across the annulus from the atrium into the left ventricle, and thus assists in maintaining the valve support in its intended location in the mitral annulus.

2—One or more parts of the support element have a smaller diameter than the annulus diameter (i.e. a reduced diameter segment), thus when said support element is expanded above the annulus, there are one or more apertures that remain "open" between the atrium and the ventricle. This actually causes a leak, or essentially a controlled "MR" (Mitral Regurgitation), the magnitude of which is pre-determined by the size and number of the apertures.

Clinical Theoretical Explanation:

It is pertinent at this point to explain how the intentional production of a "controlled MR" may be clinically logical for a patient who is being treated with valve-replacement to correct his pre-existing MR. Thus, patients undergoing valve replacement for MR usually suffer from grade 3 or 4 MR, which results in significant clinical symptoms thereby necessitating clinical intervention. Optimally, the goal is to replace the valve and reach zero MR (no leak). However, it is clinically acceptable to complete a procedure such that the patient remains with a small residual MR (grade 1), since it would still be significantly better than stage 4 before the procedure, and since the device of this invention allows a trans-catheter implantation instead of surgery for valve replacement, the "cost" in outcome would be stage 1 MR (with a minimally-invasive procedure) instead of zero MR (using a surgical approach), this would be clinically beneficial for some patients, especially those having co-morbidities associated with a very high surgical risk.

An additional advantage of this embodiment, in which the apertures between each of the reduced diameter segments and the adjacent portion of the annulus permit the limited para-valvular flow of blood between the ventricle and the atrium, is that after implantation of the valve support there is maintained a "controlled" or "limited" amount of regurgitation (flow during systole from the ventricle into the atria through the perivalvular apertures). This reduces the afterload, the force against which the left ventricle (LV) contracts, and may be advantageous in cases of reduced systolic performance of the left ventricle. Such afterload reduction may potentially be beneficial to improve left ventricular performance, reduce LV wall stress and oxygen consumption.

For an exemplary mitral annulus diameter of 35 mm. the inner diameter of the upper support element (upper ring) has to be appropriate for the expanded diameter of the stented replacement valve which is to be expanded in the valve support. For an exemplary Sapien 26 mm valve, the inner diameter of the upper support element is approximately 26 mm. The outer diameter of the support element should be larger than the annulus diameter, in order to prevent the device from "falling" into the ventricle, and in order to assist in prevention of para-valvular leak. Hence for this example an outer diameter of 37 mm is selected. However, at least one part of said upper support element will have a diameter which is smaller than 35 mm (for example a cut-out is made in a part of the outer perimeter of the ring, making it have a diameter of only 33 mm)—thus causing a small aperture between the outer edge of the upper ring and the mitral annulus. During systolic ventricular contraction these one or more apertures function as a pressure release mechanism— they release some of the pressure (upward force) applied on the valve support-valve apparatus, and thus reduce the risk that the apparatus will be dislocated out of position.

We now turn our attention to the accompanying figures which illustrate the salient points of the presently-disclosed embodiment.

Figure 26:
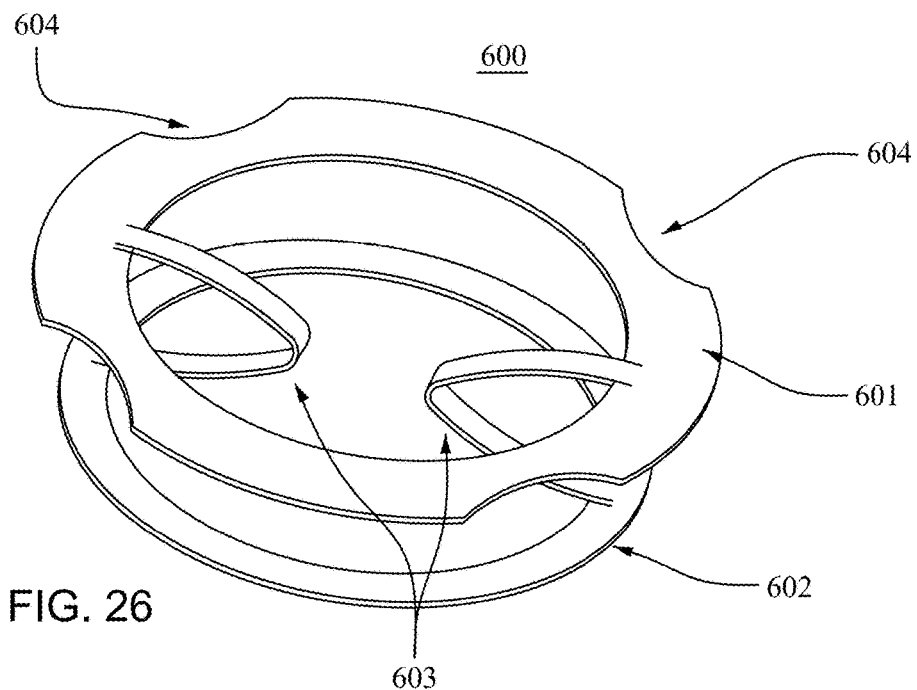
FIG. 26 provides a perspective view of one embodiment of a valve support of the present invention having four cut-out areas in its outer perimeter.

Thus, FIG. 26 provides a perspective view of an exemplary embodiment of a valve support of the present invention in an expanded configuration. Valve support 600 includes a first support element (upper ring) 601, a second support element (lower ring) 602, and first and second bridge members 603 extending from first support 601 to second support 602. As seen in this figure, the upper ring 601 has four areas of smaller diameter (cut-out areas from the outer perimeter of the ring) which are numbered as 604. The number of such smaller diameter areas 604 is given by way of example only, and the shape and size of each such area 604 is also only an example. The present invention includes any shape and size which may be deemed clinically relevant.

Figure 27:
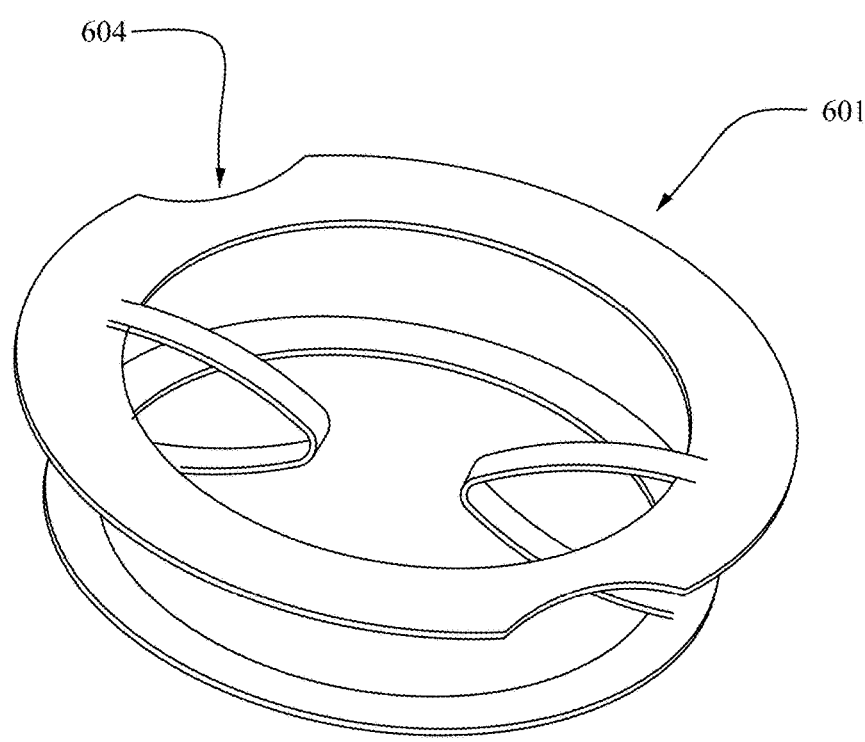
FIG. 27 provides a view of a similar embodiment to that shown in FIG. 26, but which has only two cut-out areas in its outer perimeter.

FIG. 27 presents a perspective view of another example of this invention, in which only two reduced diameter areas 604 are illustrated on the upper ring 601 of the valve support device.

Figure 28A:
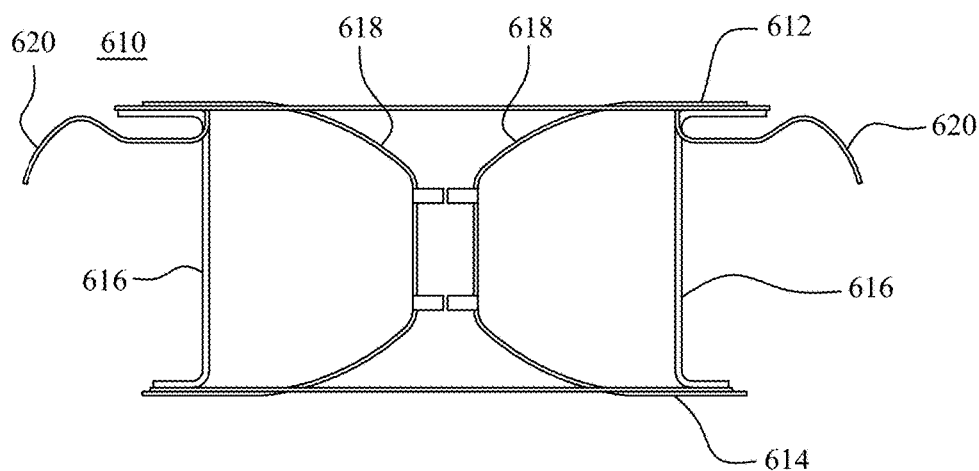
FIGS. 28A and 28B provide, respectively, a side view and a perspective view of a valve support fitted with straight bridging members.
Figure 28B:
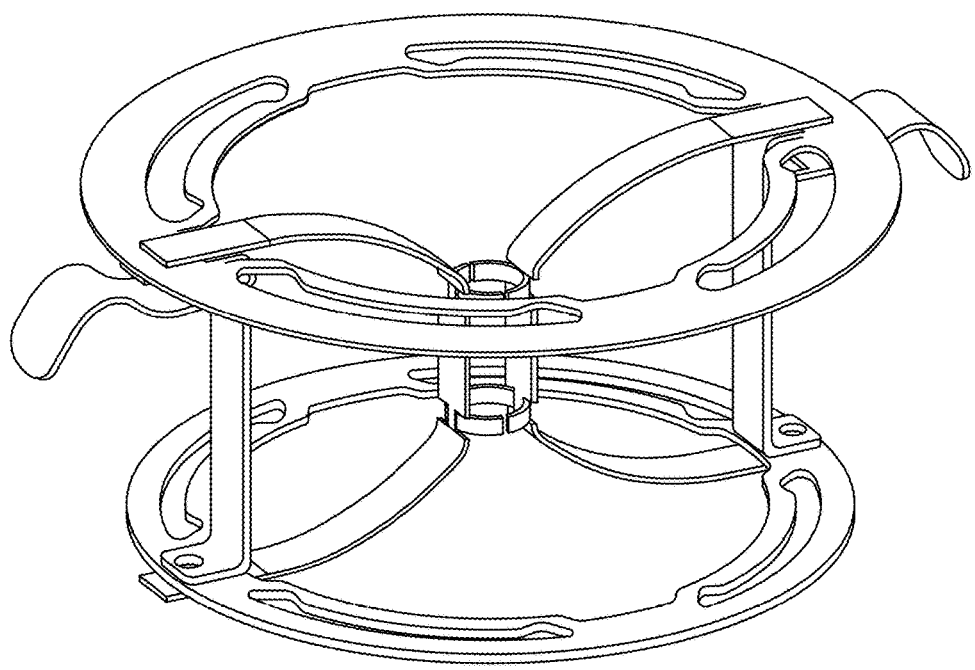

In some embodiments of the valve support device of the present invention, the bridging elements—of which there may be two or more—may be entirely straight (rather than curved radially inwards towards the center of the device). This embodiment is depicted in FIGS. 28A-28B, which illustrate an exemplary embodiment of a valve support fitted with straight bridging members in an expanded configuration. Valve support 610 includes a first support element 612, a second support element 614, and first and second bridge members 616 extending from first support 612 to second support 614. FIG. 28A illustrates a side view of valve support 10, while FIG. 28B illustrates a perspective view of valve support 610. Also seen in this figure is a pair of support extensions 618 which extend medially from the upper and lower support elements, forming guidewire centering means (as described in more detail hereinabove) in the middle of the internal space of the support device.

In some embodiments the height of the valve support, measured from the base of the first support to the top of the second support, is about 1 cm to about 5 cm to be able to accommodate the height of the replacement heart valve, such as a stented heart valve. In some embodiments the height is greater than 5 cm. In some embodiments the height of the valve support is between about 1 cm and about 2.5 cm. For example, a stented heart valve in an expanded configuration can have a height of about 17.5 mm. As explained hereinabove, the outer diameter of each support element is generally in the range of 30-50 mm, while the inner diameter thereof is generally in the range of 23-29 mm. The thickness of the valve supports is generally in the range of 0.25-0.6 mm, more preferably 0.4 mm. It should be noted, of course, that these numbers are merely exemplary and are not limiting in any way.

In one embodiment, as shown in FIG. 29, the bridging members 638 of the valve-support device are fitted with a mechanism 640 that permits the height of the device (i.e. the distance between the upper and lower support elements) to be changed: either lengthened, or (as shown in FIG. 29) shortened. In FIG. 29A, the valve support is shown at its initial height, while FIG. 29B illustrates the same support following height reduction. Suitable mechanisms include a rotatable screw element, the length of which may be altered (shortened or lengthened) by means of rotating a control wire connected to one end of said element. In an alternative implementation, a pulling-mechanism—for example, a hypotube fitted with an internal pulling wire—is arranged such that when the operator pulls said wire, only the distal part of the bridging member is pulled, thereby causing the bridging member to become shortened, thereby decreasing the overall height of the valve support device.

In some embodiments, the height of the valve support is less than the height of the replacement heart valve. These numbers are merely exemplary and are not limiting. Additionally, the two annular support elements can have different dimensions. For example, the two support elements, if generally annular-shaped, can have different diameters. In some embodiments the first support element has a larger diameter than the second support element because the anatomical position in which it is to be placed is larger than the anatomical position in which the second support element is to be placed. In the embodiment shown in FIGS. 1A-1C, support element 12 can have a larger diameter than support element 14 due to its expansion in the larger left atrium versus the smaller left ventricle, the papillary tendons and muscles, and other supporting structures in the left ventricle. The possible differences in dimensions of the superior and inferior support elements are discussed in more detail below.

In other embodiments, the lower support element of the presently-disclosed valve support device has a curved or cambered outer edge. An example of such an embodiment is shown in FIG. 30 in which the outer margins 658 of the lower support element 660 are seen to curve upwards. This type of embodiment is of particular value when the anatomical structure and size of the left ventricle is such that the valve support device may interfere with the normal ejection of blood from said ventricle through the aortic valve during systole, for example by deflecting a portion of the blood away from the aortic valve.

Figure 31:
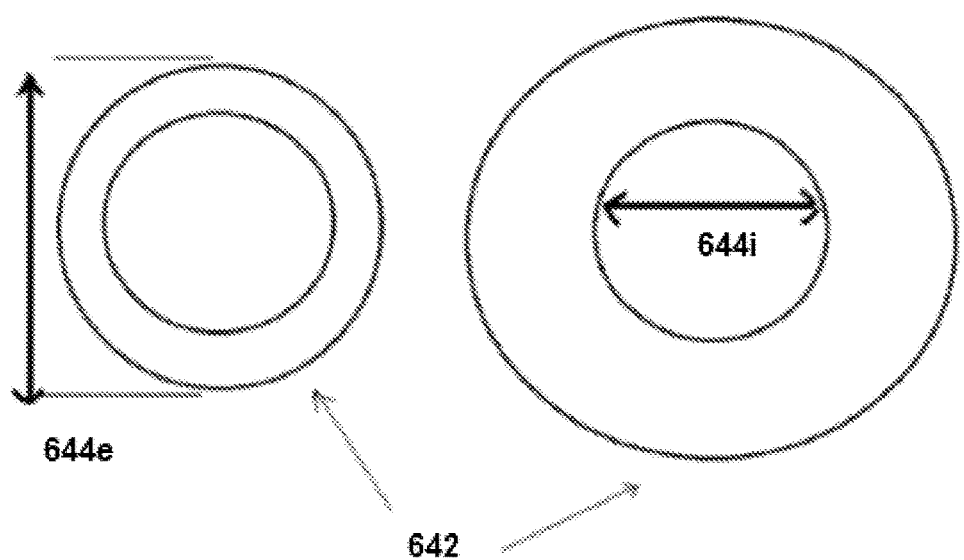
FIG. 31 depicts two support elements, each having the same internal diameter but different external diameters.

In most embodiments of the valve support disclosed herein, the sizes of the ring-like support elements may, as depicted in FIG. 31, be defined by two different dimensions—an external diameter 644$e$ and an internal diameter 644$i$. It will be seen that while both of the support elements 642 shown in this figure have the same internal diameter, their external diameters differ. It will be appreciated that the internal diameter defines the space available for implantation of the replacement valve within the valve support device, while the external diameter needs to be the same as the space within the native Mitral annulus (in order to permit stable implantation of the valve support). Since both the expanded diameter of different commercially-available replacement cardiac valves (e.g. prosthetic aortic valves) and the diameter of the anatomical mitral annulus differs (from patient to patient), it follows that a range of valve support devices needs to be manufactured and made available, such that the clinician can select the valve support having an internal diameter appropriate for the replacement valve to be implanted and an external diameter of the same size as the space within the mitral annulus.

In the embodiments described herein the support elements do not have a covering element. In some embodiments, however, one or more support elements can have a covering element such as a sealing skirt to enhance the sealing of blood flow in and around the support structure and replacement heart valve. The covering element can be any type of material that surrounds the support elements and provides the enhanced sealing functionality (e.g. it can prevent fluid leakage between the valve support and the heart wall). In some embodiments, the covering element can be attached (e.g. by the use of a biocompatible adhesive) to the outer surface of the support elements. In other embodiments, the covering element can be attached to the inner surface of the support elements.

In some embodiments one or more of support structures is covered in a material such as a polyester fabric (e.g., Dacron). Alternatively or in addition to, one or more of the bridge members can be covered in a polyester fabric such as Dacron.

In certain embodiments, the valve support device may further comprise one or more stabilizing elements attached to the upper support element, the lower support element or to both of said elements. The purpose of the stabilizing elements is to increase the multi-directional stability of the implanted valve support device (and thus also enhance the stability of the implanted replacement valve), by means of stabilizing elements in the form of additional complete ring structures (in some cases, similar to the upper and lower support elements themselves), partial rings or curved arms, whereby said structures are placed such that at least part of their length is in close apposition to the surface of the inner ventricular wall and/or the surface of the inner atrial wall (in the case of stabilizing elements attached to the upper support element). Since the curvature of the inner walls of both the atrium and ventricle may be defined in relation to two mutually-perpendicular axes (horizontal and vertical), the stabilizing elements may be disposed either horizontally (i.e., essentially parallel to the horizontal axis of the valve support device) or vertically (i.e. essentially parallel to the vertical axis of the valve support device.). Additionally, in some embodiments, the stabilizing elements may be disposed such that they are neither parallel to the horizontal axis nor to the vertical axis, but rather are arranged at an acute angle to one of these axes.

In some cases, the stabilizing elements (which may be formed from either elastic or plastic materials, as will be described hereinbelow) will be manufactured as an integral part of the valve support device. In other cases, said stabilizing elements will be manufactured separately (by casting, milling, laser-cutting or any other suitable technique known to skilled artisans in the field), and later connected to one or both support elements by means of soldering or laser welding.

Figure 32:
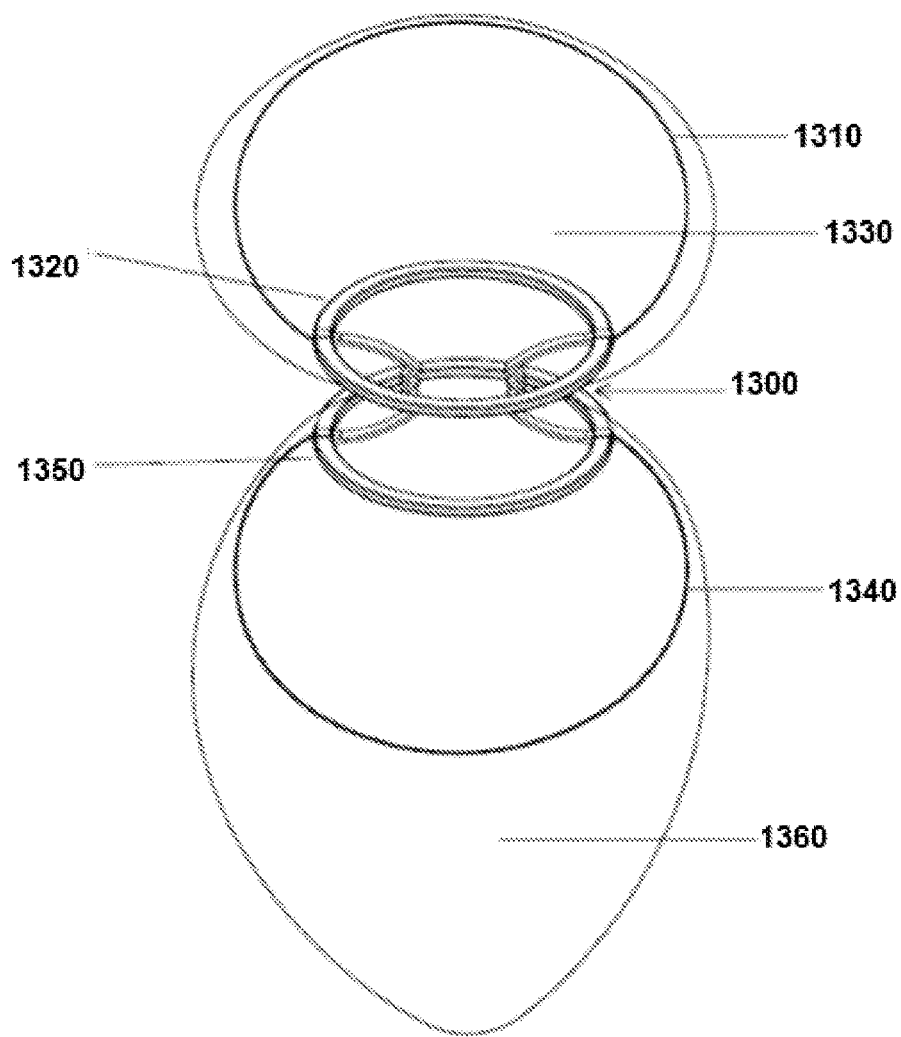
FIG. 32 illustrates an embodiment of the valve support device of the present invention fitted with two vertically-disposed stabilizing elements.

FIG. 32 illustrates a valve support device 1300 of the present invention fitted with two vertically-disposed ring-shaped stabilizing elements. As shown in the figure, the upper, apical ring 1310 is attached at its lower portion to the upper support element 1320, while its upper portion is disposed within the atrium 1330, in close contact with the inner atrial wall. Conversely, the lower, ventricular ring 1340 is attached, at its upper end, to the lower support element 1350, while its lower portion is disposed within the ventricle 1360, in close contact with the inner ventricular wall.

Figure 33A:
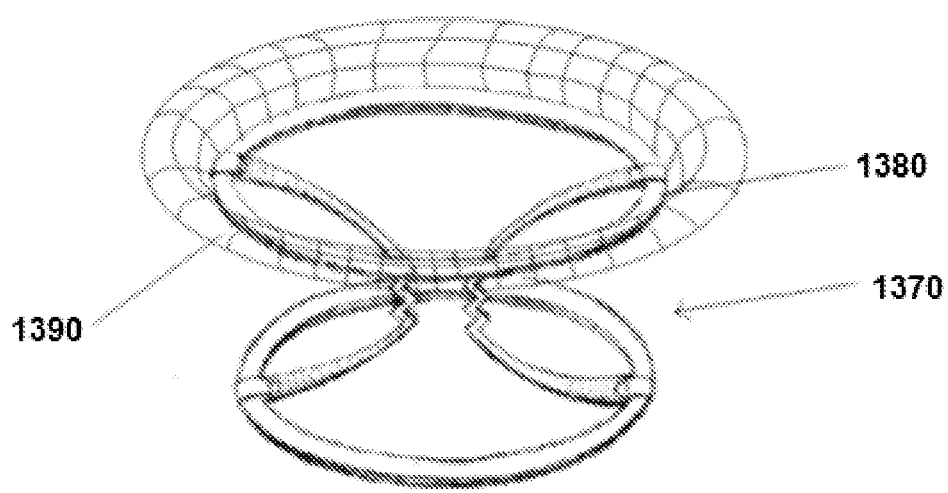
Figure 33B:
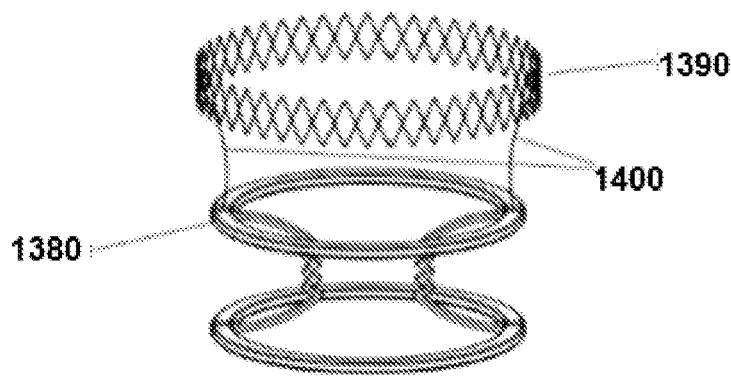

In the case of horizontal stabilizing elements, the element itself can (as explained above) be a complete ring, a partial ring or a curved elongate arm. While in some complete ring embodiments (as shown, for example, in FIG. 32), the stabilizing element is constructed from a single looped wire or solid band, in other embodiments, it may be constructed in the form of a stent-like mesh. FIG. 33A illustrates one embodiment of this type, in which the mesh-like stabilizing element 1390 is attached directly to the upper support element 1380 of valve support device 1370. Alternatively, as shown in FIG. 33B, the mesh-like stabilizing element 1390 may be connected to the upper support element 1380 by means of additional bridging members 1400, which serve as spacer arms, increasing the separation distance between the stent-like mesh stabilizer 1390 and said support element 1380.

Figure 34:
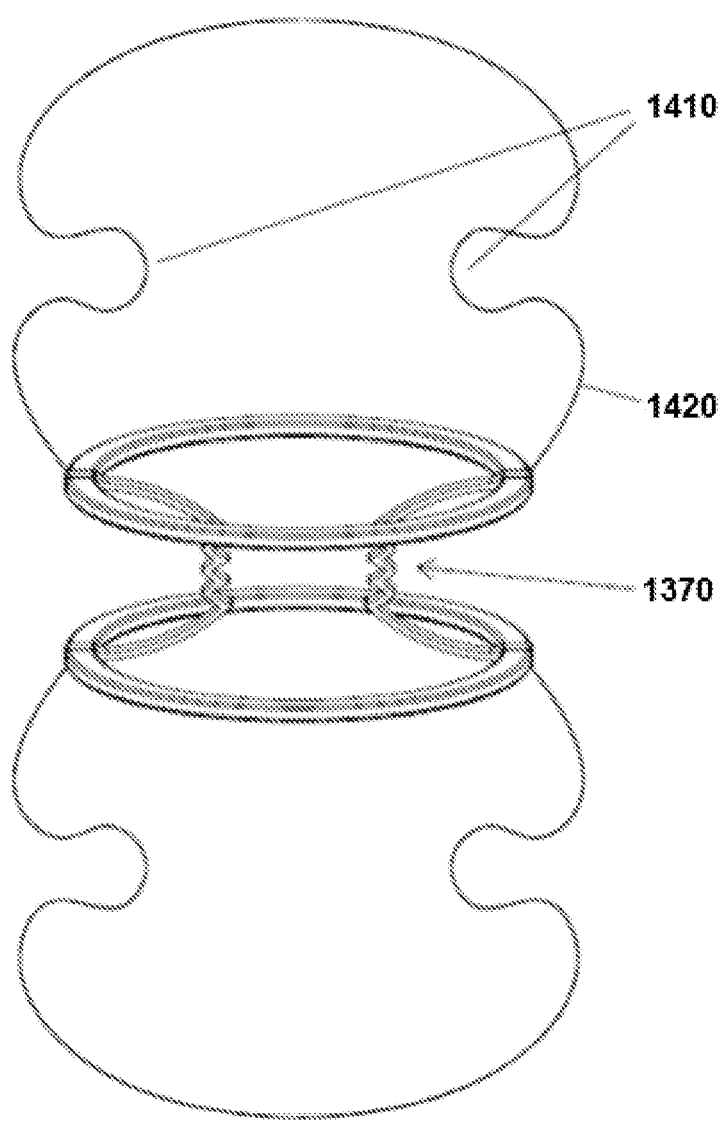
FIG. 34 illustrates an embodiment of the valve support in which the stabilizing element contains spring-like constricted regions.

While the stabilizing element is generally constructed such that its outline shape is that of a smooth curve, in one preferred embodiment, as depicted in FIG. 34, this smooth curve is broken by one or more constricted regions 1410, wherein said regions act as spring-like elements, increasing the force that said stabilizing element 1420 is capable of applying to the inner ventricular or atrial wall, and thereby enhancing the ability of said stabilizing element to stabilize the valve support device 1370. The device shown in FIG. 34 contains two vertical stabilizing elements—a ventricular stabilizing element attached to the lower support element and an atrial stabilizing element attached to the upper support element. In other versions of this embodiment, the valve support device may be fitted with one vertical stabilizing element (attached to one support element) and one horizontal stabilizing element (attached to the other support element). In some other embodiments, the valve support device contains only one such stabilizing element (horizontal, vertical or otherwise angled). In still further embodiments, a single valve support device may contain one stabilizing element containing one or more constricted regions 1410, as shown in FIG. 34, together with one or more stabilizing elements of any of the other types disclosed and described herein.

Figure 35:
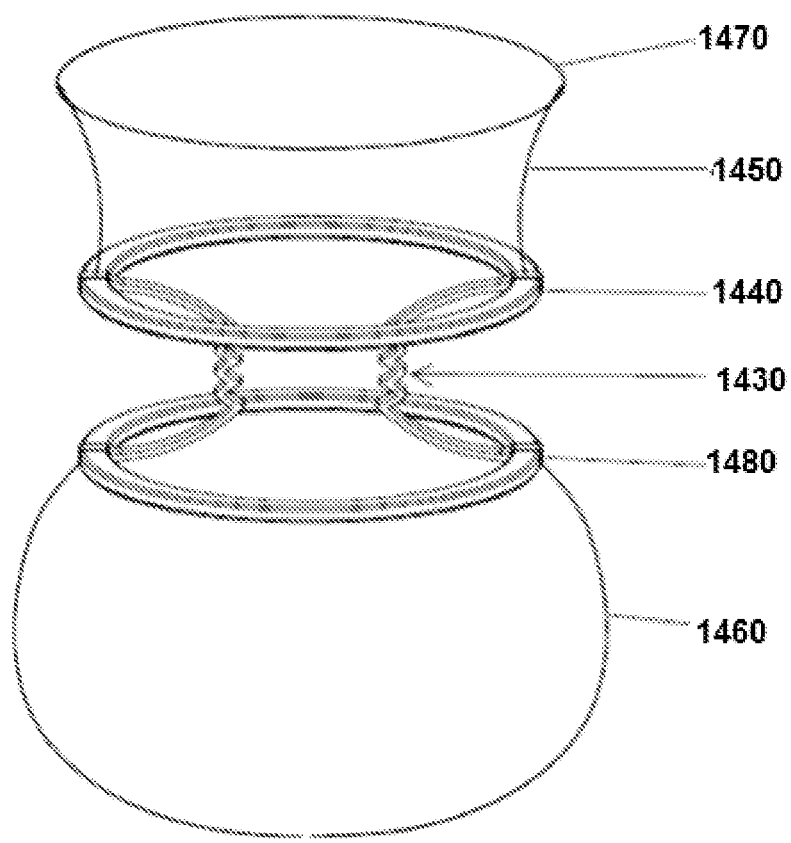
FIG. 35 illustrates an embodiment in which the valve support is fitted with one horizontal stabilizing element and one vertical stabilizing element.
Figure 36:
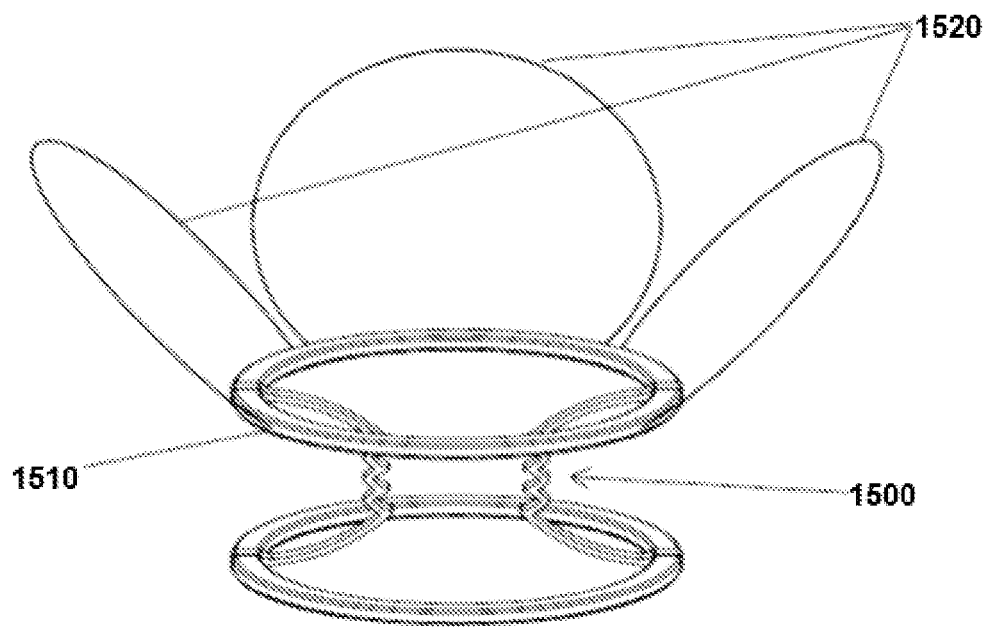
FIG. 36 depicts an embodiment of the valve support having a plurality of stabilizing elements attached to the upper support element.

A further example of a valve support device fitted with a combination of different stabilizing elements is shown in FIG. 35. Thus, lower support element 1480 of valve support device 1430 is fitted with a vertically aligned ring-like ventricular stabilizing element 1460, while a horizontally-aligned atrial stabilizing element 1470 is connected via additional bridging elements 1450 to upper support element 1440. While only two additional bridging elements 1450 are depicted in this figure, as many such elements as necessary may be incorporated into the device. Of course, in other versions, the arrangement of the stabilizing elements shown in FIG. 35 may be reversed, such that the valve support device contains a horizontal lower stabilizing element and a vertical upper stabilizing element. As mentioned above, all possible combinations of the various types of stabilizing element disclosed herein may be used, as appropriate. It should also be noted that more than one stabilizing element may be attached to one or both support elements. FIG. 36 illustrates one embodiment of this type, in which the upper support element 1510 of the valve support device 1500 is fitted with several (in this case, three) non-horizontal, angled, atrial stabilizing elements 1520.

Figure 37A:
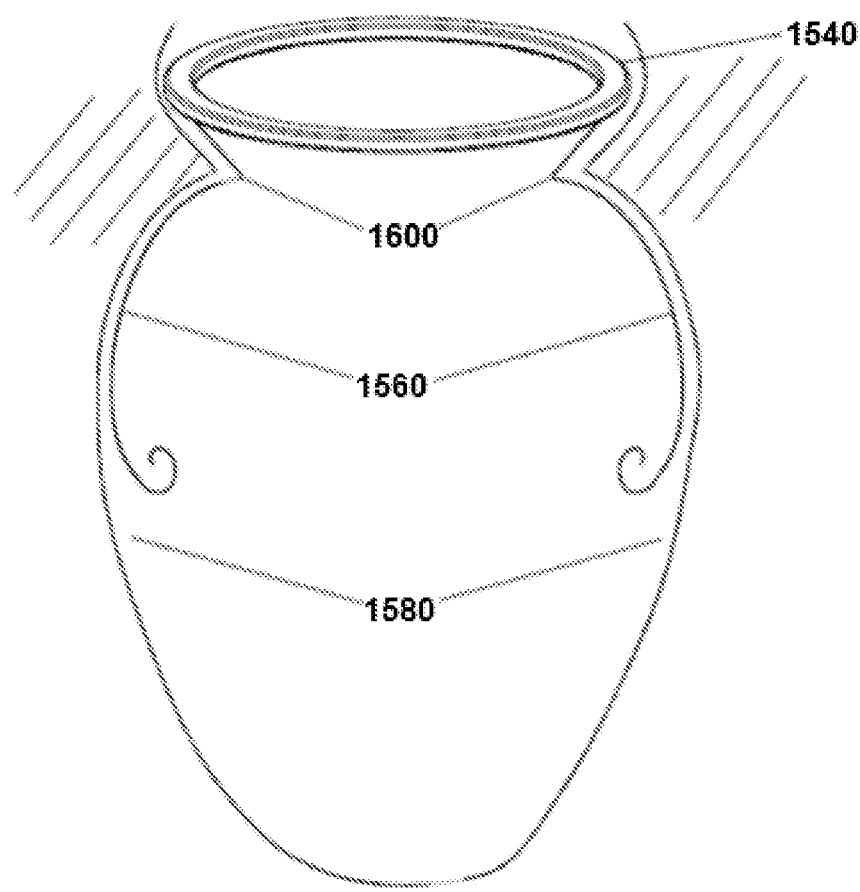
FIGS. 37A, 37B and 37C depict embodiments of the valve support of the present invention in which the stabilizing elements are constructed in the form of curved arms.

As explained hereinabove, the stabilizing element need not be provided in the form of a complete ring, but rather may also have the form of a partial ring or a curved elongate arm. Various examples of the latter type of stabilizing element are shown in FIGS. 37A, B and C. (For the sake of clarity, only the upper support element of the valve support device is shown in these figures. It should be noted, however, that in all cases, these valve support devices will all comprise both a first, upper support element that is implanted above the anatomical annulus, and a second, lower support element that is implanted below the annulus.) Thus, FIG. 37A depicts an upper support element 1540 of a valve support device of the present invention, wherein said valve support device is connected to—and stabilized by—two curved elongate arms 1560 which are disposed vertically downwards along the inner ventricular wall 1580. In the example shown in this figure, the stabilizing elements 1560 are constructed from an elastic material (such as cobalt base alloy, nitinol, stainless steel and other biocompatible metals and metal alloys). The curved arms typically have a length of between 1 mm and 50 mm, preferably about 20 mm. As will be seen in the figure, the upper part of each stabilizing element 1560 is angled such that it is able to pass around the cardiac annulus 1600. In some embodiments, the elongate, curved elastic arms may be constructed such that they are in a state of pre-load. The elastic properties of the stabilizing elements will cause said element to tend to both grip the annulus and to apply an outward force on the ventricular wall inferior to the annulus. In an alternative embodiment of this aspect of the invention, the curved elongate stabilizing elements may be constructed from a plastically-deformable material such as stainless steel, cobalt base alloy and nitinol. In this case, the elongate arms are molded around the annulus using a clenching or crimping tool. In this way, the upper sections of the elongate arms will firmly grip the annulus, while the lower sections will be biased outward and downwards along the ventricular wall.

Figure 37B:
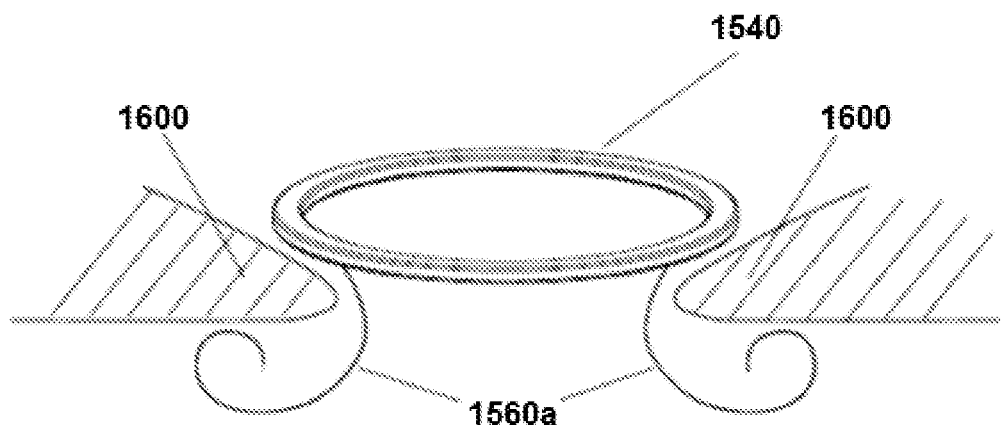

FIG. 37B illustrates another embodiment of this aspect of the device, wherein the stabilizing elements 1560a attached to upper support element 1540 are much shorter than those shown in FIG. 37A, and apply a stabilizing force to the inferior surface of the annulus 1600 (rather than to the lateral inner walls of the ventricle). During implantation, the stabilizing elements are brought into position below the annulus, such that the annulus becomes "trapped" between said stabilizing elements and the upper support element itself.

Figure 37C:
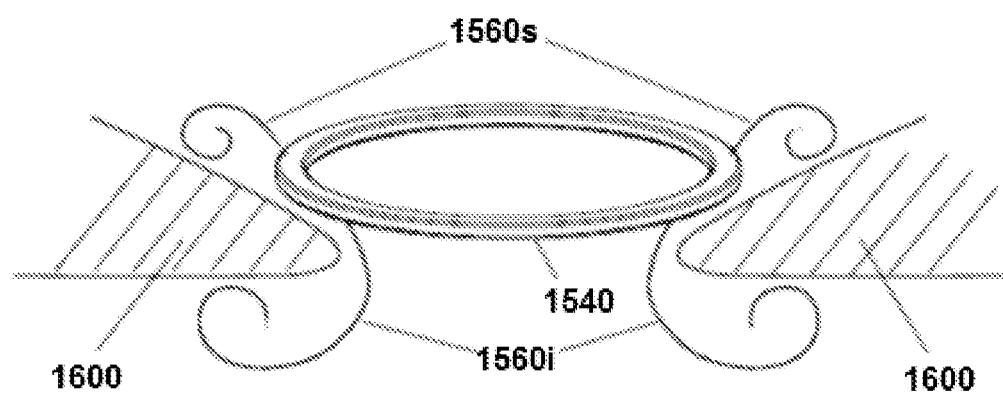

A still further variant of this embodiment is illustrated in FIG. 37C. This variant differs from the embodiment shown in FIG. 37B, in that the upper support element 1540 is fitted with both upper (1560s) and lower (1560i) stabilizing elements. During implantation into a patient, the valve support device is manipulated such that the annulus 1600 becomes "trapped" between these upper and lower stabilizing elements. In each of the variants of this embodiment, the short stabilizing elements may be brought into position by means of a balloon expansion mechanism, by a mechanical closure mechanism or, alternatively, said stabilizing elements may be self-expanding.

Figure 38:
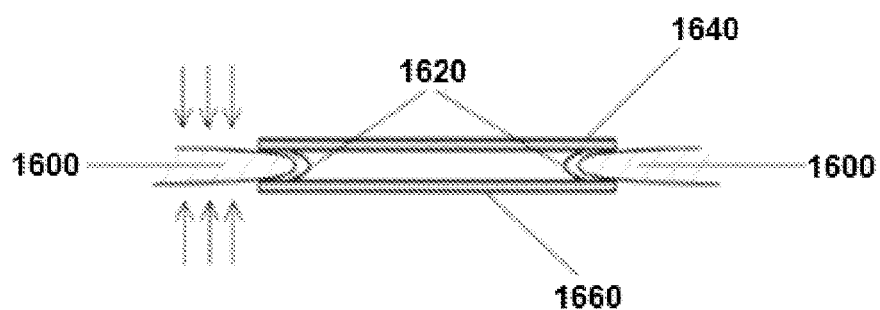
FIG. 38 illustrates an embodiment of the valve support in which a horizontal ring-shaped stabilizing element is located between the upper and lower support elements.

FIG. 38 depicts an alternative design of the valve support of the present invention, additionally comprising a horizontally-disposed ring-shaped stabilizing element 1660, located between the upper support element 1640 and the lower support element (not shown). Elastic members 1620 mutually connect the upper support element (1640) and said additional ring support (1660). The annulus 1600 may thus become trapped or pinched between them (as indicated by the arrows). This design may either be used without any additional stabilization elements, or in combination with any of the stabilization element embodiments described hereinabove.

Figure 39A:
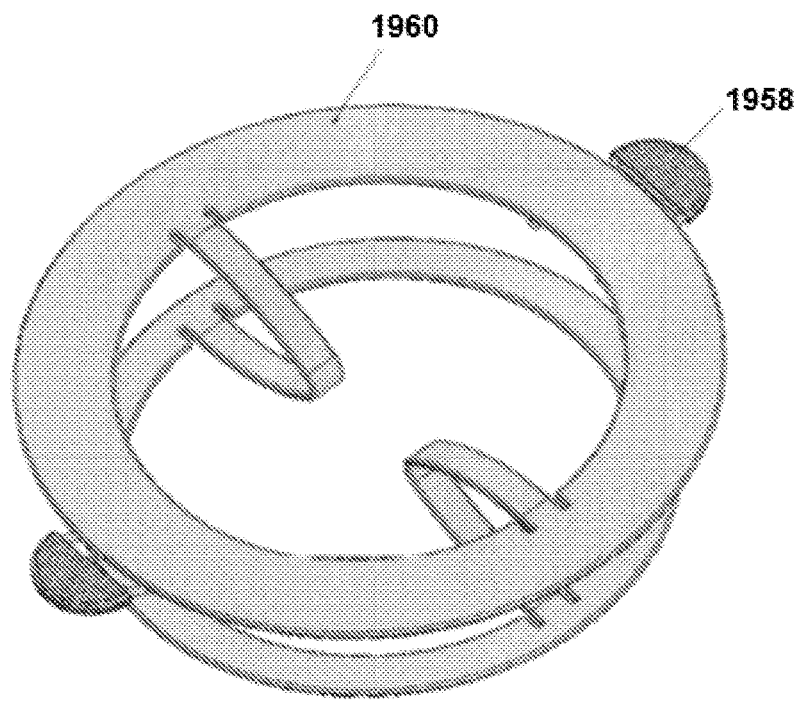
FIGS. 39A and 39B show a valve support device with a pair of elastic tab-like stabilizing elements attached to the upper support element.
Figure 39B:
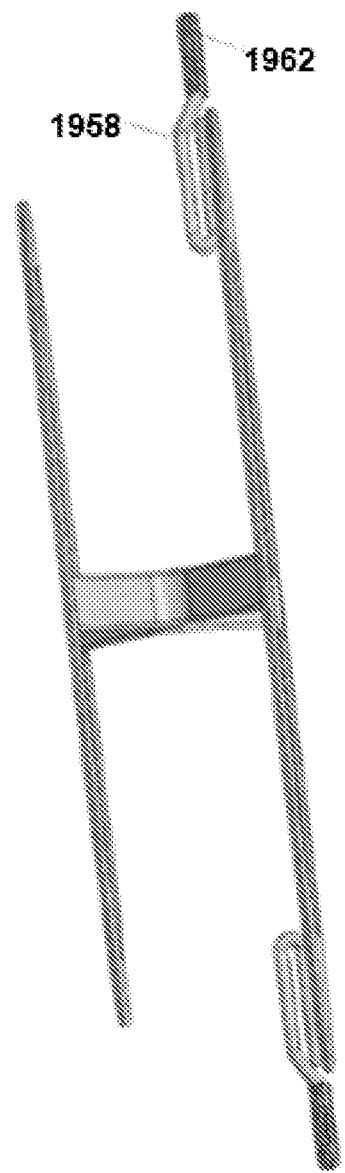

In a still further embodiment, as depicted in FIG. 39A, the valve support device as viewed from above is seen to comprise a pair of elastic stabilizing elements 1958, one on each side of the upper support element 1960. These stabilizing elements may be manufactured from biocompatible metals including (but not limited to) Nitinol, Cobalt and Stainless steel, and are manufactured in the form of a spring-like tab that permits the elastic forces applied by the device on the ventricular wall to be distributed over a large surface area, so as to minimize local pressure on the cardiac tissue, thus minimizing the danger of necrosis of cardiac tissue due to high-level mechanical stress. The structure of the tab-like stabilizing elements 1958 may be better seen in the side view of this embodiment of the device, presented in FIG. 39B. As may be seen from these figures, each tab may preferably be covered by a biocompatible fabric or mesh 1962 (for example made from Dacron, PTFE etc.), the key functions of which are to assist in distributing the force, as previously explained, and also to encourage growth of cardiac tissue on the device, thus improving the attachment thereof to the heart wall. One particular advantage of using this type of stabilizing element is that it approximates the upper support element to the floor of the left atrium, thus essentially compressing the annulus (the stabilizing element compressing from the ventricular side and the upper support element compressing from the atrial side), thereby forming a "plug" that will prevent paravalvular leakage, even in cases in which the annulus is larger in diameter than the prosthetic valve, provided that the upper support element is larger than the annulus. In this embodiment, the upper support element may be fitted with one or more stabilizing elements of this type, which may be distributed evenly or unevenly around the circumference of said support element. Exemplary dimensions of this tab-like stabilizing element are as follows: width 2-20 mm; and length 2-20 mm. However, it is to be recognized that these measurements are for the purposes of illustration only, stabilizing elements of dimensions larger or smaller than these ranges being included within the scope of the present invention.

Figure 40:
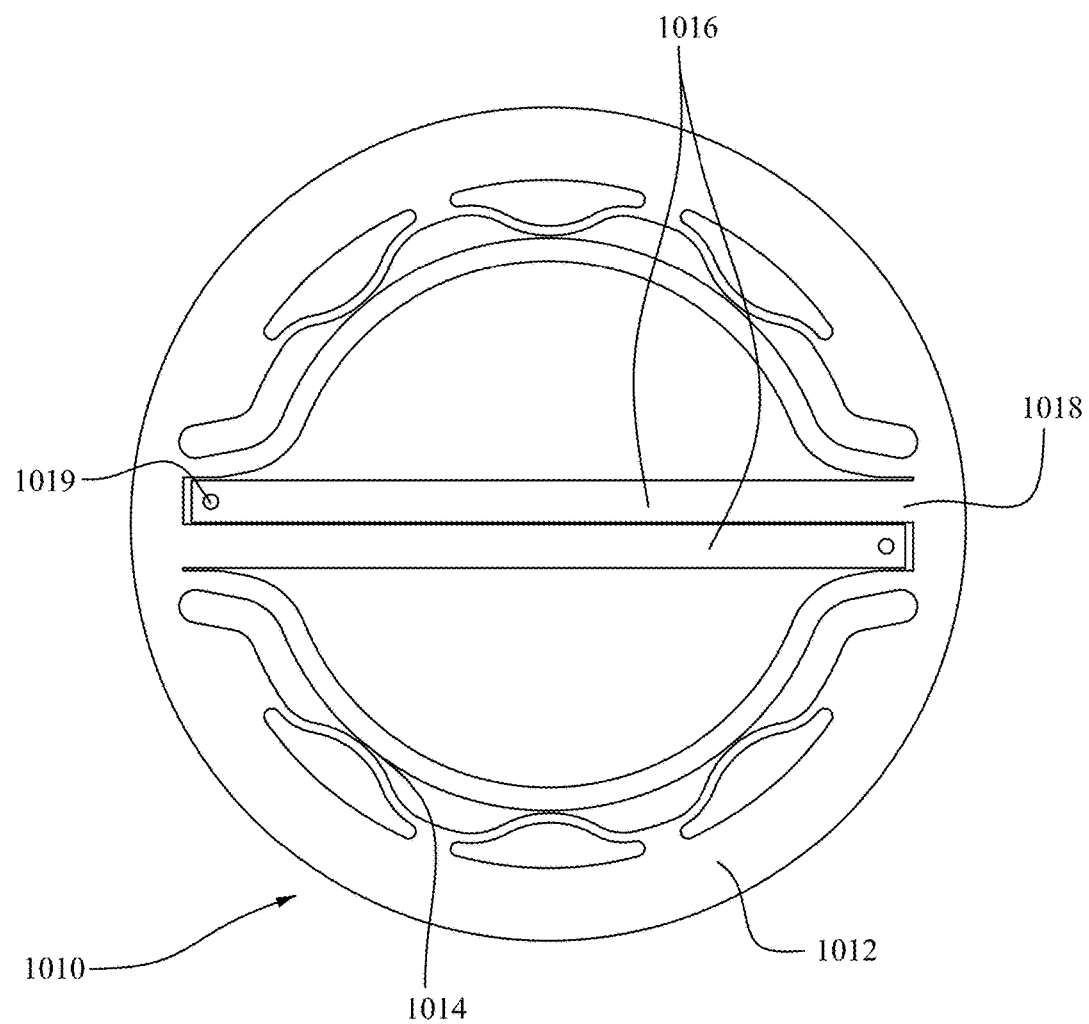
FIG. 40 illustrates a support device fitted with two elongate anchoring wings.

As explained hereinabove, the stabilizing element need not be provided in the form of a complete ring, but rather may also have the form of a partial ring or a curved elongate arm. Further examples of the latter type of stabilizing element are shown in FIGS. 40-48. An example of a support structure comprising two anchoring wings of this type is illustrated in FIG. 40. (It will be appreciated that this figure—as well as all similar figures exemplifying top views of similar devices—are intended to show said devices in their pre-crimped conformation.) The support structure 1010 in this example is seen to comprise a circular support ring 1012 fitted with elements 1014 which permit the inner circumference of said ring to elastically deform in a radial direction (thereby facilitating the precise adaptation of the ring to a replacement valve of any size). The device also comprises two anchoring wings 1016, the basal sections 1018 of which are continuous with the ring itself. Indeed, in most preferred embodiments, the wings have been cut out of the same disk as the ring itself. Finally, each of said wings also has a small aperture 1019 formed close to its distal tip, the purpose of said aperture being assist the operator in gripping the support device during implementation, as will described in more detail, hereinbelow.

Figure 41:
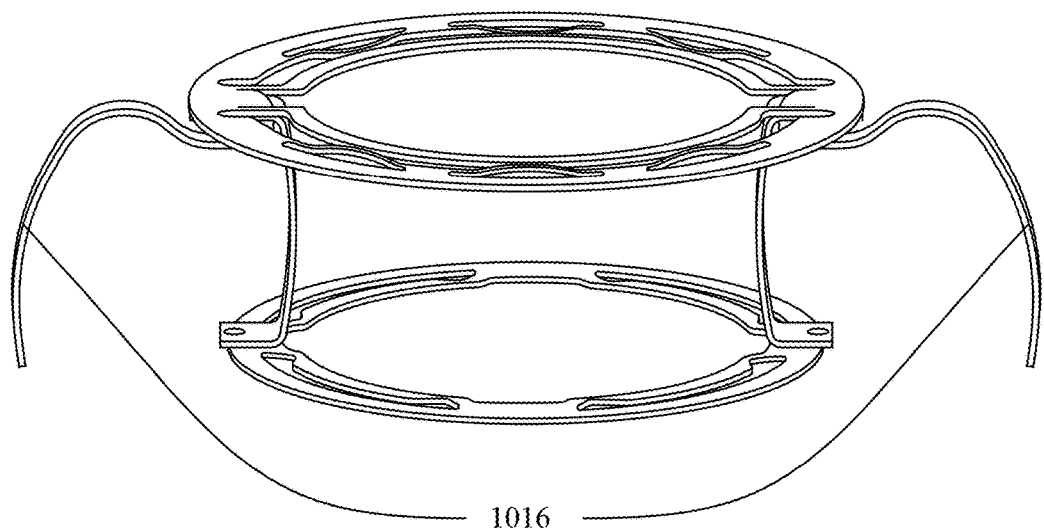
FIG. 41 shows the valve support device depicted in FIG. 40, following its release from the delivery catheter, and after the anchoring wings have expanded into their open, working conformation.

FIG. 41 shows the same valve support device following its release from the delivery catheter, and after the anchoring wings 1016 have expanded into their open, working conformation.

Figure 42:
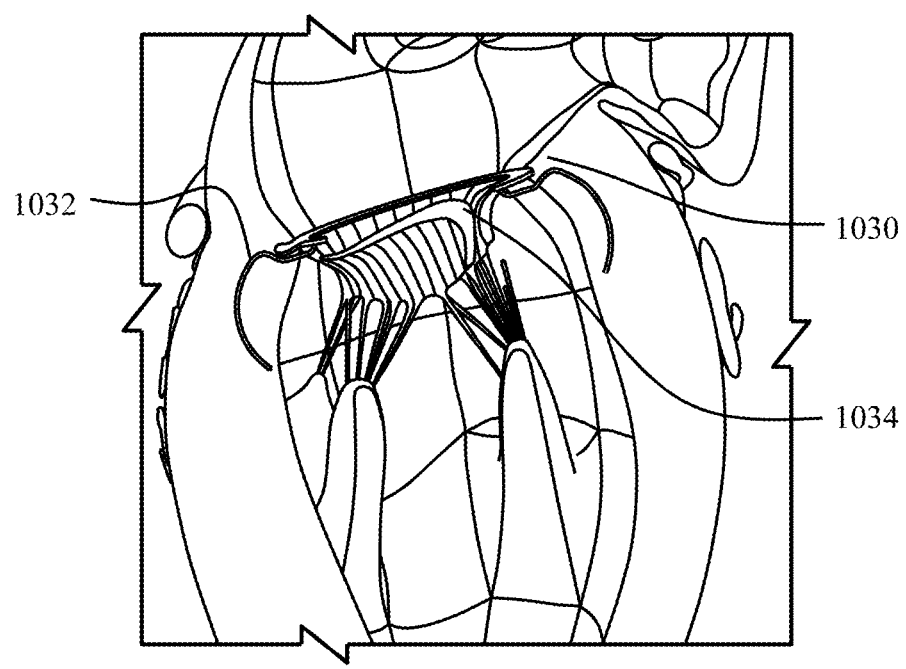
FIG. 42 illustrates the valve support device of FIGS. 17 and 18 following its implantation into the heart in the region of the cardiac annulus.

FIG. 42 illustrates the valve support device of FIGS. 40 and 41 following its implantation into the heart in the region of the cardiac annulus 1030 (lower support element not shown for clarity). Thus, it will be seen that the anchoring wings 1032 are aligned along the commissure of native mitral valve 1034, such that the presence of the support device does not interfere with the functioning of said native valve at this stage. It is to be noted that the anchoring wings 1032 compress the ventricular tissue with which they are in contact, thereby causing a slight radially-outward displacement of said tissue. (This displacement is not visible in FIG. 42, due to drawing limitations.)

Figure 43:
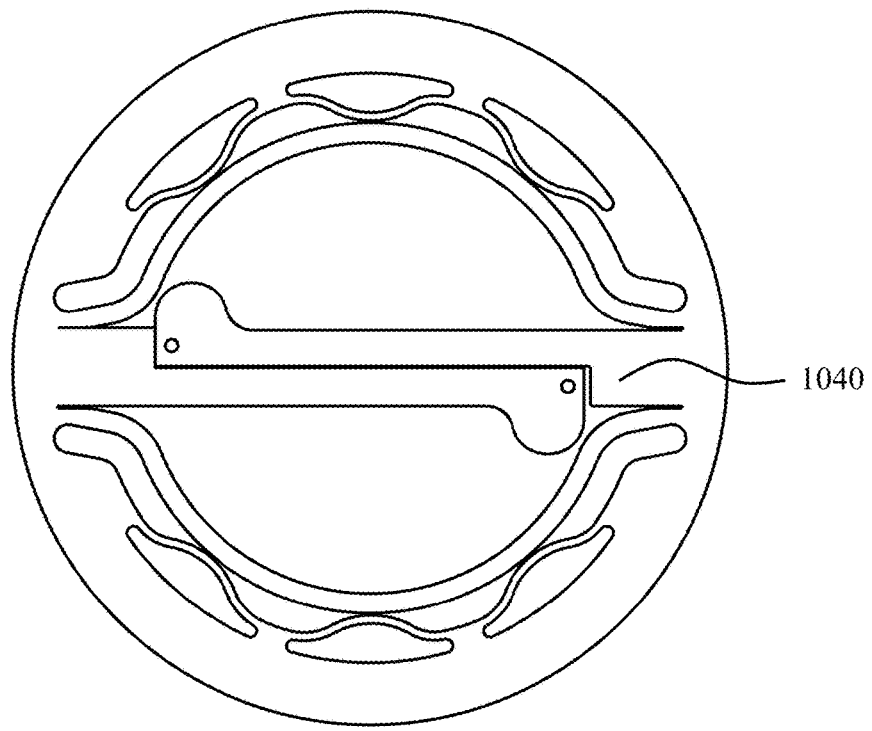
FIG. 43 depicts a different embodiment of the invention, wherein the anchoring arms have enlarged basal sections.
Figure 44:
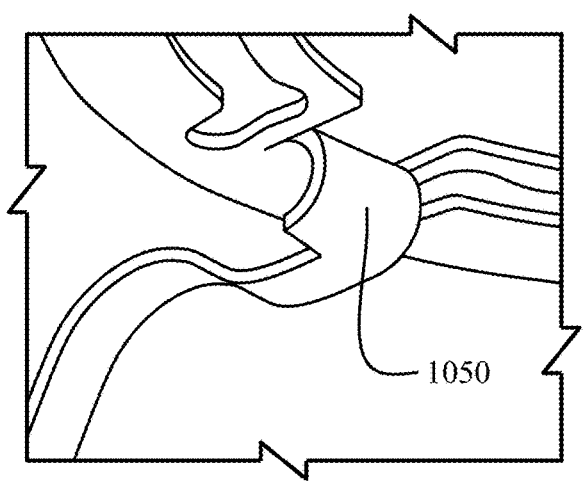
FIG. 44 shows the embodiment of FIG. 43 in its expanded conformation.

A different embodiment of this aspect of the invention is illustrated in FIG. 43, in which it may be seen that each anchoring wing has an enlarged basal section 1040. It may be further seen in the enlarged side view of this device in its expanded conformation (shown in FIG. 44), that the expanded basal section (now shown as 1050) contributes to the mechanical strength of the anchoring wing precisely at the point where said wing curves away from the ring support structure.

Figure 45:
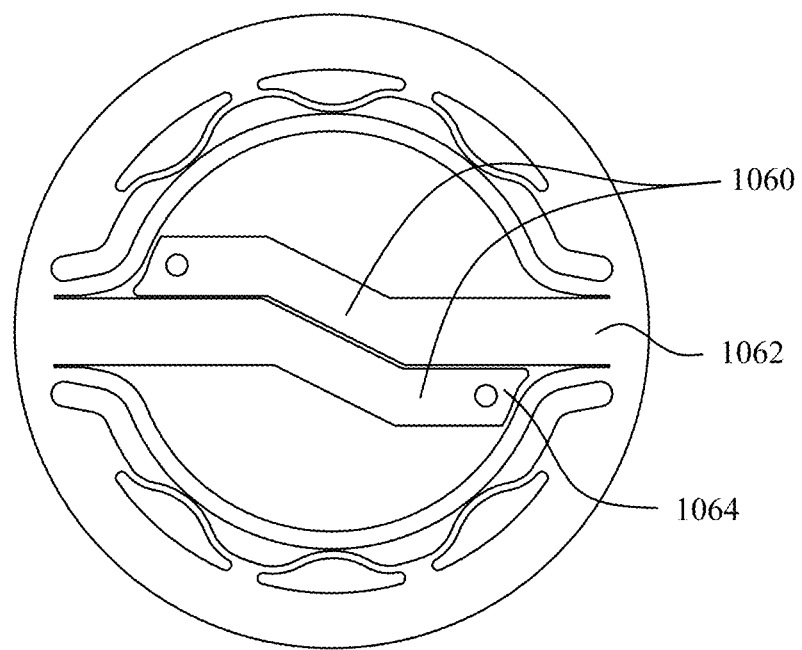
FIG. 45 depicts a different embodiment, wherein the anchoring wings are broader than in the previously depicted embodiments.

In yet another embodiment, as shown in FIG. 45, the anchoring wings 1060 are broader than the wings depicted in the earlier drawings, this increased breadth being maintained along the entire length of each of said wings, from the basal section 1062 to the distal tip 1064. As a consequence of their greater breadth, the anchoring wings of the embodiment depicted in this figure are able to transmit a greater stabilizing force onto the ventricular tissue. This larger wing also distributes the anchoring force on a larger surface area of the heart—this is beneficial since force distribution reduces the local stress on myocardial tissue, and this may be clinically beneficial since it will prevent high stresses that may damage tissue.

Figure 46:
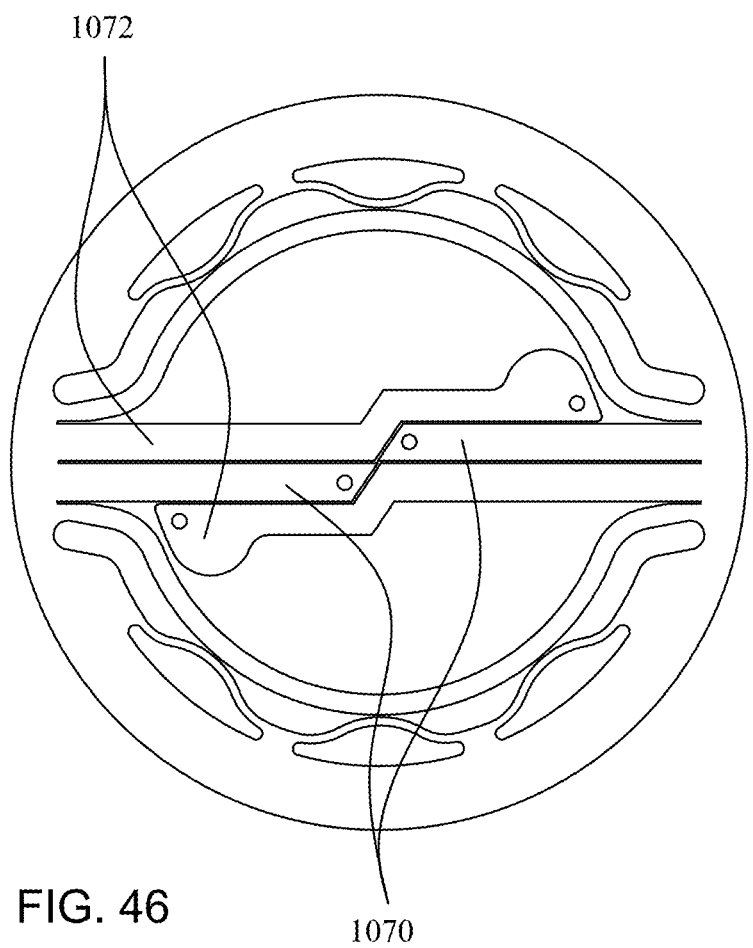
FIG. 46 depicts a device having two short wings and two long wings.
Figure 47:
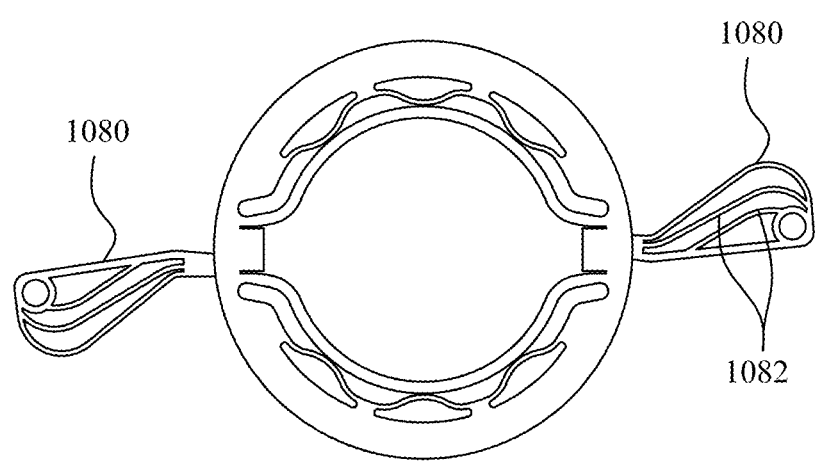
FIG. 47 shows a support device fitted with an open-work structure (lower support element not shown for clarity).

A slightly different approach is shown in FIG. 46, in which the support device comprises four anchoring wings—two short wings 1070 and two long wings 1072 which are disposed such that one short wing and one long wing are situated side-by-side on each side of the device. One advantage of this embodiment of the support device is that the presence of both a short wing and a longer wing on each side forms a compensatory mechanism such that in the event that one of said wings (e.g. the long wing) on each side does not make satisfactory contact with the ventricular wall, then the other one (the short wing) will be able to do so.

In all of the various embodiments described thus far and depicted in FIGS. 40 to 46, the anchoring wings are formed as solid structures cut out of the same disk as the support ring itself. In an alternative approach, as shown in the photographic view presented in FIG. 47 (lower support element not shown), the wings 1080 are constructed as open structures. This type of wing may be created, for example, by means of first cutting out a broad wing from the support ring disk, and then further removing material, such that one or more metallic strands remain within the wing. Two such strands 1082 are shown in the design depicted in FIG. 47. One advantage of this approach is that broader anchoring wings may be constructed (thereby being able to apply stabilizing forces to a larger area of the ventricular wall), without adding to the bulk or weight of said wings. As previously explained, this larger wing also distributes the anchoring force on a larger surface area of the heart—this is beneficial since force distribution reduces the local stress on myocardial tissue, and this may be clinically beneficial since it will prevent high stresses that may damage tissue.

Figure 48:
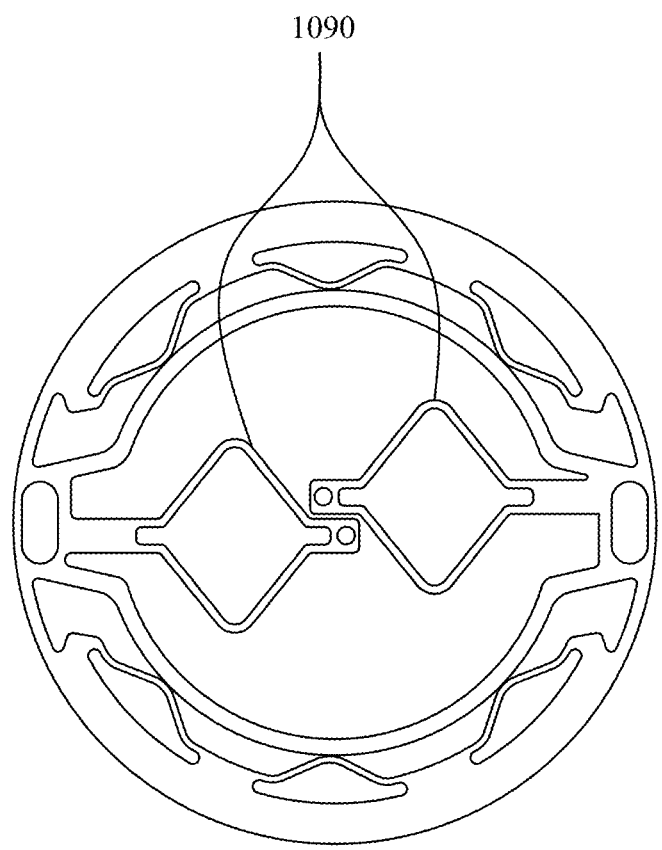
FIG. 48 depicts an embodiment having an alternative open wing structure.

A further embodiment is shown in the photograph presented in FIG. 48. The device shown in this figure comprises wings having an open structure that are capable of existing in two different conformations—(a) an elongated, small-diameter conformation that is created during crimping during the insertion of the device into the delivery catheter and (b) a shortened, broad form, as shown in FIG. 48. As shown in the figure, the anchoring wings 1090 of this specific embodiment, in their working conformation, have a broad, diamond-like shape, and are thus capable of exerting relatively high stabilizing forces on regions of the ventricular wall close to the support device. It is to be noted that if wings having this enlarged breadth were to be formed as solid structures, it would be very difficult to crimp the device into its collapsed, delivery, conformation. Thus, the use of a skeleton structure of the type shown in this figure is highly advantageous since it combines the advantages of long, narrow wings for catheter delivery with the mechanical advantages of short, broad wings once the support device has been deployed.

The wings may be covered—either completely or, alternatively, at their distal tips only—with a fabric or other covering material. In one highly preferred embodiment, a covering material, such as biocompatible Dacron, that will permit ingrowth of cardiac tissue thereinto, is used. In this way, additional anchoring of the wings to the cardiac tissue may be achieved.

The devices may be produced by laser cutting of the Nitinol disks that are used to create the support devices. The rings are then subjected to heat treatment (at temperatures of, for example, 500-600 degrees C.) with the wings bent in the desired working position, such that following release from the delivery device, the wings will adopt this new shape-memory position.

In some preferred embodiments, the wings will have small holes drilled through their distal-most portions, in order to allow the operator to easily grip the support device with a narrow-ended tool or wire during release from the delivery catheter, thereby facilitating the maneuvering of said device into its working position.

Figure 49:
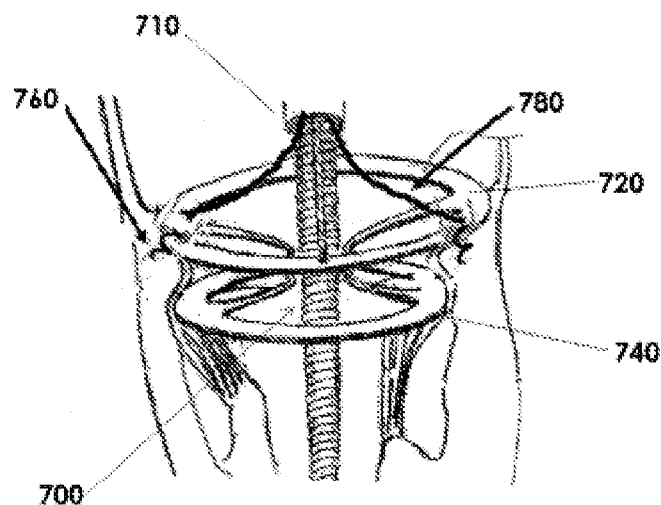
FIG. 49 depicts a valve support containing spiral-shaped cardiac anchoring means.

In some embodiments of the present invention, the careful selection of a correctly-sized valve support device will permit said support device to be self-retaining in the region of the annulus following self-expansion during device delivery, as will be described hereinbelow. In other cases, however, the valve support device of the present invention will further comprise one or more heart tissue anchoring means or mechanisms (connected to the support elements and/or bridging members) for firmly anchoring said valve support to the cardiac tissue. In one embodiment of this aspect, the cardiac anchoring means comprise a plurality of spiral or hook-like anchors. An example of this type of anchoring means is illustrated in FIG. 49, which shows a guide catheter 710 being used to deliver a valve support device 700 of the present invention. At the stage of the delivery process shown in this figure (which will be described in more detail hereinbelow), both of the support elements, 720 and 740, as well as the bridging members have self-expanded into their working conformations. It will be seen that the upper support element is fitted with two spiral cardiac attachment anchors 760, the sharp free ends of which face laterally. The bases (i.e. medial ends) of the anchors are connected to control wires 780 that pass upwards and proximally through guide catheter 710, eventually leaving the patient's body and ending at a proximal control console. Once the valve support device has been manipulated into the desired position (as shown in the figure), the spiral anchors 760 are caused to rotate by means of the operator manipulating the proximal ends of the control wires, thereby becoming inserted within the cardiac tissue and thus firmly anchoring the valve support device in its operating position.

Figure 50:
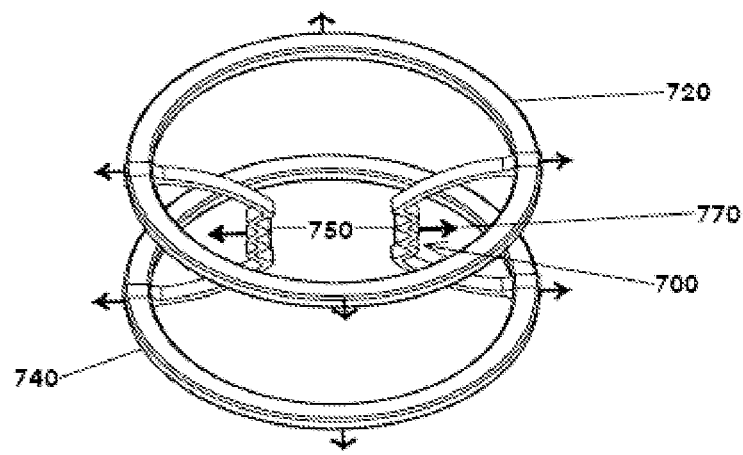
FIG. 50 depicts a valve support comprising a plurality of hook-like cardiac anchors.

It is to be noted that FIG. 49 presents only one exemplary design for the cardiac tissue anchors, and many others are possible and included within the scope of the present invention. Thus, in another embodiment, hook-like anchors are attached at various points along the surface of the valve support device, either on the support elements, the bridging members or both. This embodiment is illustrated in FIG. 50 which depicts a typical valve support device 700, comprising an upper support element 720, a lower support element 740 and two bridging members 750, on the surface of all of which are distributed a number of hook-like anchors 770. (Nine such anchors are shown in the figure.)

Figure 51A:
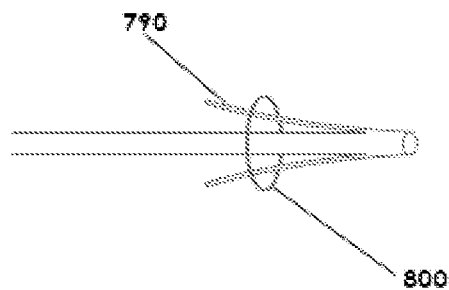
FIGS. 51A and 51B illustrate cardiac attachment anchors having backwardly pointing distal arms which may be retained in a closed position during delivery by means of a resorbable suture loop.
Figure 51B:
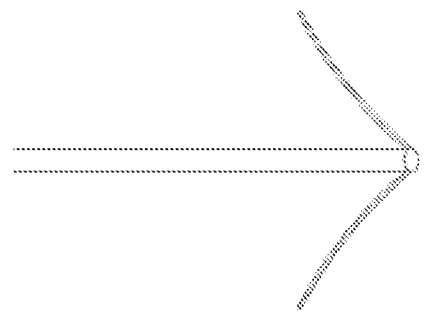

In some situations, it is advantageous for the cardiac tissue anchors to adopt a closed, inactive conformation during insertion of the valve support device into the body, in order to avoid both trauma to the patients tissues and to avoid premature anchoring (for example at an incorrect location). Then, when said device is correctly positioned, the anchors would be caused to move from their closed, inactive conformation to an open active position. There are a number of ways to implement this type of embodiment. Thus, in a first implementation, the cardiac attachment anchor is constructed with two or more backwardly-pointing self-opening distal arms. During insertion and implantation, the distal arms are retained in a closed conformation by means of a small loop of resorbable suture material. Then, after a certain period of time following insertion of said attachment means into the ventricular tissue (e.g. between a few hours and a few weeks), said suture dissolves, thereby permitting the distal arms to adopt their open conformation. This embodiment is illustrated in FIGS. 51A and 51B: in FIG. 51A, the distal anchor arms 790 are shown retained in their closed position by means of suture 800. In FIG. 51B, the required length of time has elapsed (following insertion) and the suture has dissolved, releasing the distal anchor arms and allowing them to spread apart within the cardiac tissue, thereby increasing the resistance to withdrawal offered by said anchor.

In a further embodiment of this type, the anchor hooks are manufactured from a shape memory material, such as biocompatible nickel-titanium alloys (e.g. Nitinol). During insertion, the anchors are in their closed conformation, but following the implantation procedure the rise in temperature experienced during insertion into the patient's body results in opening of the anchors, as they regain their initial shape.

Figure 52A:
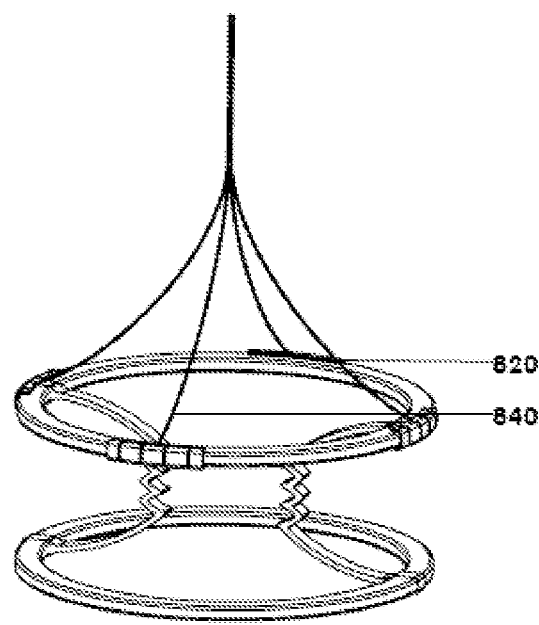
FIGS. 52A and 52B illustrate two different embodiments of cover elements that may be used to conceal the cardiac attachment anchors during delivery of the valve support.
Figure 52B:
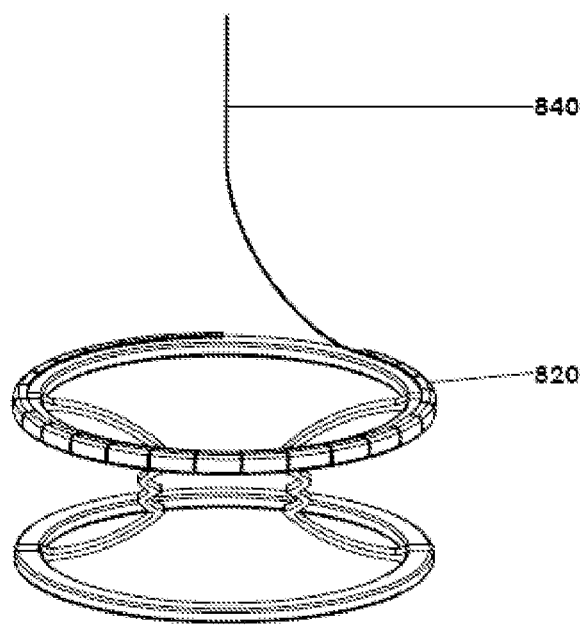

In a still further embodiment of this type, as shown in FIGS. 52A and 52B, the anchor hooks are protected by a cover element 820 (such as a sleeve or a piece of tubing) which is manufactured from a material with limited flexibility, such as PET, nylon and similar biocompatible plastics. After the operator is satisfied that the valve support device has been implanted at the correct site, control elements 840 attached to the cover elements are pulled, thereby withdrawing them through the guide catheter, thus permitting the anchor hooks to freely adopt their open conformation and to become inserted into the cardiac tissue. In the design shown in FIG. 52A, each anchor is protected by its own individual cover, while in FIG. 52B a single cover element protects all of the anchors (not shown) that are attached to the upper support element.

Figure 53A:
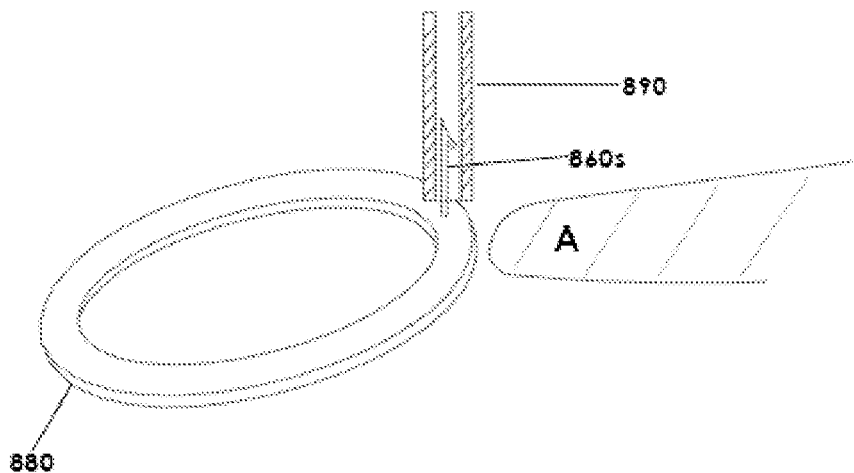
FIGS. 53A and 53B depict the use of a shape-memory anchor which is maintained in a straight conformation during delivery by means of an overtube.
Figure 53B:
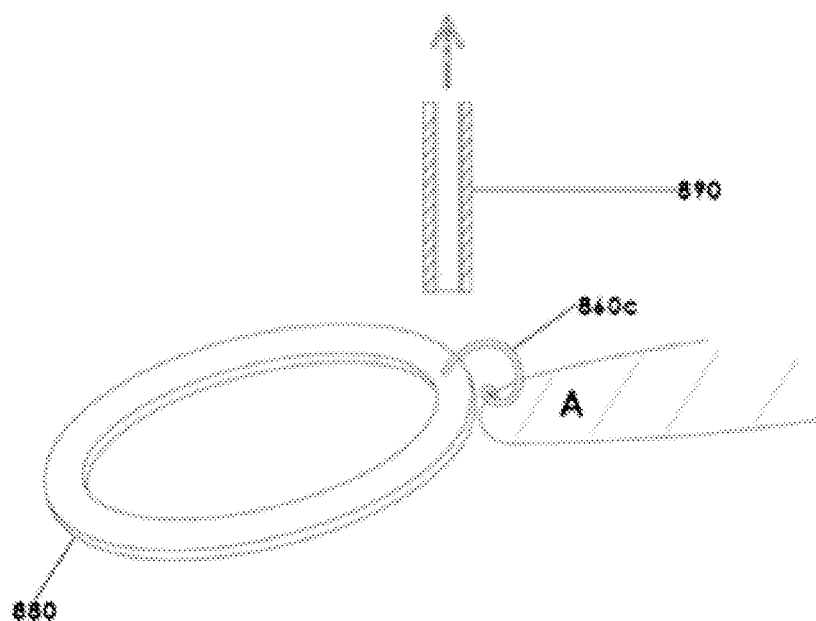

FIGS. 53A and 53B illustrate a yet further embodiment of this aspect of the invention. Thus FIG. 53A shows a barbed anchor 860s attached to a support element 880 is maintained in an inactive, straight conformation by means of an overtube 890, which also serves to protect the patient's tissues from trauma during insertion and implantation of the valve support device. Following implantation at the desired site, as shown in FIG. 53B, overtube 890 is pulled away from the anchor 860c (for example, by means of pulling a control wire), which now adopts its "natural", curved conformation, during which shape transition, said anchor now pierces the cardiac tissue (indicated by the letter A in the figure). Suitable anchors for use in this embodiment can be manufactured from shape-memory materials or from super-elasticity materials such as Nitinol, cobalt base alloy and spring-tempered stainless steel. Typically, anchors of this type will have a mid-length diameter of between about 0.2 mm and 1 mm, and a length in the range of about 2 to about 10 mm. Suitable overtubes may be manufactured from biocompatible polymers such as braided nylon and PET to a tolerance that permits a tight fit over the anchor.

It is to be noted that the cardiac tissue anchors described hereinabove may, in certain cases, be used to attach the valve support device of the present invention to the anatomical valve leaflets and chordae (in addition to, or instead of attaching said device to the inner ventricular wall). In this regard, the present invention also encompasses additional types of cardiac tissue anchor which are characterized by having a plurality of anchoring wires that advantageously become entangled within the valve leaflets and chordae. Anchors of this type are particularly suitable for use in attaching the lower support element and bridging members to the aforementioned anatomical structures.

Figure 54:
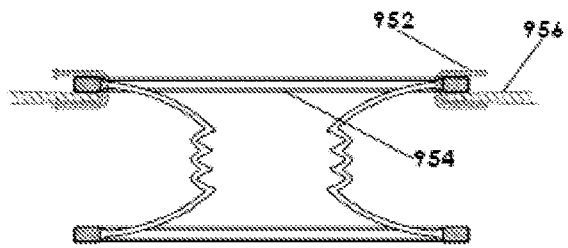
FIG. 54 illustrates clip-like cardiac tissue anchors that are particularly suitable for attaching the support element to the annulus.

In one still further embodiment, the cardiac tissue anchors may be provided in the form of small clips (similar to vascular clips used to close blood vessels during surgical procedures, and well known to the skilled artisan). An example of the use of this embodiment is shown in FIG. 54, in which clip 952 is used to attach the upper support element 954 to the annulus 956. Clips of this type may also be used to attach the upper support element to atrial wall tissue and/or anatomical valve leaflets. In one particularly preferred embodiment the clip is caused to attach to the tissue in the area of the trigone—an anatomical area, on two opposite sides of the mitral valve, which has more fibrous tissue—and which is therefore able to provide a firm base for anchoring the valve support device.

In another embodiment (not shown), the clip may be an integral part of the upper or lower rings, or the bridges. This may be achieved by attaching one of the jaws of the clip to the valve support device, while the second of the jaws is free to be plastically deformed and to become anchored to the tissue.

In the case of certain replacement valves that may be used in conjunction with the valve support device of the present invention, the radially-outward forces exerted by the expanded replacement valve are sufficient to stably retain said valve within the inner cavity of said valve support device. However, in some instances—particularly when self-expanding replacement valves are being implanted—the radial force exerted by the expanded valve may be insufficient to ensure that it can withstand all of the physiological forces exerted therein during all stages of the cardiac cycle. In such circumstances, the bridging members and/or support elements of the valve support device may further comprise a valve engagement portion. In one embodiment, the valve engagement portion may comprise a series of zigzag-like folds or pleats in the central, innermost region of the bridging members. These folds or pleats interact with the struts or other structural features of the replacement valve, thereby stabilizing said valve within the valve support device.

In another embodiment, the valve engagement means comprise either inward facing or outward facing anchors, whose purpose is engage with the external struts of the replacement valve, thereby stabilizing said valve within the support device.

Figure 55:
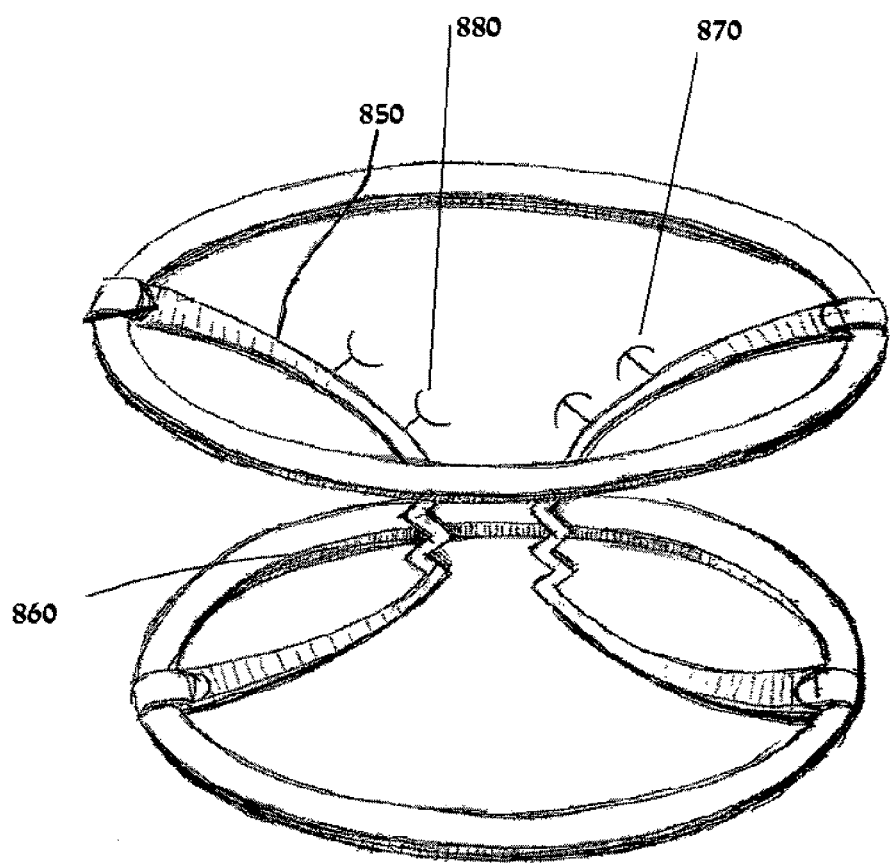
FIG. 55 illustrates a valve support device of the present invention fitted with two different types of valve engagement means.

FIG. 55 depicts a valve support device of the present invention comprising both of the aforementioned embodiments of valve engagement means. Thus, it may be seen that the central portions of the bridging members 850 are folded into a series of pleats 860. In addition, said bridging members are also provided with both inward facing 870 and outward facing 880 anchors.

Figure 56A:
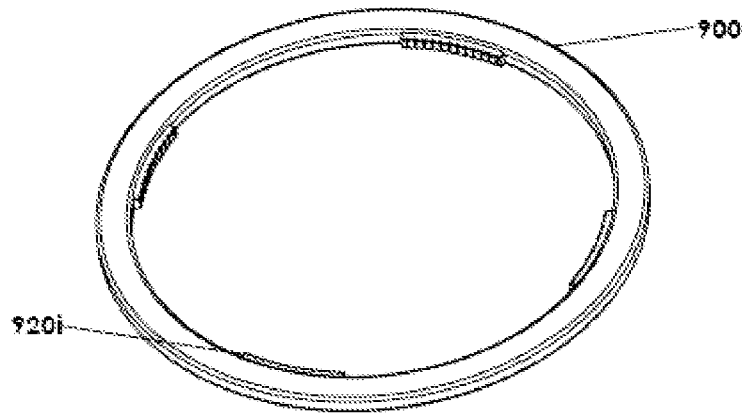
FIGS. 56A and 56B illustrate support elements fitted with a valve engagement means constructed from a soft biocompatible material.
Figure 56B:
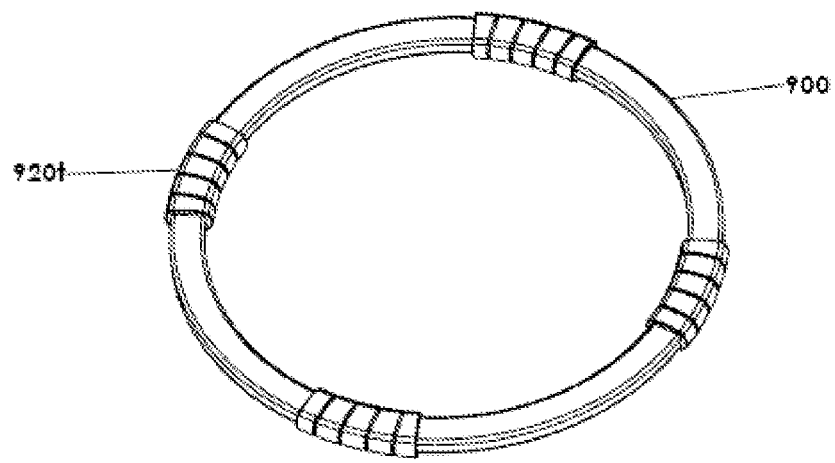

FIGS. 56A and 56B show a still further embodiment of the valve engagement means, attached to an exemplary support element 900 of the present invention. Thus, in FIG. 56A, four short lengths of a soft biocompatible material (such as a biocompatible fabric, silicon, PET etc.) 920i are attached to the inner surface of element 900. Upon expansion of the replacement valve stent within the inner space of the valve support device, the soft material is caused to penetrate between the valve stent struts, thereby forming engagement "teeth" that serve to stabilize the replacement valve—support device assembly. FIG. 56B depicts a very similar set of four valve engagement means 920t formed from a soft biocompatible material. However, in the case of this version, the soft material is provided in the form of tubular sleeves surrounding (partially or completely) support element 900 at the four locations shown in the figure.

Figure 2A:
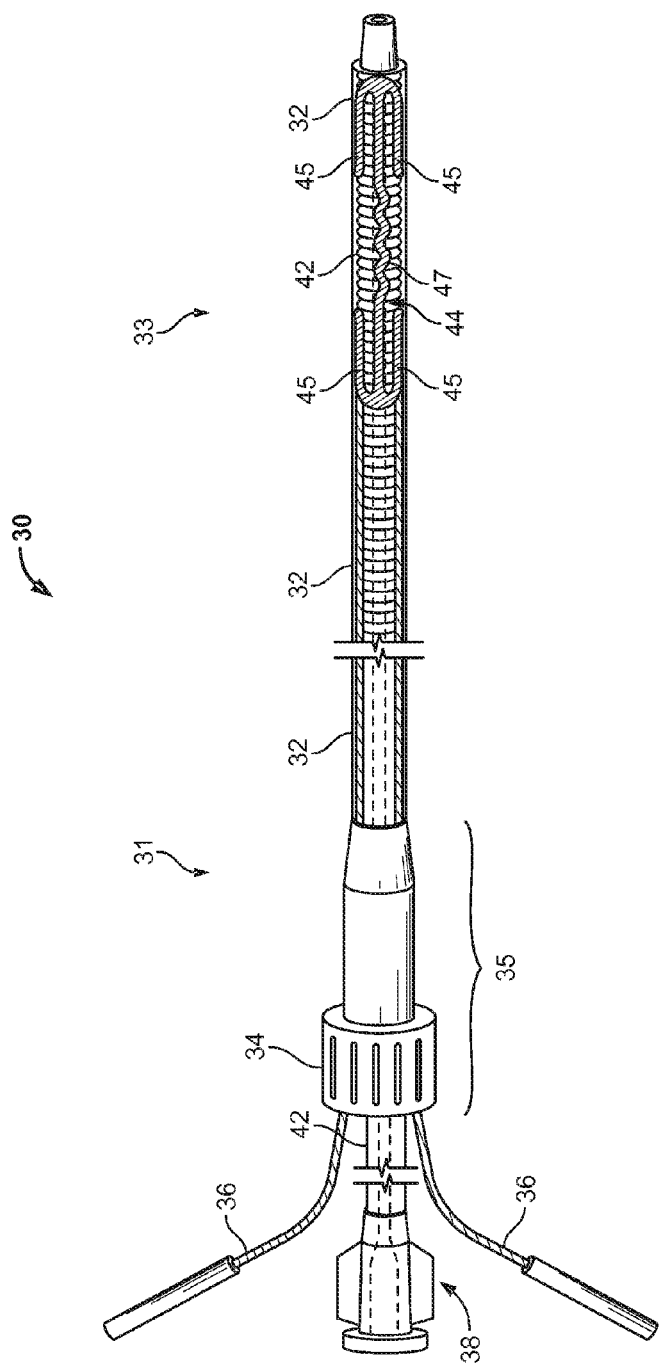
FIGS. 2A-2C illustrate an exemplary delivery system for delivering a replacement cardiac valve support structure.
Figure 2B:
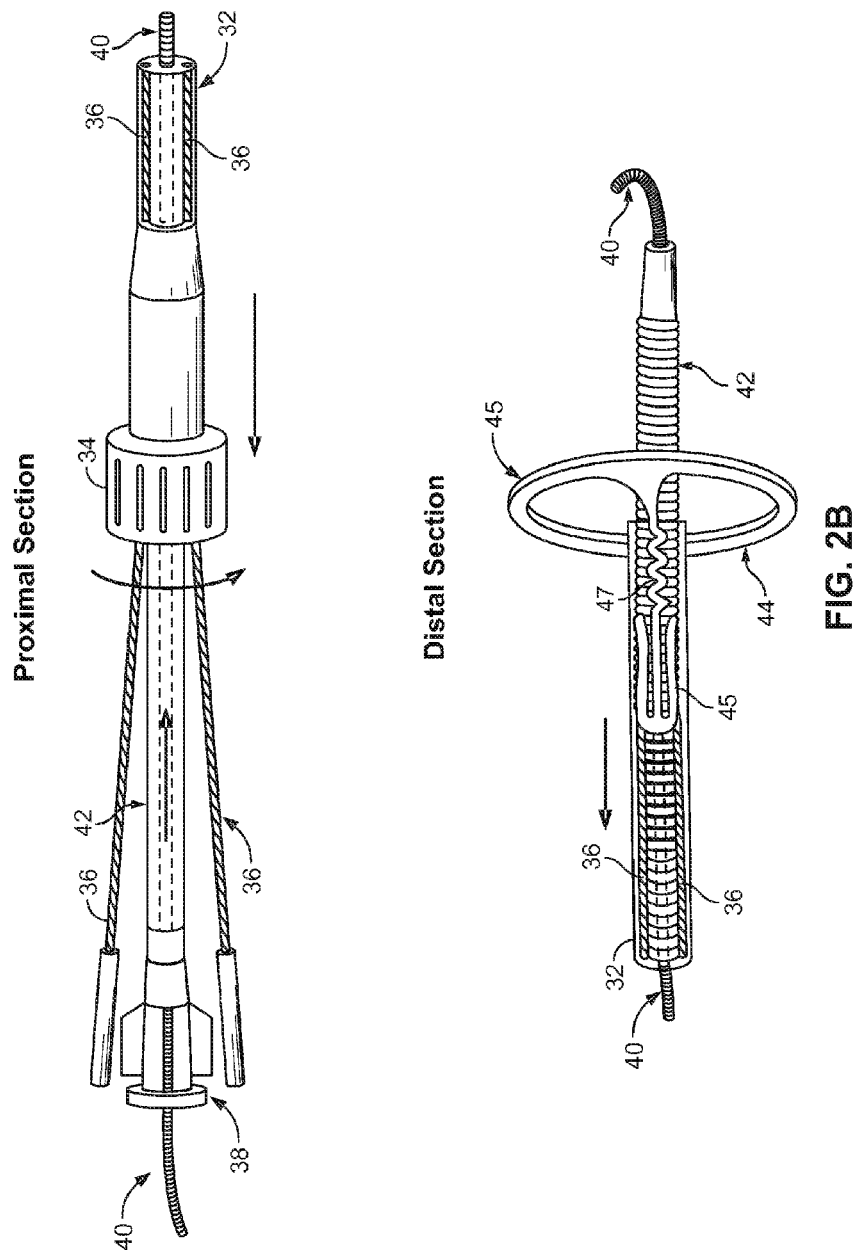

FIG. 2A illustrates an exemplary delivery device and mitral valve support therein in a collapsed delivery configuration. Delivery device 30 includes actuation portion 35 that includes actuator 34. Delivery device 30 also includes elongate body 32, which is secured to actuation portion 35. Delivery device 30 also includes guidewire lumen 42 coupled to luer 38, wherein lumen 42 is adapted to be advanced distally over guidewire 40 (see FIG. 2B) to advance delivery device 30 to a target location within the subject. The portion of delivery device 30 to the left of the broken lines can be considered the proximal portion of delivery device 30, at least a portion of which remains external to the patient during the procedure, providing a user access to actuation portion 35. The portion of the device to the right of the broken line can be considered the distal portion, and is generally considered the portion of the delivery device adapted to be advanced through a patient during the procedure. Actuator portion 35 includes actuator 34 that is adapted to be actuated to control the movement of elongate body 32. Specifically, actuation of actuator 34 controls the axial (i.e., proximal and distal) movement of elongate body 32 relative to inner lumen 42 and to valve support 44. In FIGS. 2A and 2B, rotation of actuator 34 controls the relative axial displacement of elongate body 32, but any other suitable type of actuator can be used and incorporated into the system to control the axial displacement of elongate body 32. Lumen 42 is axially displaceable relative to elongate body 32 by axial movement of the proximal end of lumen 42. Delivery device 30 also includes device coupling members 36, which extend out of the proximal end of the proximal portion of device 30, and also extend distally radially within elongate body 32 yet external to guiding lumen 42. The distal regions of device coupling members 36 are releasably secured to valve support 44 during the deployment procedure (as shown in FIGS. 2A and 2B), but are also adapted to be controllably released from valve support 44 to release the valve support from the delivery device. Coupling members 36 can be actuated by actuating their proximal portions external to the patient to control movement of valve support 44. In FIG. 2A valve support 44 is in a collapsed delivery configuration within elongate body 32 and disposed external to guiding lumen 42. In the delivery configuration, the annular portions 45 of valve support 44 are collapsed down upon bridge members 47 (only one bridge member shown). When collapsed, roughly each half of an annular support 45 is collapsed down and has a C-shaped configuration with a tighter curved configuration (i.e., a portion with a smaller radius of curvature) than when in the expanded configuration (also see the delivery configuration of the valve support shown in FIG. 2C). When in the delivery configuration, bridge members 47 assume a straighter configuration than when in the expanded configuration. As described in more detail below, the annular support elements can be biased to bend at certain locations to ease their collapse during the loading process and during any recollapsing that may be needed. The axial position of the collapsed valve support is controlled by coupling members 36. FIG. 2B illustrates a portion of the process for releasing valve support 44 from delivery device 30 (more details of which are described below). Actuation of actuator 34, shown as rotation of actuator 34, causes elongate body 32 to retract in the proximal direction. Guiding lumen 42 can be maintained in position or advanced distally while the elongate body 32 is retracted. The relative movement between elongate body 32 and coupling members 36 (to which valve support 44 is attached) allows valve support 44 to begin to expand as elongate body 32 is moved proximally. In FIG. 2B, a first of the valve support's elements (and a small portion of bridge members 47) has expanded. Continued retraction of elongate body allows valve support 44 to fully expand, yet still be coupled to coupling members 36.

Figure 2C:
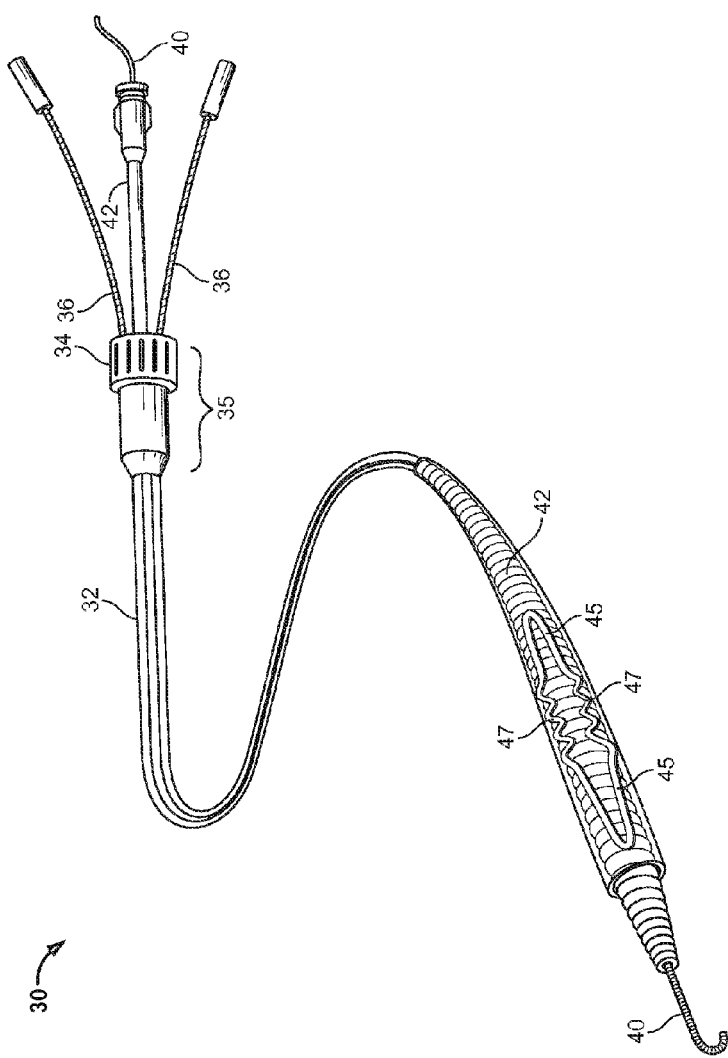

FIG. 2C illustrates an alternative perspective view of delivery device 30, illustrating both of the bridging members 47. In FIG. 2C, however, support elements 45 are adapted to deform generally axially away from the ends of the bridging members when collapsed within elongate body 32 in the delivery configuration.

In the embodiments in FIGS. 2A-2C, elongate body 32 can be, for example without limitation, a catheter, examples of which are well known. Actuation portion 35 can be, for example without limitation, a touhy borst, allowing rotation of actuator 34 to control the axial movement of elongate body 32. Guiding lumen 42 can be, for example without limitation, a corrugated steel reinforced lumen to allow for sufficient flexibility while being advanced through the vasculature. Guiding lumen 42 can also be any other type of suitable guiding lumen.

Access to the mitral valve or other atrioventricular valve will preferably be accomplished through the patient's vasculature percutaneously (access through the skin). Percutaneous access to a remote vasculature location is well-known in the art. Depending on the point of vascular access, the approach to the mitral valve can be antegrade and require entry into the left atrium by crossing the interatrial septum. Alternatively, approach to the mitral valve may be retrograde where the left ventricle is entered through the aortic valve. Alternatively, the mitral valve can be accessed transapically, a procedure known in the art. Additional details of an exemplary antegrade approach through the interatrial septum and other suitable access approaches can be found in the art, such as in U.S. Pat. No. 7,753,923, filed Aug. 25, 2004, the contents of which are incorporated herein by reference.

While the support structures herein are generally described as a support for replacement valves at the mitral annulus, they can be delivered to a desired location to support other replacement cardiac valves, such as replacement tricuspid valves, replacement pulmonic valves, and replacement aortic valves.

Figure 3A:
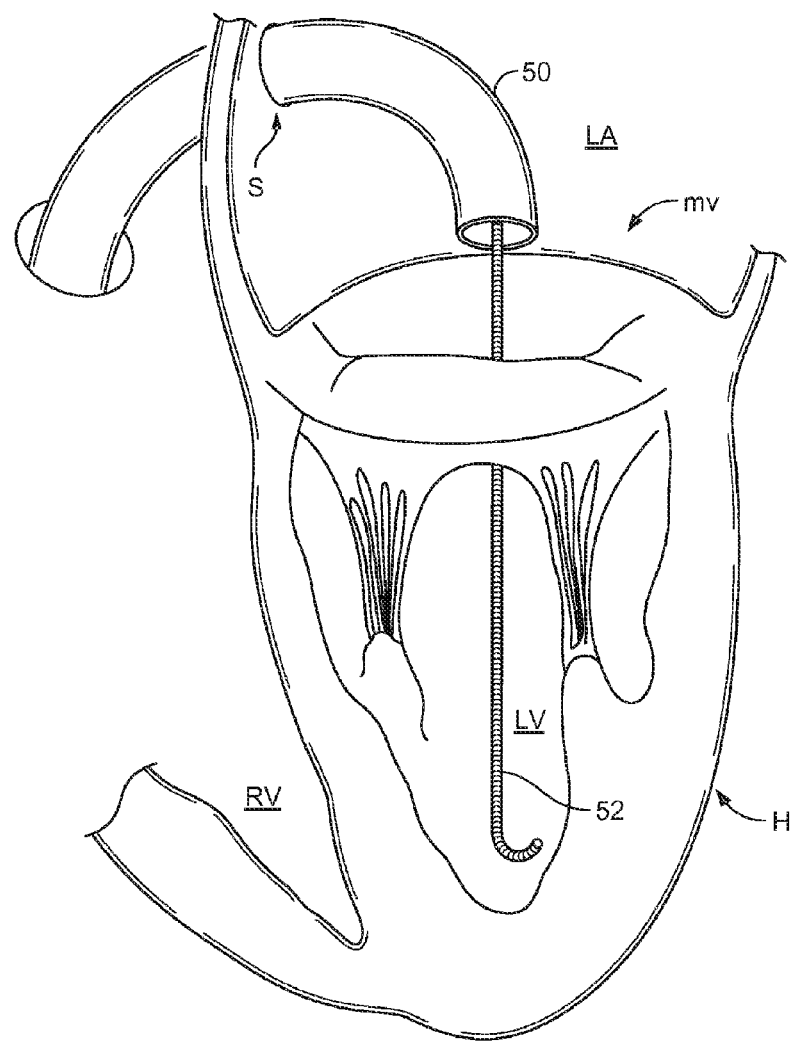
FIGS. 3A-3E illustrate an exemplary method of delivering and deploying an exemplary replacement cardiac valve support structure.

FIGS. 3A-3E illustrate a section view of heart H, illustrating an exemplary method of deploying a valve support within a native mitral valve MV. Access to the mitral valve has been gained using a known approach through the femoral vein, IVC, right atrium, across the interatrial septum S, and into the left atrium LA. Exemplary details of such an approach can be found in, for example, without limitation, U.S. Pat. No. 7,753,923. As shown in FIG. 3A, guide catheter 50 (e.g., an 18 F guide catheter) has been advanced over guidewire 52 through septum S to provide access to the mitral valve. Guidewire 52 has been advanced through the native mitral valve and into the left ventricle to allow the delivery device to be advanced over guidewire 52 and into position within the native mitral valve. Alternatively, guide catheter 50 can be advanced over guidewire 52 into position, and guidewire 52 can then be removed. The delivery device can then simply be advanced through guide catheter 50 without the use of guidewire 52. Guidewire 52 may preferably be left in place, however, to allow a subsequently delivered replacement heart valve to be advanced over the guidewire 52.

Figure 3B:
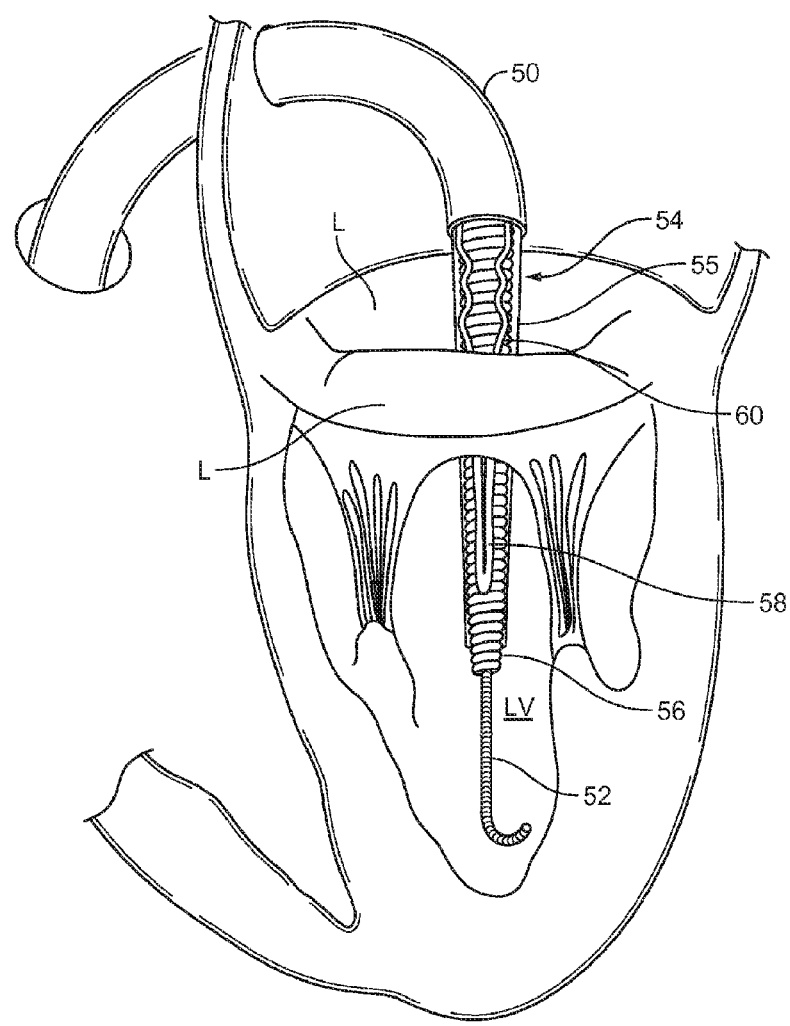

In FIG. 3B, delivery device 54 with a valve support collapsed therein has been advanced over guidewire 52 and through guide catheter 50, and out of the distal end of guide catheter 50. Delivery device 54 is advanced through the leaflets L of the native mitral valve, such that the distal end of elongate body 55 is disposed in the left ventricle LV, as shown in FIG. 3B.

Figure 3C:
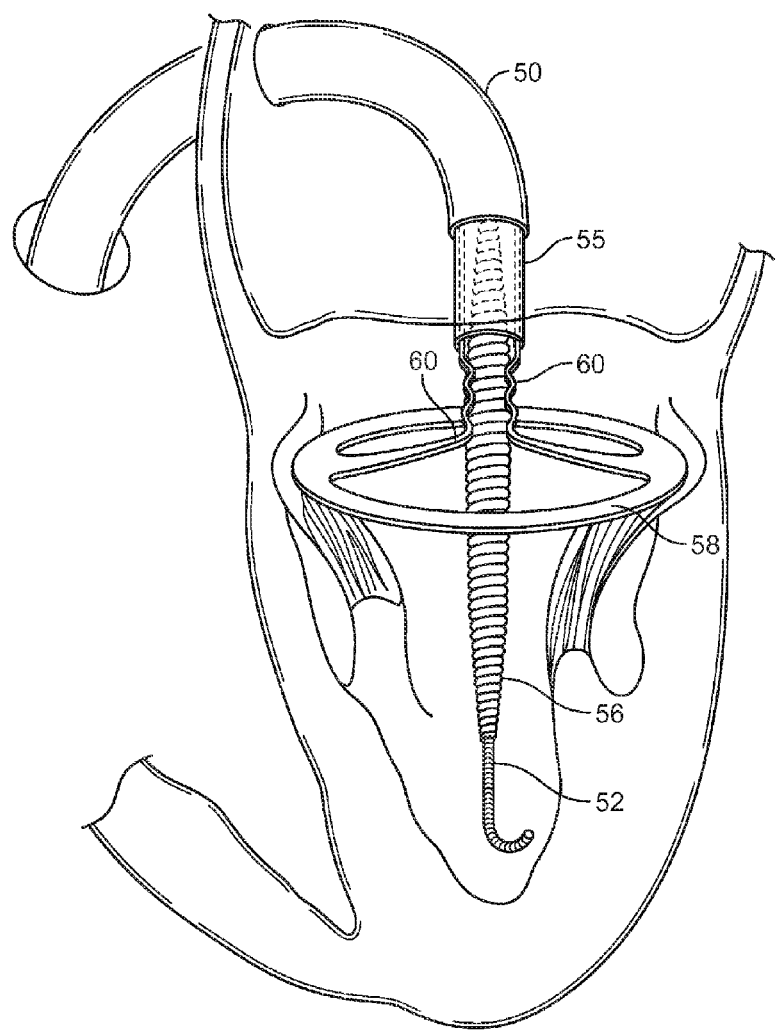
Figure 7:
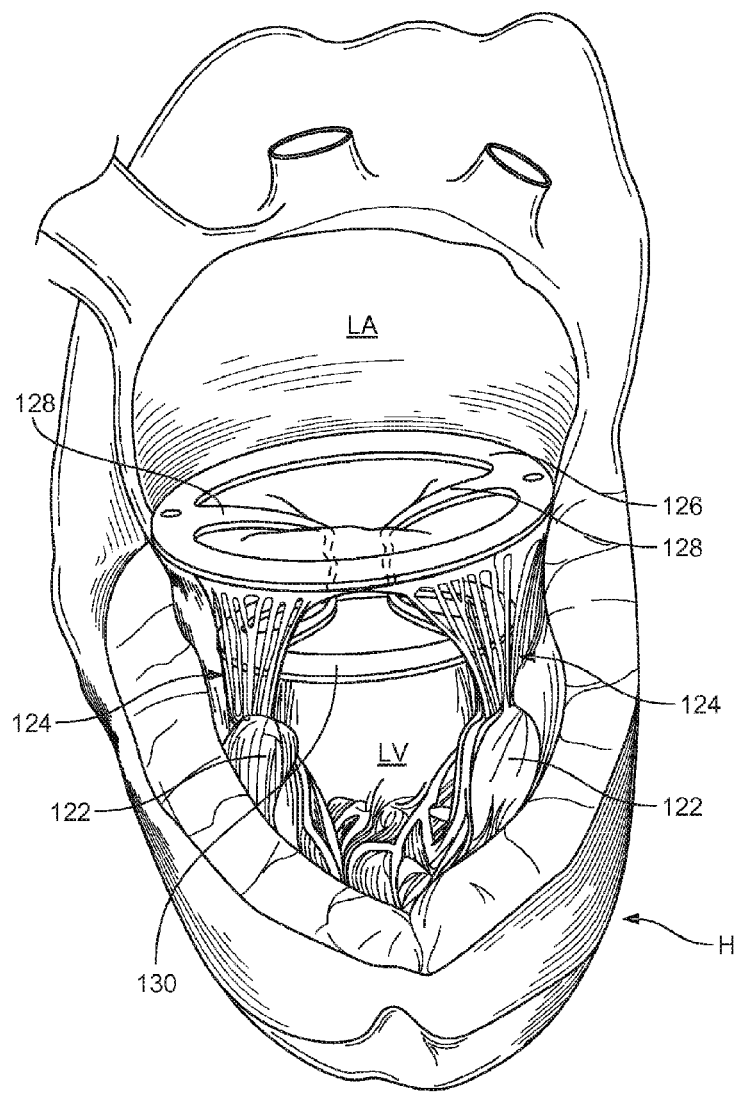
FIG. 7 illustrates an expanded valve support wherein the lower support element has a diameter that is smaller than the diameter of the upper support element.

As shown in FIG. 3C, elongate body 55 is then retracted proximally relative to the valve support, releasing the valve support from elongate body 55 (for example, using an actuator such as actuator 34 in FIGS. 2A-2C). In this embodiment, the valve support is made of a resilient material, such as nitinol, and begins to self-expand as elongate body 55 is retracted. In FIG. 3C, first support element 58 has self-expanded to the expanded annular configuration as shown. When support element 58 expands, it engages ventricular cardiac tissue below the plane of the mitral valve annulus, securing itself against tissue. Support element 58 is preferentially positioned in the sub-annular space, anchoring against the papillary muscles and chords with minimal or no damage to any of them so as not to interfere with their functioning. Support element 58 is preferably expanded distal enough such that native mitral valve leaflets can function even after expansion of support element 58. As discussed above, in some embodiments the lower, or inferior, support element has a smaller diameter than the upper, or superior, support element to match interpapillary distance as measured from the subject being considered. The smaller relative diameter provides the lower support element the ability to oppose the papillary tendons without displacing them. The tendons are attached at one end to the papillary muscles and at the other end to the native leaflets, and displacing the tendons or the muscles would prevent the native leaflets from properly closing, causing regurgitation during the expansion of the valve support. The lower support element is therefore secured in place without interfering with the function of the native leaflets. Referring briefly to FIG. 7, an exemplary valve support is shown expanded in place. Lower support element 130 is shown with a smaller diameter than upper support element 126. Support element 130 is opposed to tendons 124 but is not displacing them, and as such is not interfering with the function of papillary muscles 122 and tendons 124. Support element 130 is expanded in the sub-annular space, while support element 126 is expanded in the left atrium LA. While the embodiments shown herein may appear to show a lower support element that is displacing the tendons and/or papillary muscles, it is intended that the lower support is properly sized such that it is expanded in the manner shown in FIG. 7.

Referring back to FIG. 3C, elongate body 55 has been retracted proximally relative to a portion of bridge members 60, allowing a portion of bridge members 60 to expand. Support element 58 can be recollapsed back within elongate body 55 at this point in the procedure if necessary. The positioning of the valve support can be visualized using known visualization techniques (e.g., fluoroscopy, or any other imaging modalities as necessary) and if it is determined that support element 58 is not positioned properly, elongate body 55 can be advanced distally relative to the valve support, coupling members 64 can be retracted relative to elongate body 55, or a combination of the two can be performed to recollapse at least a portion of support element 58 back within elongate body 55. The valve support can then be repositioned, and support element 58 can then be re-expanded to secure proper placement in the desired anatomical position or space.

Figure 3D:
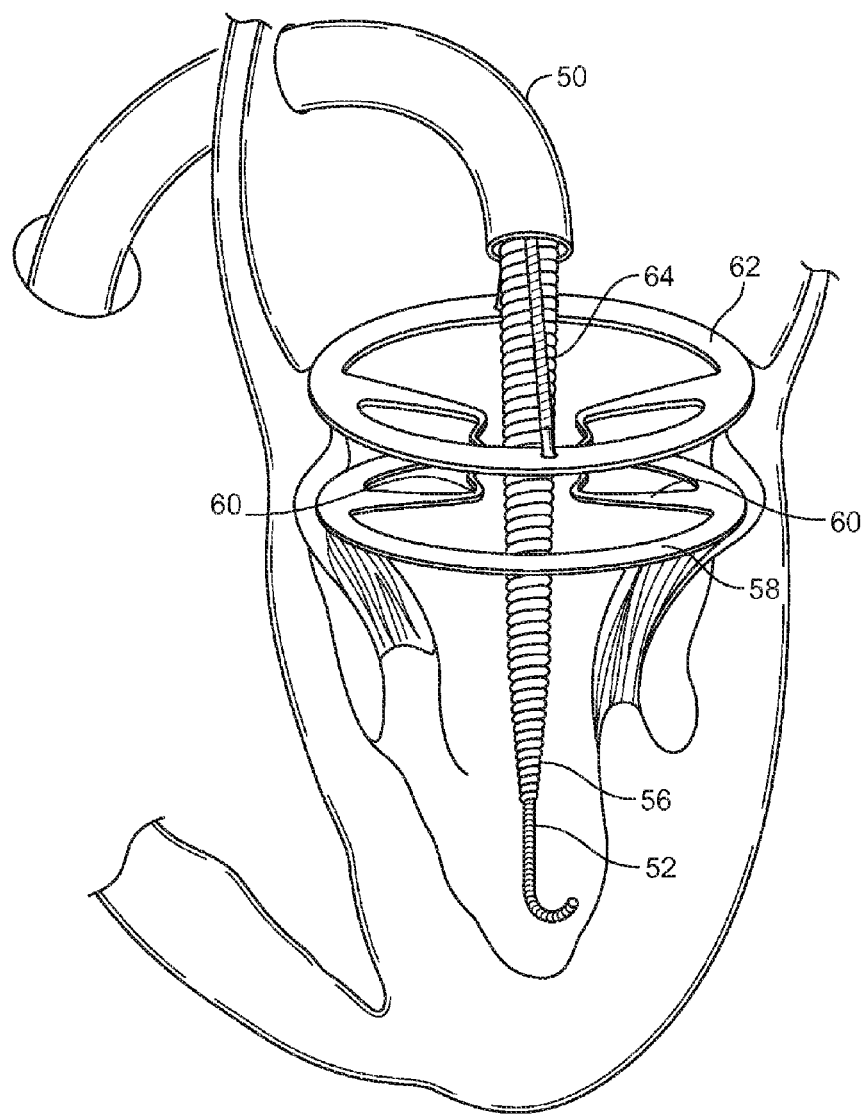

As shown in FIG. 3D, continued proximal retraction of elongate body 55 (not shown in FIG. 3D) allows the second support element 62 to self-expand, securing itself against the lateral wall of the atrium above the mitral valve annulus. In some embodiments the second support element includes one or more fixation elements, such as in the form of anchors, barbs, clips, etc., that help secure the second support element against cardiac tissue, or that are adapted to pierce into cardiac tissue to secure the support element to cardiac tissue. One or more fixation elements, if used, can be disposed around the periphery of the support element. They can assume a collapsed, or delivery configuration for delivery of the system, but can deploy to an expanded, or anchoring, configuration, when released from the delivery system. For example, the fixation elements can be an elastic material that self-expands to an anchoring configuration. Alternatively, the fixation elements can be actuated to reconfigure them to a fixation configuration. In some embodiments, however, the one or more fixation elements are not adapted to change configurations. The mitral valve leaflets are not shown in FIG. 3D for clarity. Coupling members 64 (only one can be seen in FIG. 3D) are still controllably secured to second support element 62. Support element 62 can be recollapsed back within elongate body 55 at this point in the procedure. This can occur as described above with respect to support element 58. In some embodiments support element 62 can be adapted to preferentially bend (for collapsing towards its delivery configuration) at or near the point at which coupling members 64 are secured. If it is determined that support element 62 should be recollapsed within elongate body 52, a proximally directed force can be applied to coupling members 64, thereby applying a force on support element 62. If support element 62 is adapted to preferentially bend at the location at which the coupling members are secured, the force will be applied at the location at which the support is adapted to preferentially bend. This will allow support element 62 to be deformed towards its collapsed configuration more easily and more efficiently. Once support element 62 is collapsed within elongate body 55, continued retracting of coupling members 64 can cause support element 58 to collapse as well. Support element 58, like support element 62, can be adapted to preferentially bend at certain locations, easing the deformation towards its delivery configuration.

The locations on support element 62 (and support element 58) from which bridge members 60 extend are roughly 180 degrees apart from one another, similar to the roughly 180 separation of the native leaflet coaptation points. In the expanded configuration shown in FIG. 3D, the locations on the support elements from which the bridge members extend are generally preferably positioned at the ends of the line of coaptation between the two native valve leaflets. That is, a line connecting the points on the support elements from which the bridge members extend is preferentially (although not necessarily) in alignment with the line of coaptation of the native valve leaflets. One or both support elements may have radiopaque markers at these locations to assist in proper orientation of the valve support in place. By positioning the bridge members in these locations relative to the native leaflets, the bridge members do not interfere with the functioning of the native valve leaflets during the implantation procedure (or at least interfere minimally), even after the valve support is deployed to the fully expanded configuration shown in FIG. 3D. Because the native leaflets can function during this part of the procedure, time is not a critical factor during the deployment of the valve support.

While the support structures herein are generally described as including two bridging elements, the support structures can be have more than two bridging elements disposed in any configuration around the support structures.

Figure 3E:
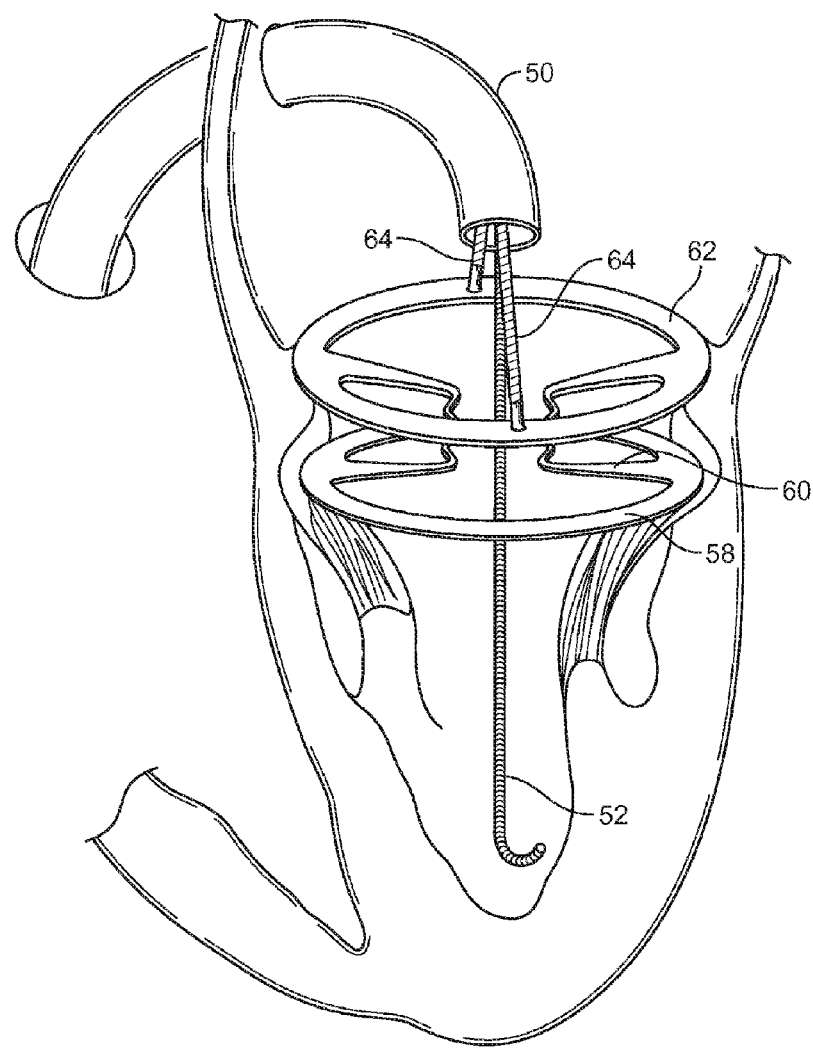

Next, guiding member 56 is retracted from the patient, leaving guidewire 52, guide catheter 50, and elongate body 55 in place, as shown in FIG. 3E. Guide catheter 50 and guidewire 52 can now provide access to the mitral valve to allow a replacement mitral valve to be secured to the valve support which has been expanded and secured within the native valve.

Figure 4A:
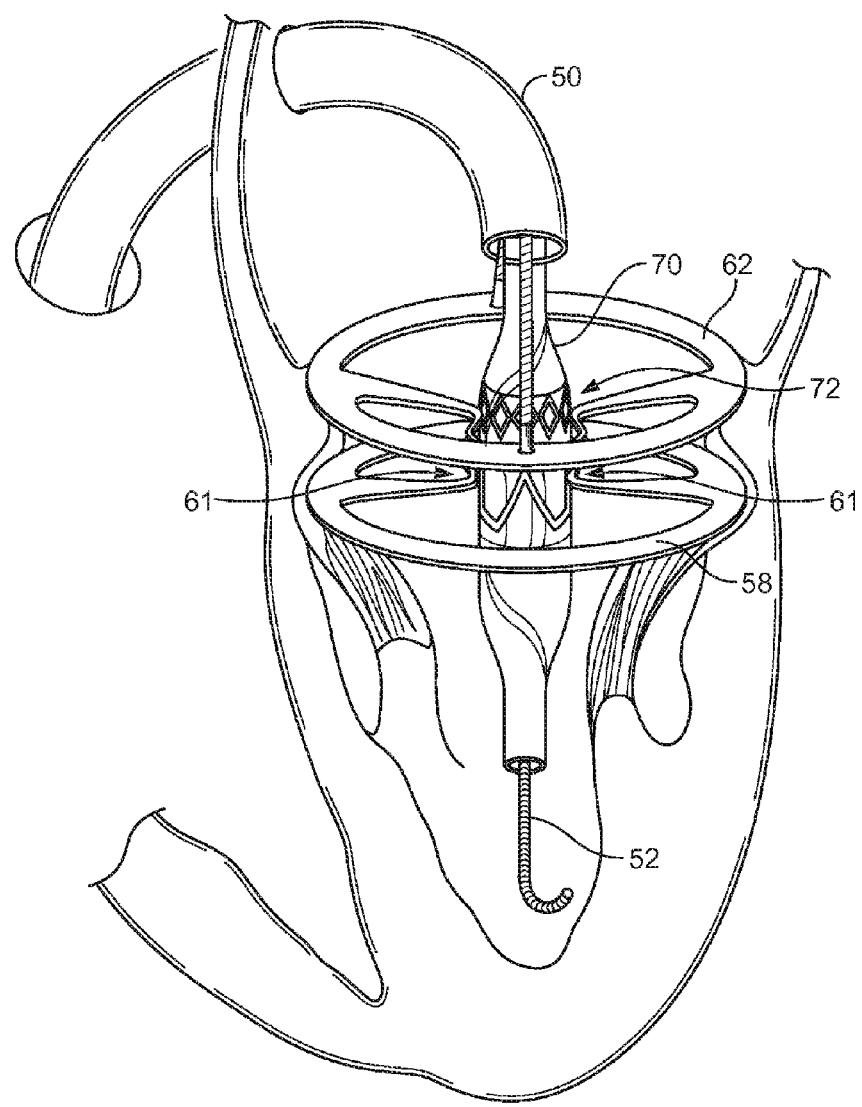
FIGS. 4A-4D illustrate an exemplary method of deploying a replacement heart valve and securing it to a replacement mitral valve support structure.

FIGS. 4A-4D illustrate the subsequent delivery and expansion of an exemplary replacement heart valve. In FIG. 4A, a balloon catheter with balloon 70, along with replacement valve 72 thereon, has been advanced over guidewire 52 and within guide catheter 50 to the position shown radially within the expanded valve support. In general, replacement valve 72, which in this example comprises an expandable stent and replacement leaflets secured thereto, is advanced until it is positioned radially within valve engagement portions 61 of the bridge members. Once the replacement valve is determined to be in an optimal position across the atrio-ventricular line (e.g., using a visualization technique such as echocardiogram), the replacement valve can be expanded.

Figure 4B:
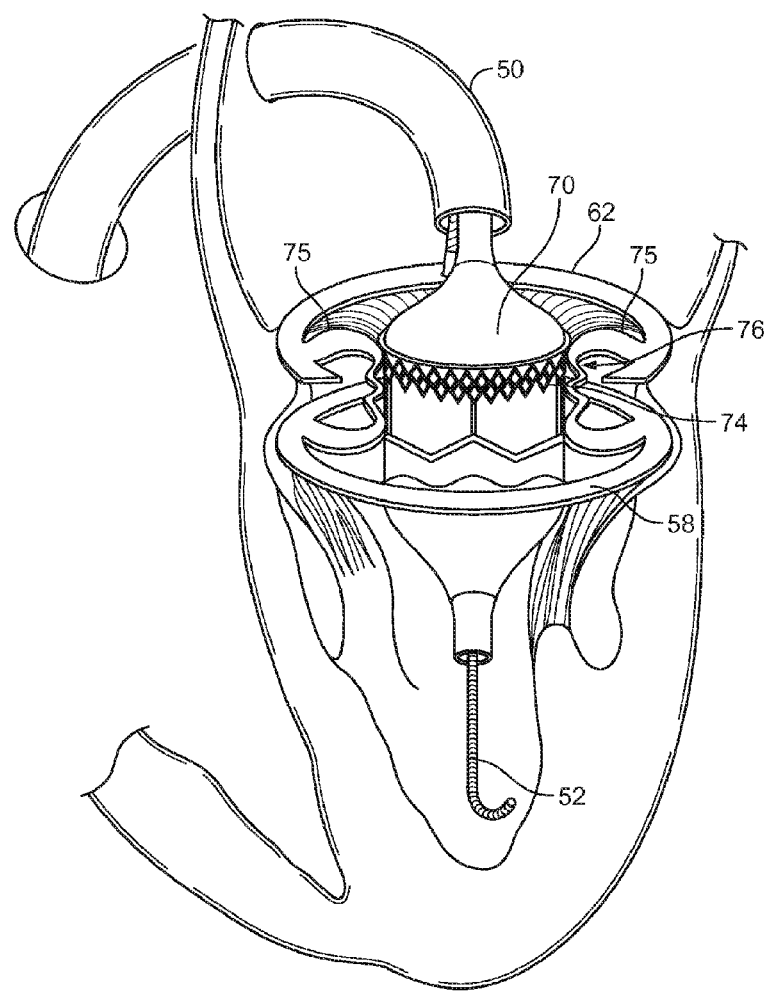

As shown in FIG. 4B, balloon 70 is expanded by filling it with an expansion fluid, a procedure known in the art. Expansion of balloon 70 expands the expandable stent portion of the replacement valve. Expansion of the stent applies radially outward forces on the bridge members of the valve support, causing them to expand (or rather, deform in a general radially outward direction). As the stent expands, the stent pushes the native leaflets outward towards the annulus. As the stent expands, apertures in the stent defined by the stent material are adapted to engage with protrusions or other surface features of the valve engagement portion of the bridge members to secure the expandable stent to the bridge members. The radially inward bias of the bridge members also helps secure the replacement valve within the valve support by applying a radially inward securing force on the stent. The stent is applying a radially outward force on the bridge members as well, and the two interact to allow the replacement valve to be secured in place, preventing the replacement valve from being displaced axially as well as from being collapsed. Additionally, the bridge members can be adapted to assume a preferential expanded configuration (such as is shown in FIG. 4B) when expanded replacement valve expansion process. For example, the bridge members can be adapted to have bending points 75 at which the bridge members will preferentially bend when expanded, which will prevent the two support members from migrating axially away from one another during the replacement valve expansion process. Bending points 75 can also assist in securing the replacement valve relative to the support structure.

Figure 4C:
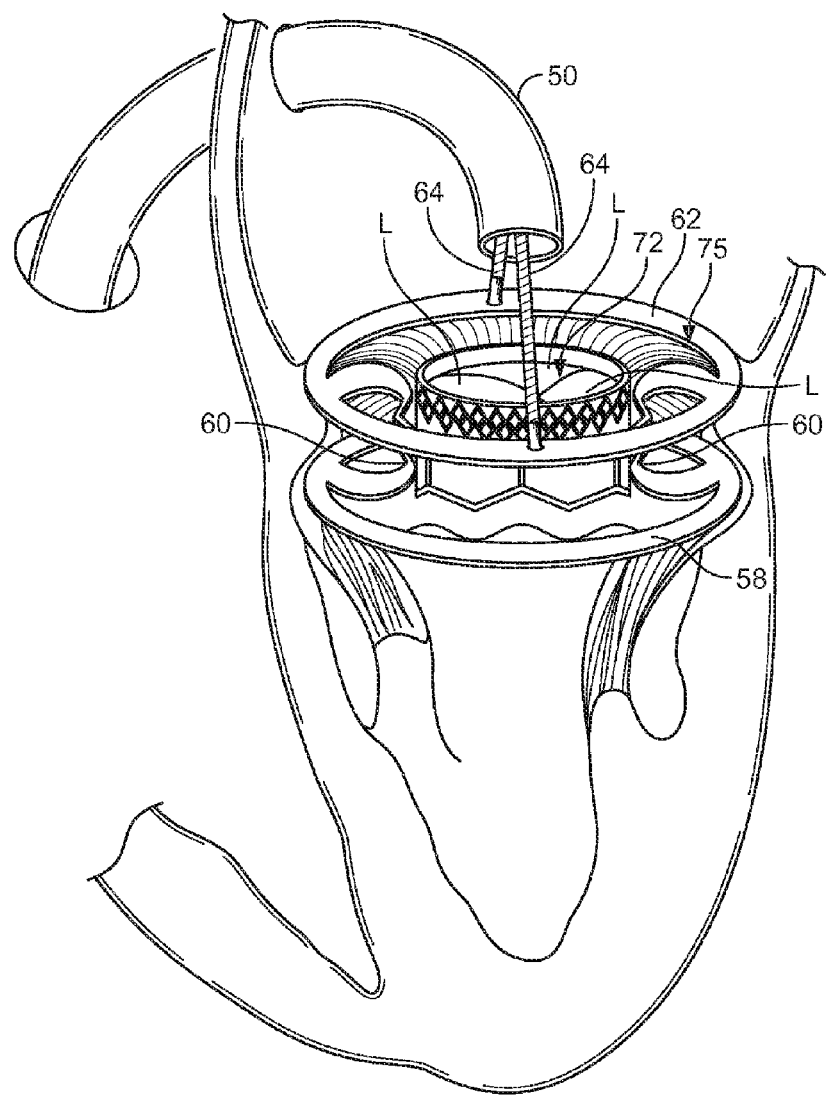

After the replacement valve has been expanded and secured in place, balloon 70 is deflated and withdrawn, along with the guidewire, from the patient, as is shown in FIG. 4C. Once the balloon is deflated, the leaflets L of the replacement cardiac valve begin to function. Three leaflets are shown to illustrate that known replacement aortic valves, mere examples of which are described in U.S. Pat. No. 7,585,321, filed May 27, 2005, can be used in this exemplary procedure to replace the native mitral valve.

While a balloon expandable replacement heart valve has been shown, the replacement heart valve can be self-expanding as well.

Figure 4D:
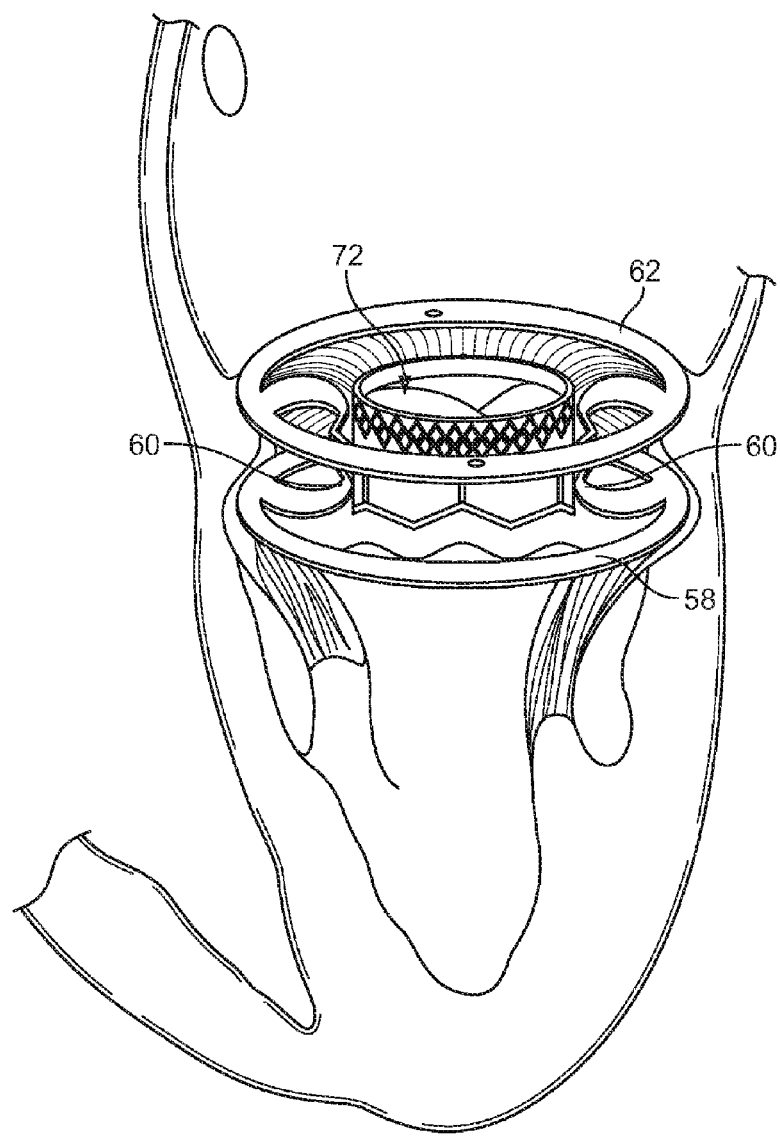

Once the replacement valve is secured in place within the valve support, coupling members 64 are disengaged from support element 62. In this exemplary embodiment the distal ends of coupling members 64 have threads which adapted to engage threaded bores within support element 62. Rotation of coupling members 64 causes the coupling members 64 to be unscrewed from support element 62, thereby uncoupling the coupling members 64 from support 62. Guide catheter 50 is then removed from the patient, leaving the implant in place, as shown in FIG. 4D.

As set forth above, the mitral valve can be accessed via a transapical approach, or though the apex of the heart. In such an approach, coupling members 64 would be secured to inferior support element 58 rather than superior support element 62, as shown in the embodiments herein. The coupling members 64 could still be actuated in the same manner as described herein.

FIGS. 5A-5D illustrate an exemplary delivery device and mitral valve support therein in a delivery configuration. The delivery device and mitral valve support are similar to those shown in the embodiments in FIGS. 2A-2C. Delivery device 80 includes hemostasis valve 82 comprising rotating male luer lock 81 and female luer sideport 83. Delivery device 80 also includes elongate body 84 secured to actuator 85, wherein actuator 85 is adapted to be rotated to control the axial movement of elongate body 84. Device 100 is collapsed within elongate body 84 and is disposed radially outward relative to lumen 86. Delivery device 80 also includes guidewire lumen 86, which is adapted to receive guidewire 90 therein, coupled to luer 88, which are adapted to move axially relative to elongate body 84. Coupling members 92 are reversibly secured to valve support 100 as set forth in the embodiments above. Other details of delivery device 80 can be the same as those described in the embodiments above.

Figure 5A:
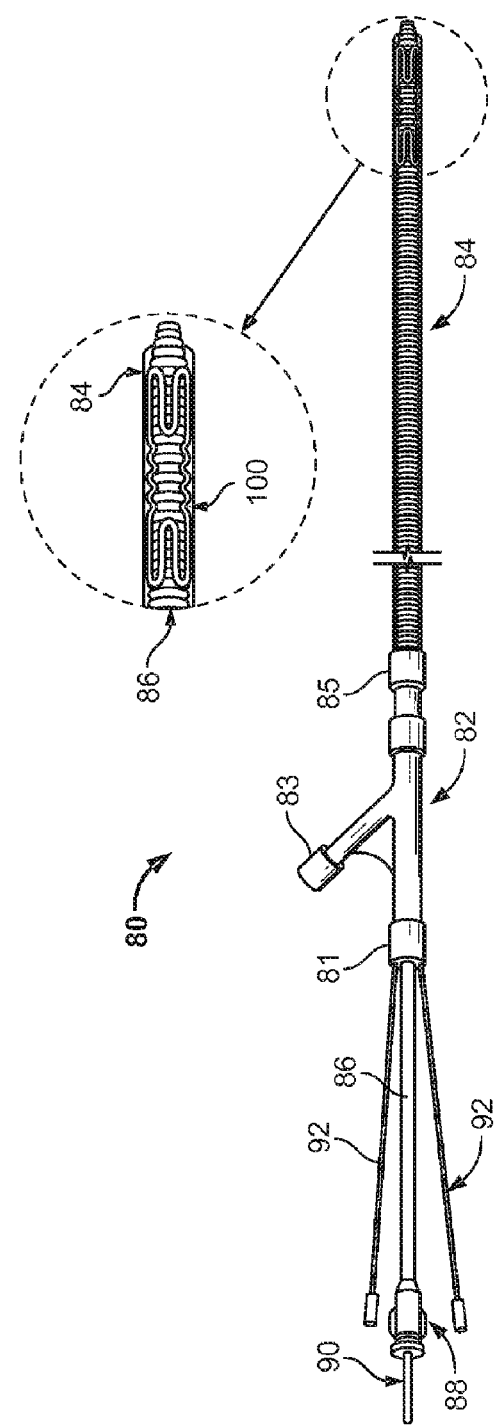
FIGS. 5A-5D illustrate an exemplary delivery system for delivering a cardiac mitral valve support structure.
Figure 5B:
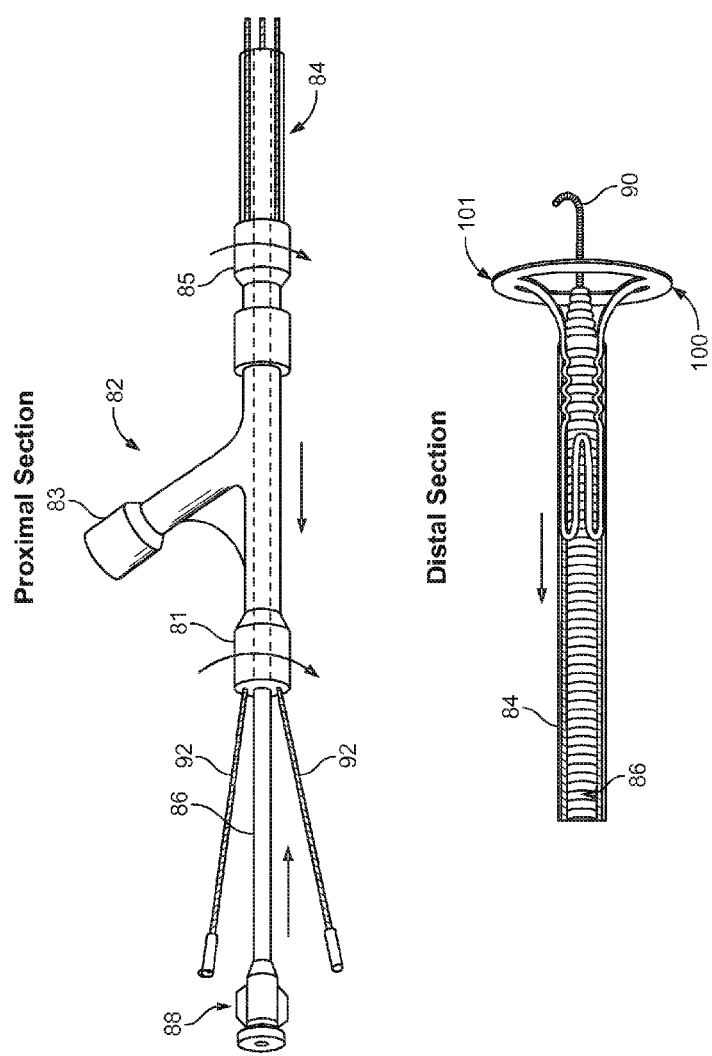

In FIG. 5B, actuation of actuator 85 causes proximal retraction of elongate body 84 relative to valve support 100. This causes distal support element 101 of valve support 100 to begin to self-expand to a deployed configuration against tissue (anatomy not shown for clarity), such as in the embodiment in FIG. 3A-3E. Hemostasis valve 82 can alternatively, or in addition to, be pulled proximally (as indicated in by the arrow in FIG. 5B) to cause elongate body 84 to retract relative to valve support 100. In addition, or alternatively, guiding lumen 86 can be advanced distally (as indicated by the arrow in FIG. 5B) relative to elongate body 84. These types of motion can cause or assist in the expansion of the valve support.

Figure 5C:
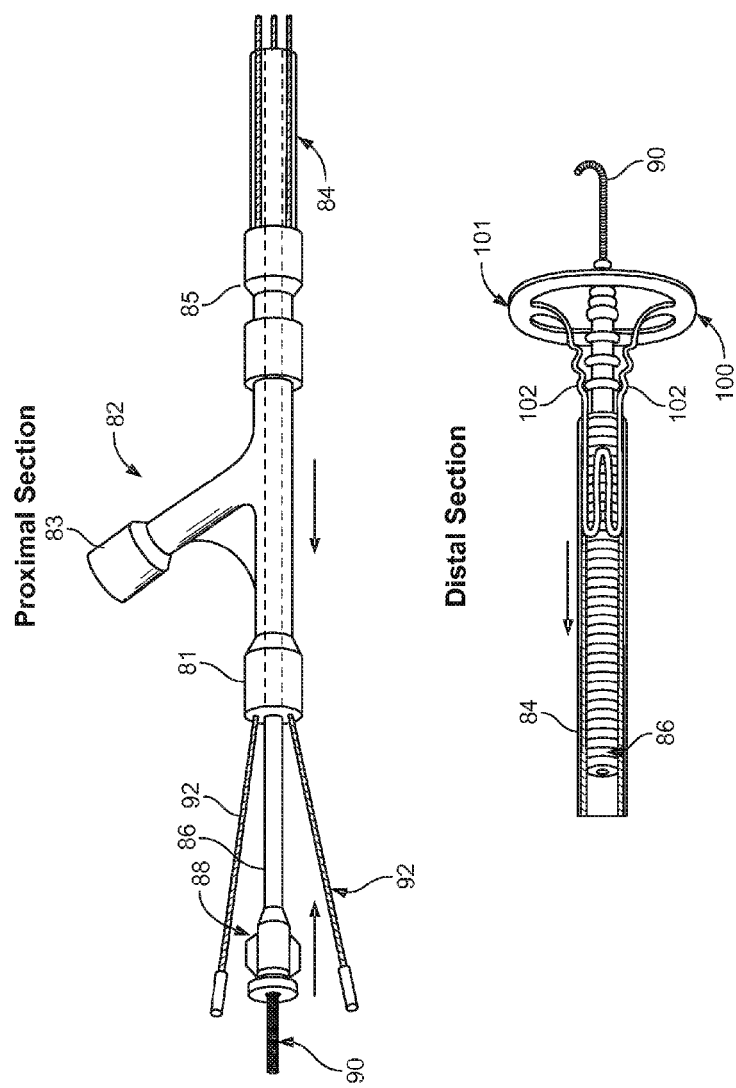
Figure 5D:
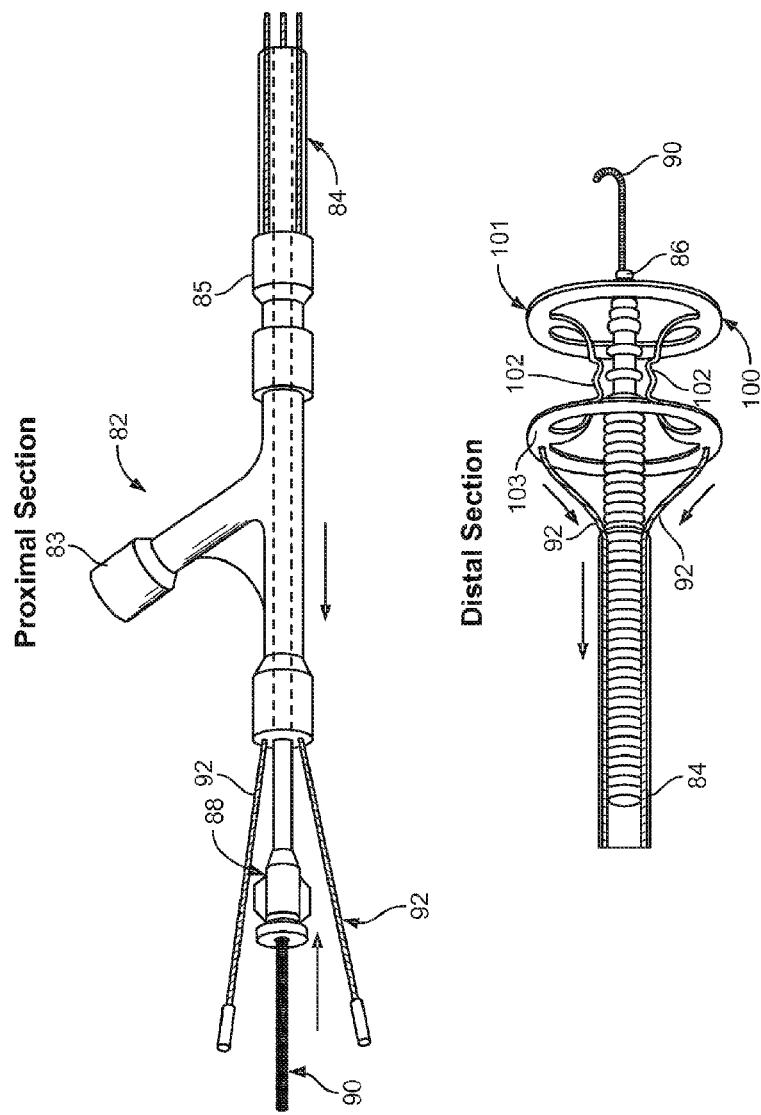

As shown in FIG. 5C, bridge members 102 of valve support 100 continue to be expanded by relative proximal movement of elongate body 84. This can be performed by proximal movement of the elongate body (as indicated by the arrow), by distally advancing lumen 86, or any combination of the two. Continued relative movement of elongate body 84 eventually causes second support element 103 to expand to a deployed configuration, as shown in FIG. 5D. As second support element 103 self-expands, coupling members 92 can extend radially outward along with support element 103.

Once the valve support is determined to be positioned in place, guiding lumen 92 can be removed to allow for a replacement heart valve to be positioned within the valve support, an example of which is shown in FIGS. 4A-4D.

Figure 6:
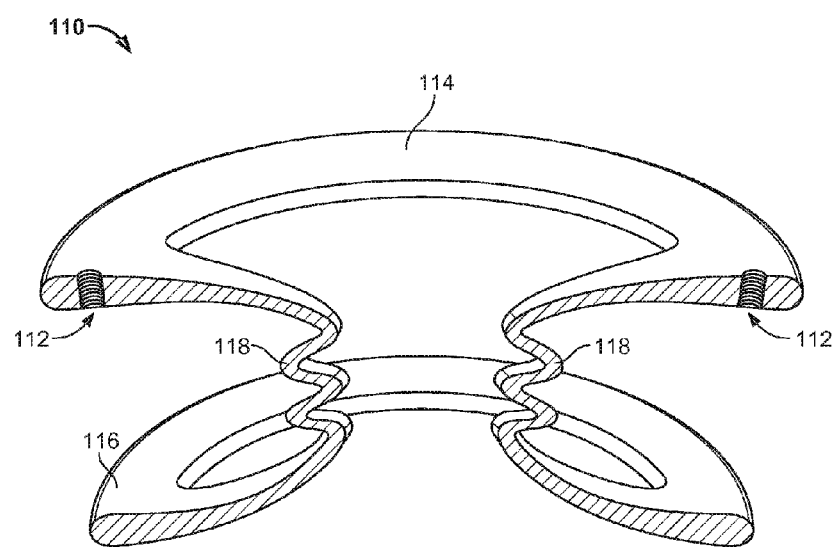
FIG. 6 illustrates a sectional view of an exemplary replacement mitral valve support.

FIG. 6 illustrates a section view of one-piece valve support 110, including first support element 114, second support element 116, bridging members 118, and coupling elements 112, which are shown as threaded bores and are adapted to securely engage threaded portions of coupling members, examples of which are described above.

Figure 8A:
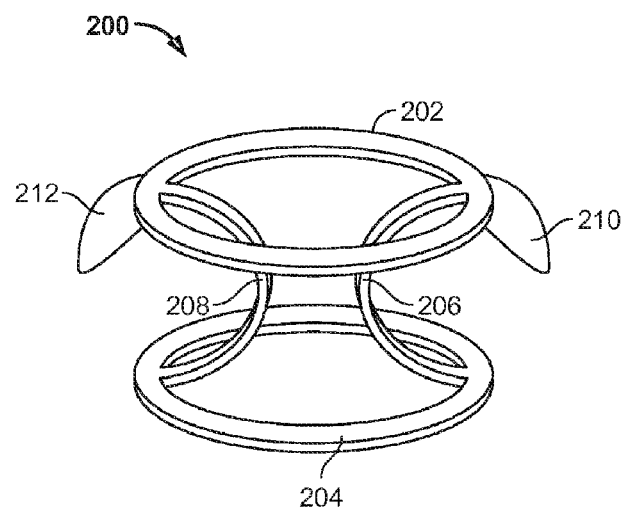
FIGS. 8A and 8B illustrate an embodiment comprising seals to reduce leakage.
Figure 8B:
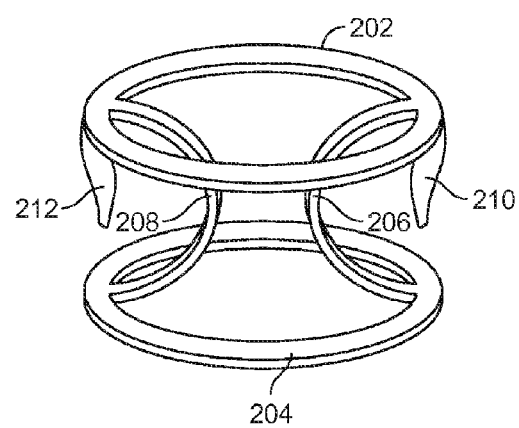

FIGS. 8A and 8B illustrate an alternative embodiment of a valve support. Valve support 200 includes components to mitigate para-valvular leakage. In addition to support elements 202 and 204 and bridge members 206 and 208, valve support 200 includes one or more flaps 210 and 212. The flaps extend coverage of the valve support system and help mitigate para-valvular leakage, functioning similarly to mudflaps on an automobile. During delivery exemplary flaps 210 and 212 are tucked around or against superior support element 202 as shown in FIG. 8B, and upon deployment from the catheter, flaps expand or extend to the configuration shown in FIG. 8A (native valve not shown for clarity). The flaps can be made of a flexible biocompatible material such as a wide variety of polymeric compositions. The flaps can be secured to the valve support by any suitable mechanism, such as by suturing the flaps to the support element, or to covered material, and using the bridge member to prevent the suture material from being displaced.

When deployed, in some embodiments the flaps are disposed above the annulus and over the side of the superior support element, which may not be extending all the way to the atrial wall. This can extend coverage of the valve support system for a few millimeters, reducing para-valvular leakage. Alternatively, in some embodiments in which the support element is larger, the flaps are urged against the atrial tissue. In this use, the flaps act as an additional seal when the valve support system is in place. The one or more flaps can therefore be a component of the valve support system that reduces para-valvular leakage and/or acts as an additional seal.

Figure 57:
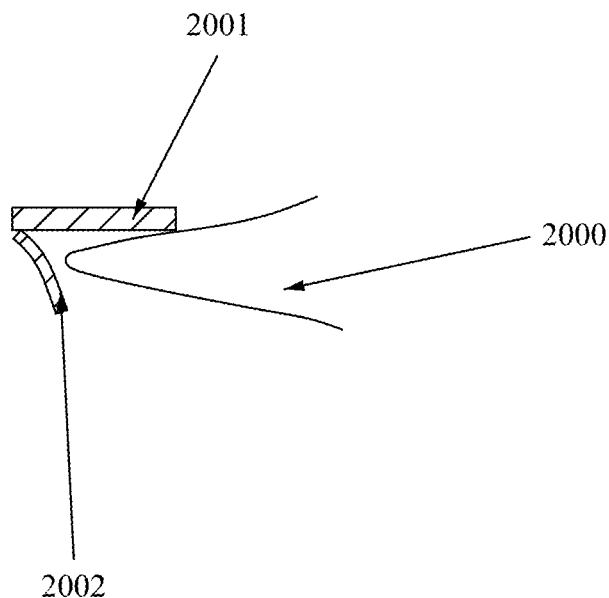
FIG. 57 provides a side view of an exemplary support of the present invention, shown in a position on the mitral annulus, and exemplifying a fabric drape attached to the inner part of the ring.

As mentioned hereinabove, in certain other embodiments, paravalvular leakage is prevented by the use of fabric drapes attached to one or both of the support elements, preferably to the support element which in use will become the upper of said elements. Thus, FIG. 57 illustrates a side view of an exemplary upper ring 2001 (upper support element) of a ring-like valve support of the invention, shown in a position on the mitral annulus 2000, and comprising a fabric drape 2002 attached to the inner circumference of the ring. The unique position of the drape on the inner circumference of the upper ring presents several distinctive advantages: the drape functions as a "valve leaflet" between the mitral annulus and the upper ring, thus during systole, when fluid flows out from the ventricle, the drape is pushed upwards, towards the annulus, by the flow of blood, and this movement improves the sealing between the upper ring and the annulus, (indicated by the arrows in FIG. 57), thus essentially functioning as a valve between the ring and the annulus, and thus preventing paravalvular leakage.

Figure 58:
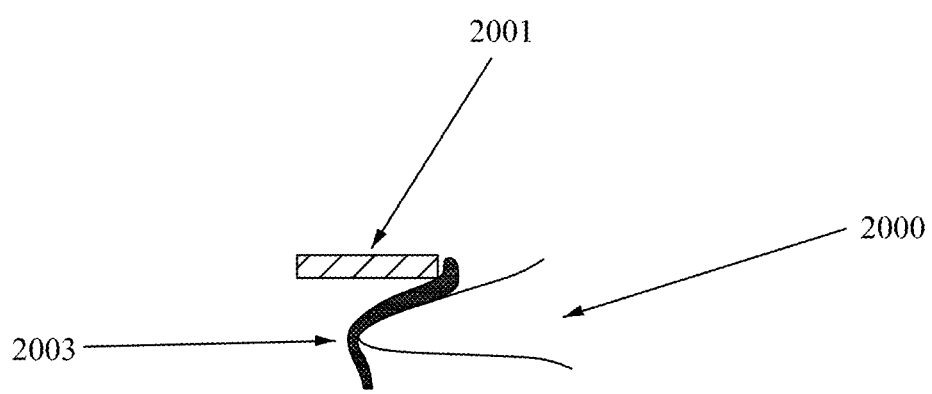
FIG. 58 illustrates a side view of another exemplary upper ring (upper support element) of a valve support of the invention, shown in a position on the mitral annulus, and exemplifying a fabric drape attached to the outer (distal) part of the ring.

FIG. 58 illustrates a side view of an exemplary upper ring 2001 (upper support element) of a ring-like valve support of the invention, shown in a position on the mitral annulus 2000, and exemplifying a fabric drape 2003 attached to the outer circumference of the ring. The position of the drape on the outer part of the upper ring allows it to function as a sealing element between the ring and the annulus (similar to the function of a sealing "o" ring), so when the ring is approximated and attached to the area of the annulus the drape functions to seal the annulus and prevents paravalvular leakage. In some embodiments of this invention the length of the drape is such that the edge of the drape extends into the left ventricle (as shown in FIG. 58). This is advantageous since this extended drape element improves the sealing and prevents leakage between the outer area of the ring and the mitral annulus.

Exemplary materials for the drape of the invention are any kind of biocompatible fabric, for example Dacron, ePTFE. Exemplary sized of the drapes of the invention are length of 2 mm-20 mm and width of 2 mm-60 mm, thus covering a part of the ring or the whole circumference of the ring.

Figure 59:
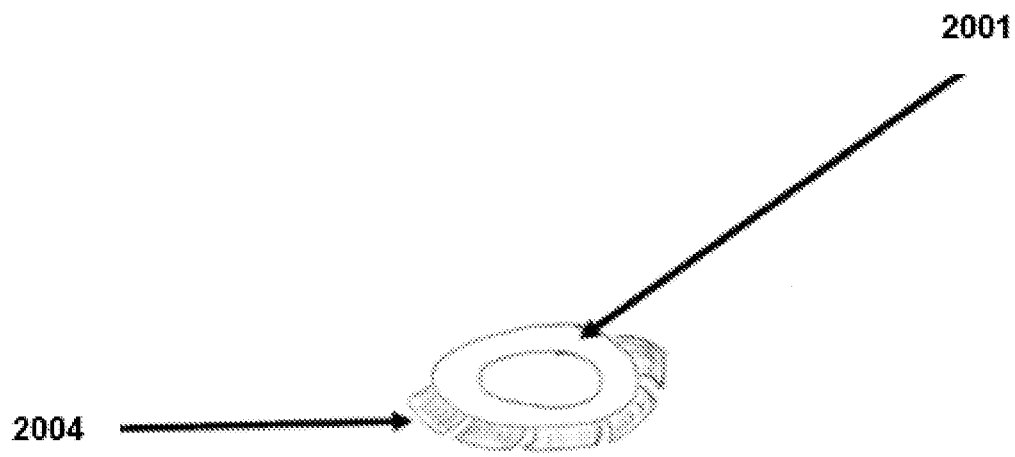
FIG. 59 provides a perspective view of an exemplary upper support element of a valve support of the invention, fitted with multiple fabric drapes.

FIG. 59 illustrates a perspective view of an exemplary upper ring 2001 (upper support element) of a valve support of the invention, exemplifying multiple fabric drapes 2004 of the invention. Five such separate drapes are shown, with the rest of the drapes not showing in the illustration. Preferably there is a small overlap between drapes, such that there is no leakage between adjacent drapes.

Figure 60:
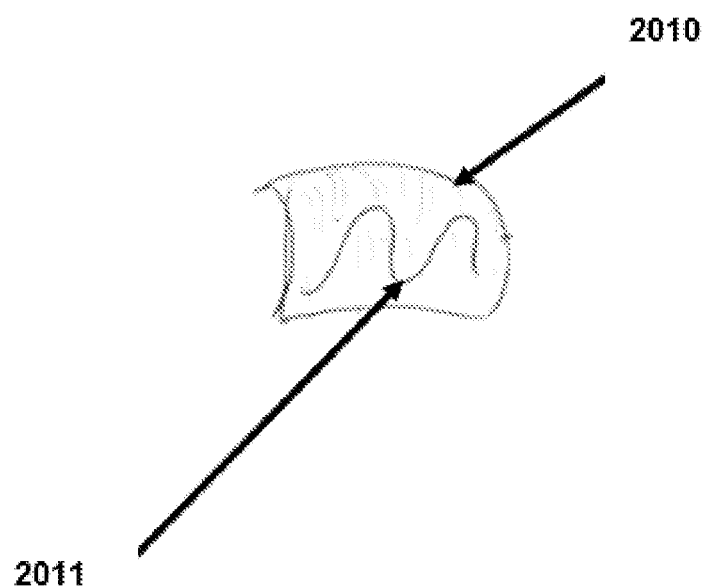
FIG. 60 illustrates an exemplary design of a fabric drape of the invention.

FIG. 60 illustrates a further design for the fabric of a drape of the invention. Drape 2010 as shown in this figure is made of biocompatible fabric. In order to give the drape a stable form (in order that it will have a predetermined shape), a biocompatible metal wire 2011 is sewn into the material of the drape during its manufacturing. Exemplary materials for the wire are stainless steel or Nitinol. The metal wire can be shaped according to a predetermined requirement, and maintains this shape due to the mechanical properties of the wire. The advantage of this predetermined shaping is that the shape may be designed such that it will improve the sealing between the ring and the annulus, so that the flow will direct the drape towards sealing the annulus, moving the drape closer to the annulus and preventing paravalvular leakage.

While some embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:
1. A cardiac valve support adapted for endovascular delivery to a cardiac valve, comprising:
   first and second support elements constructed from a biocompatible metal, each of said support elements having a collapsed delivery configuration and a deployed configuration;

and wherein only two bridging members extend from the first support element to the second support element, said bridging members having a delivery configuration and a deployed configuration, wherein said bridging members extend radially inward from the first and second support elements in the deployed configuration, wherein said bridging members extend from locations on each of the support elements that are approximately 180 degrees apart from each other;

wherein at least one of the support elements in its deployed configuration is provided in the form of a flat annular ring having an outer radius (Ro) and an inner radius (Ri);

and wherein the difference between Ro and Ri significantly larger than a thickness of the at least one support element.

2. A cardiac valve support adapted for endovascular delivery to a cardiac valve, comprising:

first and second support elements constructed from a biocompatible metal, each of said support elements having a collapsed delivery configuration and a deployed configuration;

and wherein only two bridging members extend from the first support element to the second support element, said bridging members having a delivery configuration and a deployed configuration, wherein said bridging members extend longitudinally, and without any appreciable radial curvature, between first and second support elements in the deployed configuration, wherein said bridging members extend from locations on each of the support elements that are approximately 180 degrees apart from each other;

wherein at least one of the support elements in its deployed configuration is provided in the form of a flat annular ring having an outer radius (Ro) and an inner radius (Ri);

and wherein the difference between Ro and Ri significantly larger than a thickness of the at least one support element.

3. The cardiac valve support of claim 1 or claim 2, wherein at least one of the first and second support elements has an outer perimeter that is entirely rigid.

4. The cardiac valve support of claim 1 or claim 2, wherein at least one portion of the inner perimeter of at least one of the support elements is elastically deformable in a radial direction.

5. The cardiac valve support of claim 1 or claim 2, wherein the difference (Rd) between the outer radius (Ro) and the inner radius (Ri) is in the range of 1-14 mm.

6. The cardiac valve support of claim 5, wherein the ratio between Rd and a thickness of the flat annular ring is between 10:1 and 20:1.

7. The cardiac valve support of claim 5, wherein the inner diameter of the flat annular ring is in the range of 23-29 mm and the outer diameter thereof is in the range of 30-50 mm.

8. The cardiac valve support of claim 5, wherein a thickness of the flat annular ring is in the range of 0.25-0.6 mm.

9. The cardiac valve support of claim 1 or claim 2, wherein said support further comprises one or more extensions, attached to the bridging members or to one or both support elements, such that portion(s) of said one or more such extensions form a guidance element that is capable of centering a wire that is passed through the center of said support.

10. The cardiac valve support of claim 1 or claim 2, wherein the bridging members and/or the support elements are fitted with heart tissue anchoring means adapted to securely anchor said support to the heart wall.

11. The cardiac valve support of claim 1 or claim 2, further comprising one or more intra-ventricular and/or intra-atrial stabilizing elements.

12. The cardiac valve support according to claim 11, wherein the stabilizing elements are selected from the group consisting of complete ring structures, partial rings, curved arms or wings, and elongate arms or wings.

13. A system adapted for endovascular delivery or transapical delivery to replace a mitral valve, comprising:

a cardiac valve support according to claim 1 or claim 2; and a replacement heart valve comprising an expandable anchor and a plurality of leaflets adapted to be secured to the cardiac valve support.

14. The system of claim 13, wherein the replacement heart valve is a prosthetic aortic valve.

* * * * *